United States Patent [19]
Woo et al.

[11] Patent Number: 5,700,817
[45] Date of Patent: Dec. 23, 1997

[54] CYCLIC LIPID DERIVATIVES AS POTENT PAF ANTAGONISTS

[75] Inventors: Soon Hyung Woo; Sung Kee Chung; Soo Ho Ban; Byoung Eog Kim; Si Hwan Kim, all of Pohang, Rep. of Korea

[73] Assignees: Pohang Iron & Steel Co., Ltd.; Research Institute of Industrial Science & Technology, both of Kyong Sang Book-Do, Rep. of Korea

[21] Appl. No.: 553,843

[22] Filed: Nov. 6, 1995

Related U.S. Application Data

[63] Continuation of Ser. No. 193,163, Feb. 10, 1994, abandoned.

[30] Foreign Application Priority Data

Apr. 7, 1993 [KR] Rep. of Korea ............ 93-5778

[51] Int. Cl.$^6$ .................... A61K 31/44; C07D 401/12
[52] U.S. Cl. .................... 514/340; 514/336; 514/357; 546/279.7; 546/281.7; 546/268.1; 546/309; 546/175; 546/335; 548/204
[58] Field of Search .................... 546/279.7, 281.7, 546/309, 268.1, 335; 514/340, 357

[56] References Cited

U.S. PATENT DOCUMENTS

| | | | |
|---|---|---|---|
| 4,665,197 | 5/1987 | de Nie-Sarink et al. | 548/953 |
| 4,701,534 | 10/1987 | Mason et al. | 548/950 |
| 4,851,450 | 7/1989 | Demopoulos | 514/738 |
| 4,891,363 | 1/1990 | Nakamura et al. | 514/94 |
| 4,940,706 | 7/1990 | Bartoli et al. | 514/231.5 |
| 4,945,098 | 7/1990 | Grue-Sorensen et al. | 534/365 |
| 4,987,132 | 1/1991 | Mase et al. | 514/252 |
| 4,997,843 | 3/1991 | Carceller et al. | 514/336 |
| 5,004,569 | 4/1991 | Meier et al. | 560/122 |
| 5,047,420 | 9/1991 | Graham et al. | 514/484 |

FOREIGN PATENT DOCUMENTS

| | | |
|---|---|---|
| 0327962 | 8/1985 | European Pat. Off. |
| 0146258 | 11/1986 | European Pat. Off. |
| 0216228 | 10/1987 | European Pat. Off. |
| 0257921 | 11/1988 | European Pat. Off. |
| 0353474 | 2/1990 | European Pat. Off. |
| 57-67589 | 4/1982 | Japan. |
| 60-104066 | 6/1985 | Japan. |

OTHER PUBLICATIONS

*Chemical Abstracts*, vol. 114, No. 19 (1991), Tsushima et al., "Preparation of pyridinium compounds as platelet–activatingfactor (PAF) antagonists", p. 769, col. 1.
*Chemical Abstracts*, vol. 116, No. 13 (1992), Kertscher et al., "PAF antagonistswith phospholipid structure. Part 2: Phospholipids with heteroarene head groups and increased phosphorus–nitrogendistance: synthesis, characterizatio-nand structure–activityrelationships", p. 946, col. 2.

*Chemical Abstracts*, vol. 116. No. 13 (1992), Kertscher et al., "PAF antagonists with phospholipidstructure. Part 1: Phospholipids with heteroarene heteroarene head groups: synthesis, characterizationand activity–determiningstructural requirements", p. 946, Col. 2.

(List continued on next page.)

*Primary Examiner*—Jane Fan
*Attorney, Agent, or Firm*—Webb Ziesenheim Bruening Logsdon Orkin & Hanson, P.C.

[57] ABSTRACT

The present invention describes novel cyclic diol derivatives represented by formula I and II:

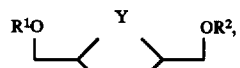

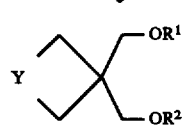

in which

Y represents O, S, SO, SO$_2$, (CH$_2$)$_m$ wherein m is zero or an integer of 1 to 5, or NR$^a$ group wherein R$^a$ is hydrogen, lower alkyl, lower alkoxycarbonyl, aryl, arylalkyl or acyl;

R$^1$ represents an alkyl or alkylcarbamoyl group;

R$^2$ represents a group having formula T—(CH$_2$)$_n$—V (X$^-$)q, wherein T refers to a simple covalent bond, a CO, PO$_3^-$, C(O)O, or CONR$^b$ group wherein R$^b$ is hydrogen, lower alkyl or acyl;

n refers to an integer of from 1 to 10;

V represents either (i) the group indicated by formula —$^+$NR$^5$R$^6$R$^7$ wherein R$^5$, R$^6$ and R$^7$ stands for identical or different lower alkyl group, or two or three of R$^5$, R$^6$ and R$^7$ taken together with the adjacent nitrogen form heterocyclic ammonio group, or (ii) the group indicated by the formula

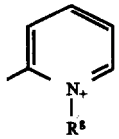

wherein R$^8$ represents lower alkyl group;

q is one or zero;

X$^-$ represents a pharmaceutically acceptable anion.

These compounds are potent PAF antagonists and thus useful for the treatment of the diseases in which PAF is involved.

8 Claims, No Drawings

OTHER PUBLICATIONS

*Chemical Abstracts*, vol. 116, No. 1 (1992), Okano et al., "Preparation of cyclohexanediol derivatives as platelet-activatingfactor (PAF) antagonists", p. 613, col. 1.

Matyas Koltai et al., "Platlet Activating Factor (PAF) A Review of its Effects... (Part I)", *Drugs* 42 (1) (1991), pp. 9–29.

Matyas Koltai et al., "PAF A Review of Its Effects... (Part II)", *Drugs* 42 (2) (1991), pp. 174–204.

Michael C. Venuti, "Platelet Activating Factor Receptors", *ComprehensiveMed. Chem.*, vol. 3 (1990) pp. 715–761.

Kelvin Cooper et al., "SAR of PAF Antagonists", *Annual Reports in Medicinal Chemistry*, vol. 24, Chapter 9 (1989), pp. 81–90.

CA 73: 87792 Beiezin 1970.

*The Journal of Experimental Medicine*, vol. 136 (1972), Jaques Benveniste et al., "Leukocyte–Dependent Histamine Release From Rabbit Platelets", pp. 1356–1377.

CA 107: 39243 Gautam et al. 1986.

CYCLIC LIPID DERIVATIVES AS POTENT PAF ANTAGONISTS

This is a continuation of application Ser. No. 08/193,163 filed on Feb. 10, 1994 now abandoned.

FIELD OF INVENTION

The present invention is to provide a series of novel cyclic diol derivatives having a potent antagonistic activity of the platelet activating factor(PAF), together with a process for their preparation. The invention also relates to their use in the treatment of the diseases in which PAF is involved.

BRIEF DESCRIPTION OF THE PRIOR ART

The platelet activating factor (PAF, 1-O-alkyl-2-acetyl-sn-glyceryl-3-phosphocholine) is a potent endogenous phospholipid found in a variety of cells implicated in inflammatory process, including platelets, neutrophils, basophils, eosinophils, macrophages, mast cells and endothelial cells, and several tissues (heart, lung, kidney) of organism [Venuti, M. C., in "*Comprehensive Med. Chem.*, Ed. Hansch C., Pergamon Press, Oxford, 1990, vol 3, P 715].

PAF was recognized for the first time as a potent platetet aggregating agent[Benveniste, J. et al., *J. Exp. Med.*, 1972, 136] and it was found later to have a wide spectrum of biological activities such as constriction of smooth muscle, decrease of coronary blood flow, inhibition of cardiac effect, increase of vascular permeability or hypotension via interaction with specific receptors[Cooper, K. et al., *Annu. Rep. Med. Chem.* 1989, 24, 81]. Although the precise role of PAF in vivo is still not fully understood, PAF has been implicated as a potential mediator in a number of pathophysiological conditions such as asthma, inflammation, septic shock, thrombosis, gastric ulceration, transplant rejection, hypotension, and ischemic heart disease[Koltai et al., *Drugs*, 1991, 42(2), 9 & 174].

These facts suggest that a specific potent PAF antagonist may prove useful in the treatment of these diseases related directly or indirectly with PAF. A number of potent, structurally diverse classes of PAF antagonists have been reported. In particular, natural PAF-like lipid compounds disclosed in patents. Japanese Laid-Open Patent No. Sho 60-104066, EP 327962, EP 353474, U.S. Pat. No. 4,851,450, U.S. Pat. No. 4,891,363, U.S. Pat. No 4,940,706, U.S. Pat. No. 4,945,098, and U.S. Pat. No. 4,997,843 are among them.

However, very few of these compounds are satisfactory due to some problems associated with selectivity, potency and bioavailability, the three properties which are essential for the clinical development of a PAF antagonist. Under these circumstances, the inventors have long made intense investigations for the purpose of finding novel compounds which are better than the known PAF antagonists in these properties.

DETAILED DESCRIPTION OF THE INVENTION

The invention described and claimed herein encompasses compounds represented by the formula I or pharmaceutically acceptable salts thereof:

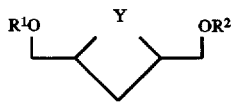

in which:

Y represents a divalent group selected from the class consisting of O, S, SO, $SO_2$, $(CH_2)_m$ wherein m is zero or an integer of 1 to 5, and $NR^a$ group wherein $R^a$ is hydrogen, lower alkyl, lower alkoxycarbonyl, aryl, arylalkyl, or acyl;

$R^1$ represents either an alkyl, alkenyl or alkynyl group, of 10 to 24 carbon atoms or a $CONR^3R^4$ group, wherein $R^3$ is hydrogen or lower alkyl and $R^4$ is an alkyl, alkenyl or alkynyl group, of 10 to 24 carbon atoms;

$R^2$ represents a group having formula T—$(CH_2)_n$—V $(X^-)q$, wherein T refers a simple covalent linkage, or a CO, $PO_3^-$; C(O)O, or $CONR^b$ group wherein $R^b$ is hydrogen, lower alkyl or acyl;

n refers to an integer of from 1 to 10;

V refers to either (i) the group indicated by formula —$NR^5R^6R^7$ wherein $R^5$, $R^6$, and $R^7$ stand for identical or different lower alkyl group, or two or three of $R^5$, $R^6$ and $R^7$ taken together with the adjacent nitrogen form heterocyclic ammonio group, or ii) the group indicated by the formula

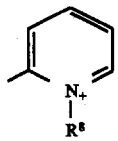

wherein $R^8$ represents lower alkyl group;

q is one or zero;

$X^-$ represents a pharmaceutically acceptable anion such as halide(chloride, bromide, or iodide), lower alkyl sulfonate, arylsulfonate, carboxylate, sulfate, nitrate, or phosphate.

The present invention is also to provide another class of cyclic glycol derivatives represented by the formula II or pharmaceutically acceptable salts thereof:

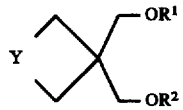

in which Y, $R^1$, and $R^2$ are of same meanings as defined above in the formula I.

The following definitions are given for various terms used throughout this specification. The term "alkyl group" in the definition of $R^1$, $R^3$ and $R^4$ refers to straight or branched $C_6$–$C_{24}$ alkyl which may have a double bond or triple bond. Preferably it refers to a $C_{10}$–$C_{24}$alkyl group. Examples of such alkyl groups include the decyl, undecyl, tridecyl, tetradecyl, pentadecyl, hexadecyl, heptadecyl, octadecyl; nanodecyl, icosyl, henicosyl, dococyl, tricocyl and tetracosyl groups.

The term "lower alkyl group" in the definition of $R^a$, $R^3$, $R^4$, $R^5$, $R^6$, $R^7$, and $R^8$ refers to straight or branched $C_1$ to $C_6$ alkyl. Examples of such alkyl groups include the methyl, ethyl, n-propyl, isopropyl, n-butyl, isobutyl, tert-butyl, n-pentyl, and n-hexyl groups, of which the methyl, ethyl, and propyl groups are preferred.

The term "lower alkoxycarbonyl group" in the definition of $R^8$ refers to lower carboalkoxy group derived from the lower alkoxy groups whose carbon number ranges from 1 to 4, such as methoxy, ethoxy, propoxy, or butoxy group.

The term "aryl group" in the definition of $R^a$ refers to substituted or unsubstituted phenyl or naphthyl group.

Where they are substituted, the substituents include, for example, halogen atoms, $C_1$–$C_4$ alkyl groups, such as methyl, ethyl, propyl and butyl, $C_1$–$C_4$ alkoxy, and $C_1$–$C_4$ haloalkyl.

The term "arylalkyl group" in the definition of $R^a$ refers to arylalkyl group derived from the above-described aryl group. The alkyl part is preferably a $C_1$ to $C_4$ alkyl group. Examples of such arylakyl groups include the benzyl, phenethyl, phenylpropyl, and 1- or 2-naphthylmethyl groups, of which the benzyl group is preferred. Such preferred groups may, if desired, be substituted as defined above.

The term "acyl group" in the definition of $R^a$ and $R^b$ refers to the residues of organic acids such as aliphatic saturated carboxylic acids, aliphatic unsaturated carboxylic acids, carbocyclic carboxylic acids and heterocyclic carboxylic acids. They include lower alkanoyl groups, aroyl groups, heteroaroyl groups, and lower cycloalkylcarbonyl groups. Examples of the lower alkanoyl groups include the formyl, acetyl, propionyl, butyryl, isobutyryl, valeryl, isovaleryl and pivaloyl groups. Examples of the aroyl groups include the benzoyl and naphthoyl groups which may contain one or more substitutents as defined above. Examples of the heteroaroyl groups include the furoyl, nicotinyl and isonicotinyl groups. Examples of the lower cycloalkylcarbonyl groups include cycloalkylcarbonyl groups in which number of carbon ranges from 4 to 7, such as cyclopropylcarbonyl, cyclobutylcarbonyl, cyclopentylcarbonyl, and cyclohexylcarbonyl. Among them, preferred are the lower alkanoyl groups such as acetyl, propionyl and butyryl, and the benzoyl group unsubstituted or substituted by one or more substituents as defined above.

The term "heterocyclic ammonio group" in the definition of $-{}^+NR^5R^6R^7$ refers to 5 to 6 membered mono-, bi-, tri-cyclic ammonio groups connected directly to the methylene group by the nitrogen atom of the ring, which may contain additional hetero atoms selected from sulfur, nitrogen and oxygen. They may be aromatic or partly or wholly saturated and may optionally be substituted by lower alkyl, $C_1$–$C_4$ alkoxy-1-halogen, or like. Examples of such heterocyclic ammonio group include N-methyl-1-pyrrolino, N-methyl-1-pyrrolidino, 3-oxazolino, 2-isoxazolino, 3-thiazolio, 4-methyl-3-thiazolio, 1-pyridinio, N-methyl-1-piperidinio, N-methyl-4-morpholio, 1-pyridmidinio, 1-pyrazinio, 3-benzothiazolio, 3-benzoxazolio, 1-quinolinio, 5,6,7,8-tetrahydro-1-quinolinio, 2-isoquinolinio, etc. Among them, preferred are the aromatic heterocyclic ammonio groups such as 3-thiazolio, 4-methyl-3-thiazolio, 1-pyridinio, 1-quinolinio, and 2-isoquinolinio.

If desired, the anion $X^-$ can be interchanged with another anion by ion exchange techniques, to afford other salts, all of which are considered part of the present invention.

The vast majority of the compounds of the present invention contain at least one asymmetric carbon atom so that they exist in various optical and diastereomeric stereoisomers. As a matter of course, all of individual isomer in pure form and in admixture, including racemic mixture, are within the scope of this invention.

The compounds of the formula I and II of this invention may exist in unsolvated as well as solvated forms, including hydrated forms. In general, the solvate forms, with pharmaceutically acceptable solvents such as water, ethanol or the like are equivalent to the unsolvated forms for purpose of the invention.

Although the present invention covers all the compounds mentioned above, the following compounds are more preferred:

Referring to the compound of the formula I,

Those compounds in which Y is an oxygen or sulfur atom, a methylene or $NR^a$ group wherein $R^a$ is lower alkyl, arylalkyl or acyl;

Those compounds in which $R^1$ is an alkyl group of $C_{14}$ to $C_{20}$ carbon atoms, and most preferably those in which $R^1$ is an alkyl group of $C_{16}$ to $C_{18}$ carbon atoms, that is, hexadecyl, heptadeyl, and octadecyl;

Those compounds in which $R^1$ is a $CONR^3R^4$ group wherein one of $R^3$ and $R^4$ is preferably hydrogen or methyl and the other group is an alkyl group of $C_{14}$ to $C_{20}$ carbon atoms, specially of $C_{16}$ to $C_{18}$ carbon atoms, that is, hexadecyl, heptadeyl, and octadecyl;

Those compounds in which $R^2$ is $T-(CH_2)_n-V$ wherein T is a simple covalent bond or CO group, n is an integer from 4 to 8, and V is the group indicated by the formula (i) $-{}^+NR^5R^6R^7$ which represents a heterocyclic ammonio group, especially an aromatic heterocyclic ammonio group selected from the class consisting of 3-thiazolio, 1-pyridinio, 1-quinolinio and 1-isoquinolinio group;

Those compounds in which $R^2$ is $T-(CH_2)_n-V$ wherein T is a $-CONR^b$ group, $R^b$ is an acetyl or benzoyl group unsubstituted or substituted by methoxy group, n is 1, V is the group indicated by the formula (ii) where $R^8$ is methyl, ethyl and propyl, and most desirable $R^8$ is ethyl.

Referring to the compound of the formula II preferred examples of Y includes an oxygen or sulfur atom, a $(CH_2)_m$ group wherein m is zero or an integer of 1 to 4, or $NR^a$ group wherein $R^a$ is lower alkyl, arylalkyl or acyl. Preferred examples of other symbols are the same as described above in the preferred compounds having the formula I.

The purpose of the present invention is also to provide methods to prepare compounds of the formula I.

The title compound I in which T is $CONR^b$ (wherein $R^b$ is hydrogen or acyl), V is the group of formula (i), and other symbols are of the same meanings as defined above, i.e. a compound of formula(IX), can be prepared from the starting compound (III), as shown in Scheme 1.

In step 1, one of the two hydroxyl groups present in the diol(III) is functionalized to provide the compound(IV) containing an alkyl or alkylcarbamoyl group represented by $R^1$. If an alkyl group as $R^1$ is desired, the diol(III) is treated with a slight excess of an inorganic base such as sodium hydride, potassium hydride or potassium hydroxide followed by an alkylating reagent, such as alkyl halide or an alkyl-or arylsulfonate. The reaction can be carried out in an aprotic solvent compatible with reagents, such as tetrahydrofuran, dimethylformamide, dimethyl sulfoxide, or toluene at the temperature ranging from room temperature to 100° C.

If an alkylcarbamoyl group as $R^1$ is desired, the diol(III) is reacted with an equivalent of the n-alkylisocyanate. The reaction can be accelerated by adding 0.1 equivalent of dibutyltin oxide as a catalyst in an aprotic solvent which does not interfere with reaction, such as tetrahydrofuran or diethyl ether. The reaction can be performed at temperature ranging from 0° C. to 60° C. Alternatively, this reaction can be carried out in the presence of a nitrogen-containing base such as pyridine or triethylamine, which can be used as solvent, if desired. The reaction temperature is suitably selected between room temperature and 100° C.

In step 2, A compound of the general formula(IV) is reacted with phenyl haloformate in the presence of a base to provide a compound of the general formula(V). As a suitable base, mention can be made of an inorganic base such as sodium hydride or potassium hydride and a nitrogen-containing organic base such as pyridine or triethylamine. The reaction is carried out without any solvent or with a solvent that does not interfere with the reaction, general formula(VII). This acylation step involves the use of a reactive derivative of a carboxylic acid having the formula $R^bOH$, where $R^b$ is acyl group, such as anhydride$(R^b)_2O$ or acid chloride$(R^bCl)$.

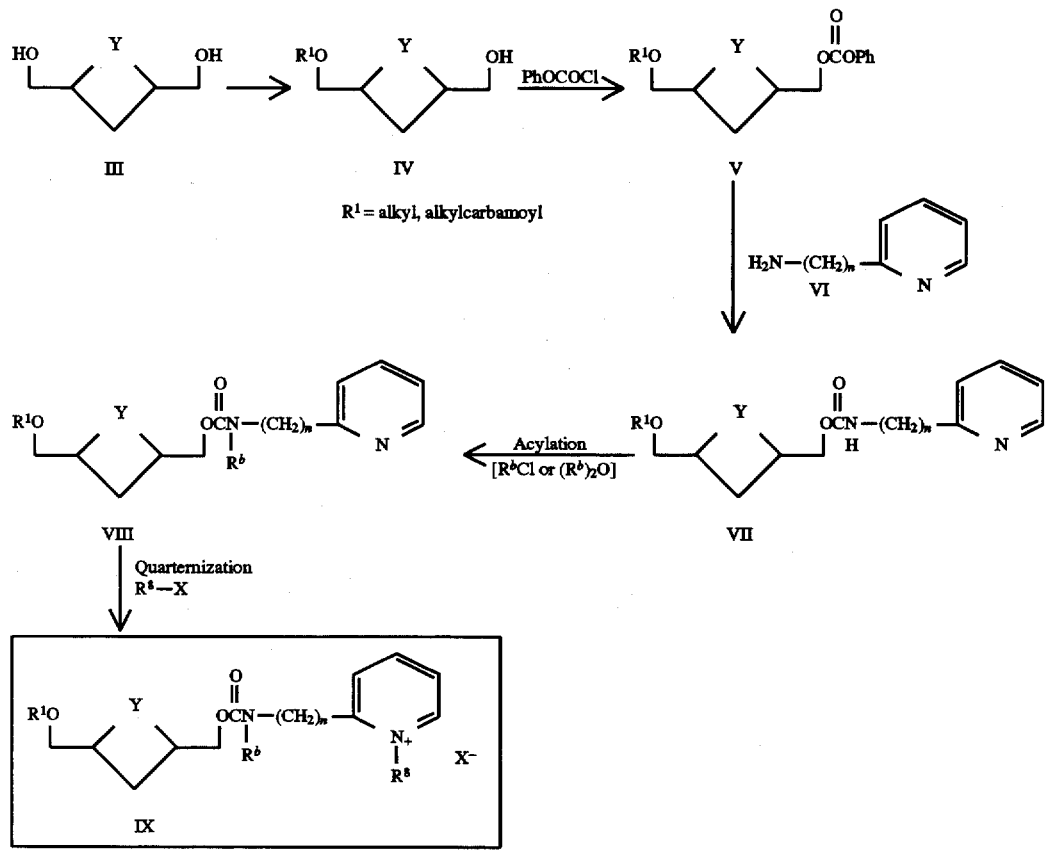

Scheme 1

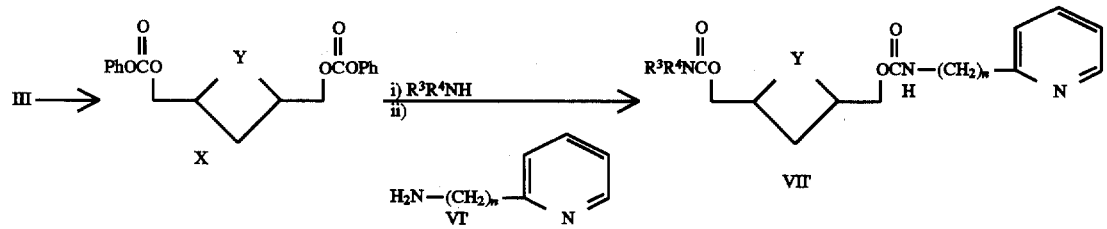

Scheme 1' such as, for example, methylene chloride, chloroform, benzene, tetrahydrofuran, or dioxane. The reaction temperature is suitably selected between 0° C. and the boiling point of the solvent, preferably between 0° C. and 30° C.

In step 3, a compound of the general formula(V) is treated with one equivalent of a primary amine having the general formula(VI) to give a compound of the general formula (VII). The reaction is performed in a solvent that does not interfere with the reaction. Among these are the chlorocarbon solvents such as chloroform or dichloromethane, the ethers such as tetrahydrofuran, diethyl ether, or dioxane, and aromatic solvents such as benzene or toluene. The reaction temperature is suitably selected between room temperature and the boiling point of the solvent, preferably between 50° C. and 90° C.

In step 4, a compound of general formula(VII) is acylated by a conventional method to provide a compound of the The reaction is preferably conducted in the presence of an organic base such as pyridine or triethylamine, which can be used as solvent, if desired. The reaction can be done in a solvent selected from the chlorocarbon solvents such as chloroform and methylene chloride or the aromatic solvents such as benzene and toluene at the temperature selected in the range of 0° C. to the boiling point of the solvent used.

In step 5, a compound of the general formula(VIII) is reacted with $R^8$—$X(R^8$ and X being as defined above) to obtain an intended product(IX) of the present invention. When X is a halide, $R^8$-Hal can be used. The reaction can be performed without any solvent or with a solvent that does not interfere with the reaction, such as acetonitrile, toluene, dimethyl formamide, etc. The reaction temperature is suitably selected in the range of 50° C. to 120° C. It is desirable that the reaction is done under argon atmosphere, while protected from light.

The intended products(IX) obtained are salts wherein the anion X⁻ comes from the reagent R⁸—X. If desired, this anion can be interchanged with another anion using ion exchange methods.

The intermediate compound having the formula(VII) where R¹ contains an alkylcarbamoyl group can be prepared by the alternative sequences, as shown in Scheme 1'. The reaction of (III)→(X) can be conducted under conditions similar to the case of (IV)→(V), but using two equivalents of phenyl chloroformate and a base. The conversion of (X) to (VII) can then be readily achieved by reacting the dicarbonate compound(X) with an equivalent of amine (R¹NH₂) followed by an equivalent of the compound having the formula (V) in the same reaction flask. This one-pot reaction can be conducted in an aprotic solvent such as toluene, chloroform, or dimethylformamide at the temperature ranging from 50° C. to 120° C.

The title compound of formula I in which T contains a CO group and V is the group indicated by the formula(ii)⁺ NR⁵R⁶R⁷(wherein R⁵, R⁶, R⁷ and other symbols are of the same meanings as defined above), i.e. a compound of formula(XII), can be prepared by following two step sequences starting from the compound(IV), as shown in Scheme 2.

In the first step, a compound of the general formula(IV) is acylated with a compound having the formula[(ClCO(CH₂)ₙ)] to obtain (XI) under conditions similar to that of (IV)→(V).

The second step involves a quaternization reaction which can be done by allowing(XI) to react with an excess amount of the tertiary amine having formula NR⁵R⁶N⁷. The reaction can be done without any solvent or with a suitable solvent such as acetonitrile, benzene or toluene at the temperature ranging between 50° C. and 120° C. It is desirable that the reaction is done under argon atmosphere, while shielded from light.

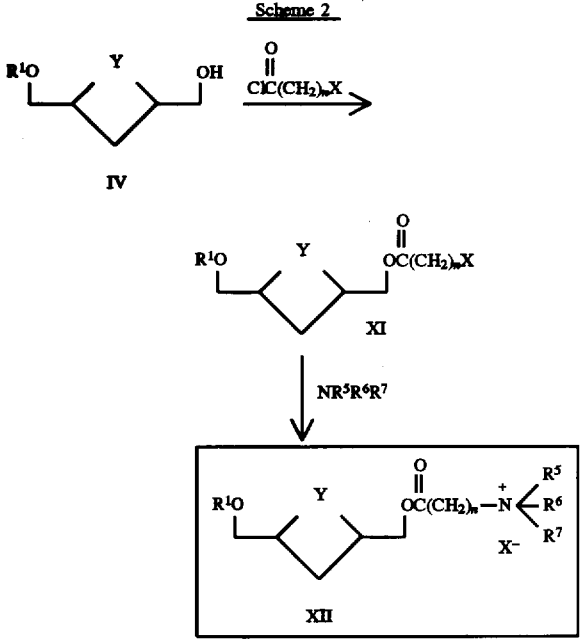

The intended compound of formula I in which T contains a PO₃⁻ group and V is the group indicated by the formula (ii)⁺NR⁵R⁶R⁷(wherein R⁵, R⁶, R⁷ and other symbols are of the same meanings as defined above), i.e. a compound of formula(XIV), can be prepared by following two step sequences starting from the compound(IV), as shown in Scheme 3.

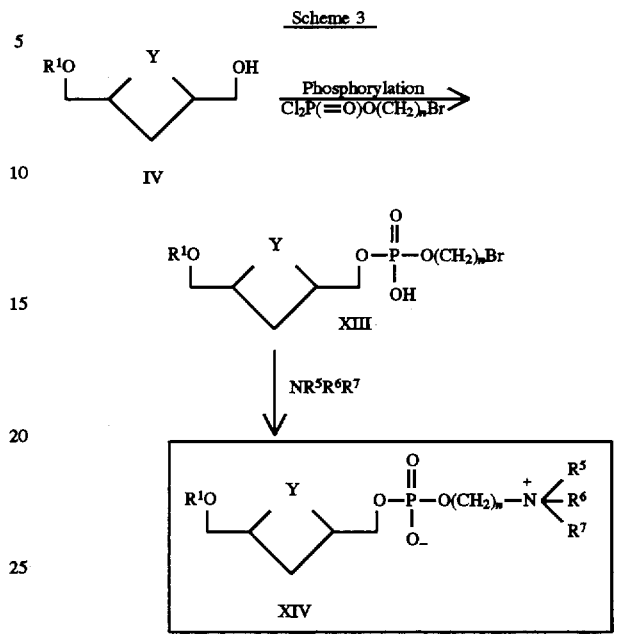

The first step is a phosphorylation reaction. A compound of the general formula(IV) is reacted with bromoalkyl phosphorodichloridate(Cl₂P(=O)O(CH₂)ₙBr), obtained by utilizing a method of the literature[Hirt, R. et al., Pharm. Acta Helv., 1958, 33, 349], This reaction can be done in the presence of a base such as triethylamine or pyridine at the temperature ranging from 0° C. to the boiling point of the solvent. As the preferable solvent, mention can be made of an aprotic solvent such as methylene chloride, chloroform, diethyl ether, tetrahydrofuran, benzene, or toluene. The compound (XIII) can then be produced by hydrolysis using pyridine or sodium acetate as a base in water at the temperature ranging from 20° C. to 70° C. A miscible co-solvent such as tetrahydrofuran or acetonitrile can be used, if desired.

The second step (XIII)→(XIV) involves a quaternization reaction which can be done by allowing (XIII) to react with the compound having formula NR⁵R⁶N⁷ under conditions similar to that of (XI)→(XII). The intended quaternary ammonium salt(XIV) is then obtained in a zwitterionic form by treating with silver carbonate in a suitable solvent such as acetonitrile, methanol, or tetrahydrofuran. The reaction temperature is suitably selected in the range between room temperature and the boiling point of the solvent.

The intended compound of formula I in which T is a simple covalent bond and V is the group indicated by the formula(ii) ⁺NR⁵R⁶R⁷(wherein R⁵, R⁶, R⁷ and other symbols are of the same meanings as defined above), i.e. a compound of formula(IVI), can be prepared by following two step sequences starting from the compound(IV), as shown in Scheme 4.

Scheme 4

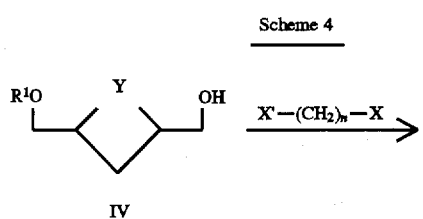

IV tion can be easily prepared by the process shown in Scheme 5, 6 and 7.

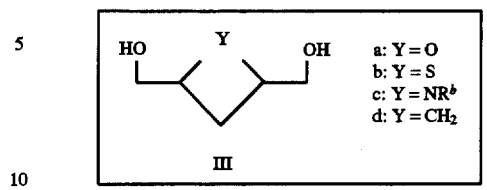

a: Y = O
b: Y = S
c: Y = NR$^b$
d: Y = CH$_2$

III

The compound (IIIa) in which Y of the formula (III) is an oxygen atom can be readily synthesized starting from the compound (XVII), obtained by the methods of literature [Walkup, R. D. et al., Tet. Lett., 1987, 28, 4019].

Scheme 5

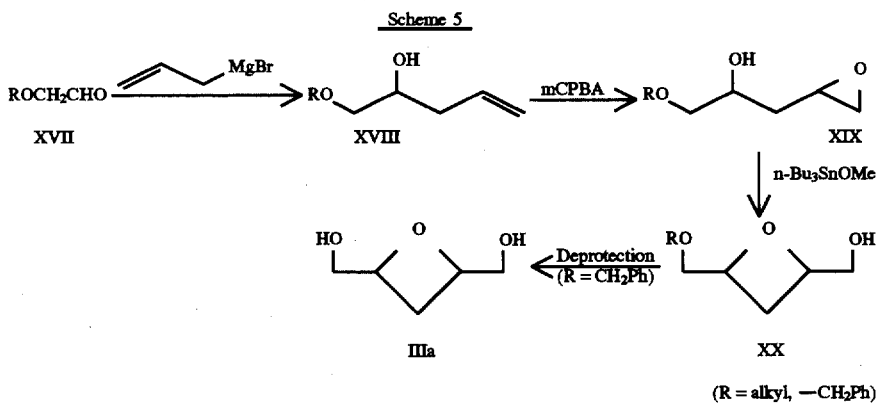

(R = alkyl, —CH$_2$Ph)

-continued
Scheme 4

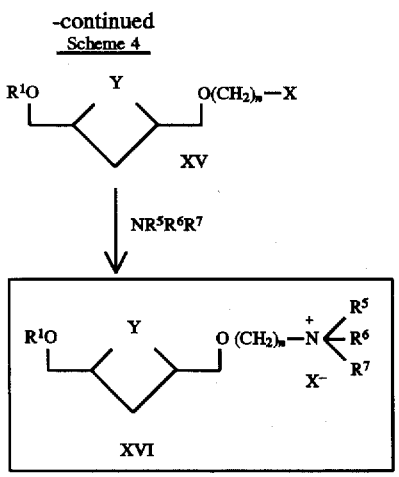

The first step involves a deprotonation reaction with a strong base, such as sodium hydride, followed by the alkylation reaction with X(CH$_2$)$_n$X', where X and n have the above meanings and X' is another suitable leaving group, such as bromide, iodide, alkyl or arylsulfonate, X' being a leaving group better than or equal to X.

The second step (XV)→(XVI) is a quarternization reaction which can be performed in a manner similar to (XI)→(XII).

The compound of the general formula(III) used as the intermediate compound in the process of the present inven- As shown in Scheme 5, the starting Compound (XVII) (wherein R denotes the above-defined alkyl group as R$^1$ or a benzyl group) is allowed to react with an equivalent of allylic magnesium bromide in an aprotic solvent such as tetrahydrofuran or ethyl ether at the temperature ranging from 0° C. to 50° C. to obtain the secondary alcohol (XVIII). Epoxidation reaction of (XVIII)→(XIX) can be carried out with perbenzoic acid such as m-chloroperbenzoic acid in a suitable solvent such as methylene chloride, chloroform or tetrahydrofuran at room temperature.

The ring-closure reaction of (XIX)→(XX) can then be performed by heating (XIX) in the presence of n-tributylin methoxide in accordance with the methods described in the literature [Bats. J. P. et al., *Tetrahedron*, 1982, 38, 2139]. The reaction can be done without any solvent or with a solvent that does not interfere with the reaction, such as toluene or benzene at the temperature ranging from 100° C. to 250° C. Where the oxetane compound(XX) contains a benzyl group for R, the benzyl group present in (XX) can be reductively removed under the typical hydrogenolysis conditions to produce the intended diol compound The palladium catalyst such as Pd(OH)$_2$ or Pd/C is used for this reduction under the pressure ranging from 1 atm to 50 atm. The reaction proceeds at the temperature ranging from 20° C. to 80° C. in a polar solvent such as methanol, ethanol, or ethyl acetate.

As shown in Scheme 6, the starting material (IIIb) in which Y of the formula (III) is sulfur can be prepared starting from the dibromo ester (XXI), as reported in the literature [Baldwin, J. et al., *J. Chem. Soc. Chem. Commun.*, 1985, 194].

Scheme 6

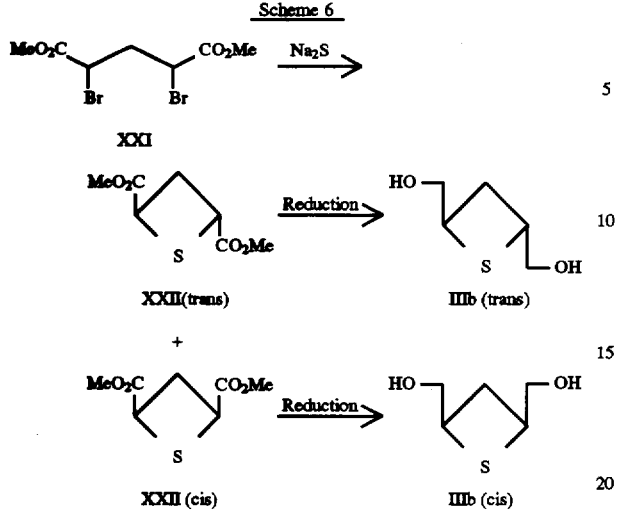

The thietane ring-forming reaction of (XXI) with one equivalent of sodium sulfide proceeds rapidly in a polar solvent such as dimethyl sulfoxide, methanol, or methylene chloride alone, or a mixture thereof to afford the thietane compound(XXII). The reaction can be performed at the temperature ranging from −78° C. to room temperature, preferably between −30° C. to 20° C. The compound (XXII) exists in a diastereometric mixture of the cis and trans isomers. If desired, each isomer can be separated in a pure form by a flash column chromatography. Reduction of the ester groups of (XXII) can be performed by a conventional method employing lithium aluminum hydride or lithium borohydride as a reducing agent in a suitable solvent such as tetrahydrofuran or ethyl ether to the diol compound (IIIb).

The starting material (IIIc') in which Y of the formula (III) is a NR$^a$ group(wherein R$^a$ is a lower alkyl, aryl or arylalkyl) can also be prepared from the dibromo ester compound (XXI) in two steps(Scheme 7).

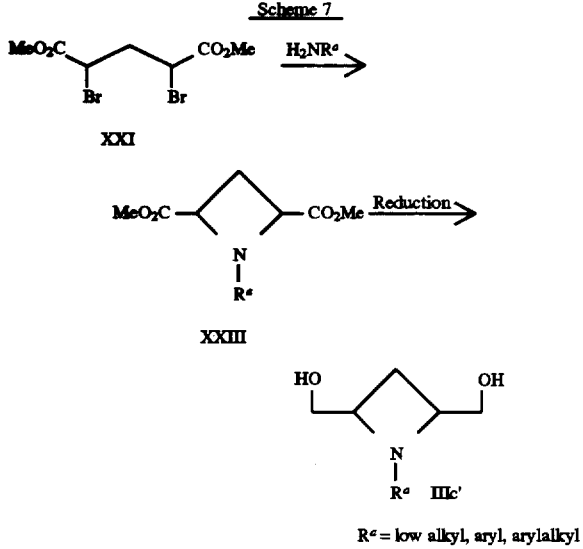

Scheme 7

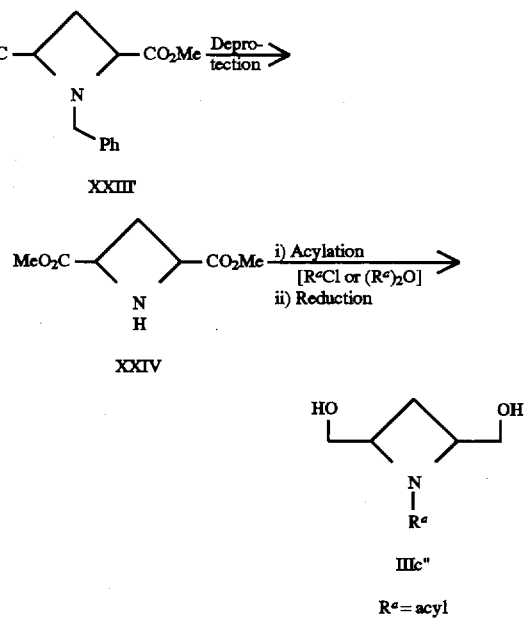

R$^a$ = acyl

The first reaction of (XXI)→(XXIII) can be carried out by subjecting the dibromo ester (XXI) to a primary amine (R$^a$NH$_2$). The reaction can be conducted in the presence of two equivalents of a base such as an inorganic base (e.g. sodium hydrogen carbonate, potassium carbonate) or a nitrogen-containing organic base such as pyridine or triethylamine. This reaction can also be performed conveniently without a base by using three equivalents of R$^a$NH$_2$, which can serve as solvent, if desired. As the reaction solvent, a mention can be made of a polar solvent such as acetonitrile, dimethyl formamide, chloroform, tetrahydrofuran, or toluene. The reaction temperature ranges from 0° C. to the boiling point of the solvent. If desired, the pure cis and trans isomers of the compound (XXIII) can be separated in pure forms by a flash chromatography.

The second step involves the reduction of diester group of (XXIII) to afford the diol compound(IIIc'). As the preferable reducing agent, mentioned can be lithium aluminum hydride or lithium borohydride. As the solvent, use is made of methanol, tetrahydrofuran, ethyl ether, etc., and the reaction proceeds at the temperature ranging from 0° C. to 50° C.

The starting compound (IIIc") in which Y of the formula (III) is a NR$^a$ group (wherein R$^a$ is acyl) can be derived from the compound (XXIII') containing a benzyl group for R$^a$. The reductive removal of the N-benzyl group of (XXIII) under similar conditions to those for (XX)→(IIIa) affords the compound(XXIV). The transformation of (XXIV)→ (IIIc") involves an N-acylation reaction followed by a reduction. By allowing (XXIV) to react with one equivalent of a reactive derivative of a carboxylic acid R$^a$ OH (wherein R$^a$ is acyl), such as acid chloride(R$^a$Cl) or acid anhydride (R$^a$)$_2$O as an acylating agent in the presence of a base, such as pyridine or triethylamine, the N-acylation of the azetidine compound(XXIV) can be achieved. As the reaction solvent, an aprotic solvent such as methylene chloride, acetonitrile, tetrahydrofuran, benzene, or toluene can be employed. The reaction temperature ranges from −20° C. to the boiling point of the solvent. The selective reduction of the ester functional group to the diol compound(IIc") can then be performed by treatment with a reducing reagent such as lithium borohydride in ethyl ether at room temperature.

The starting material (IIId) in which Y of the formula(III) is a methylene group can be readily prepared in a pure cis or trans form by lithium aluminum hydride reduction of its corresponding diester compound, which is disclosed in the literature[Allinger N. L. et al., *J. Org. Chem.*, 1965, 30, 1945].

The purpose of this invention is also to provide the compound having the general formula II wherein Y, $R^1$, and $R^2$ are of the same meanings as defined above.

They can be easily produced by the same synthetic sequences employed for the preparation of the compound of formula I, but utilizing the compound (XXV) instead of the compound (III) as the starting material.

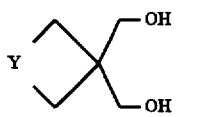

a: Y = O
b: Y = S
c: Y = $NR^b$
d: Y = $CH_2$

The starting compounds (XXVa) and (XXVd), in which Y of the formula (XXV) is an oxygen atom and a $(CH_2)_n$ group respectively, can be synthesized by utilizing compounds known in the literature or by modified methods of the following literature[e.g. Issidorides, C. H. et al., *J. Am. Chem. Soc.*, 1955, 77, 6382; Picard, P. et al., *Synthesis*, 1981, 551; Mariella, P., *Org. Synthesis*, 1966, Coll. vol 4, 288; Mandolini, L. et al., *J. Org. Chem.*, 1981, 46, 3127], as shown in Scheme 8.

The starting compound (XXVb) in which Y of the formula (XXV) is sulfur can be prepared from 2,2-Bis-(bromomethyl)-1,3-propanediol(XXVI) in three steps, as shown in Scheme 9.

Scheme 9

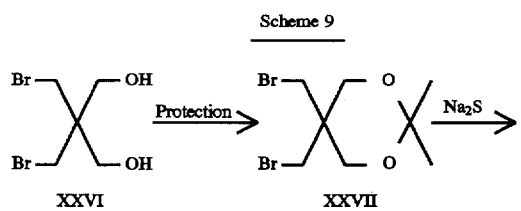

-continued
Scheme 9

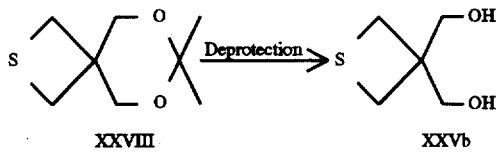

After protection of the diol functional group present in the compound(XXVI) as acetonide utilizing the conventional methods, the thietane ring-forming reaction of (XXVII) to (XXVIII) can be done by treatment with sodium sulfide in a polar solvent such as dimethyl sulfoxide or methanol at the temperature ranging from 0° C. to 50° C. The desired diol compound (XXVb) is then obtained by deprotection of the acetonide protecting group under acidic conditions.

The starting compound (XXVc') in which Y of the formula(XXV) is a $NR^a$ group (wherein $R^a$ is a lower alkyl, aryl or arylalkyl) can be prepared from (XXVII) in two steps, as shown in Scheme 10.

Scheme 10

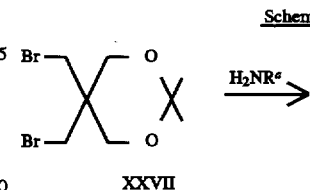

XXVII

Scheme 8

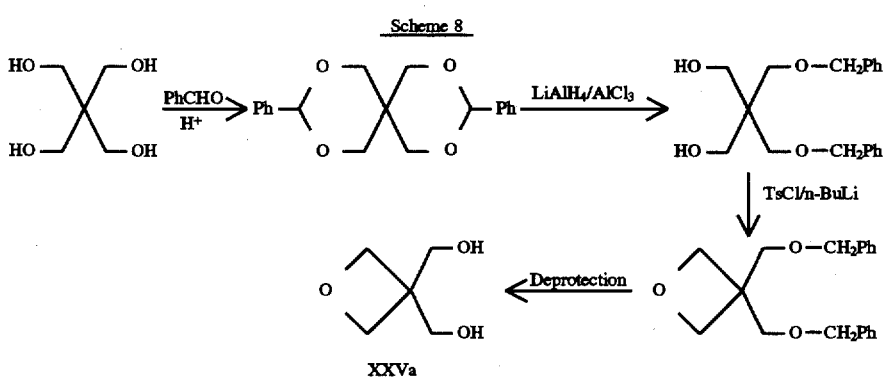

-continued
Scheme 10

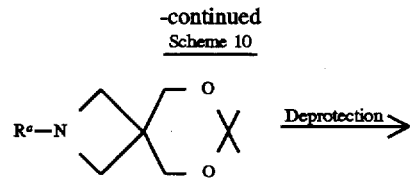

XXIX

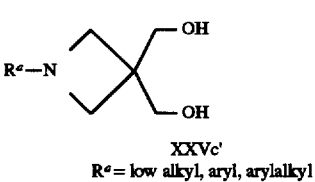

XXVc'
$R^a$ = low alkyl, aryl, arylalkyl

-continued
Scheme 10

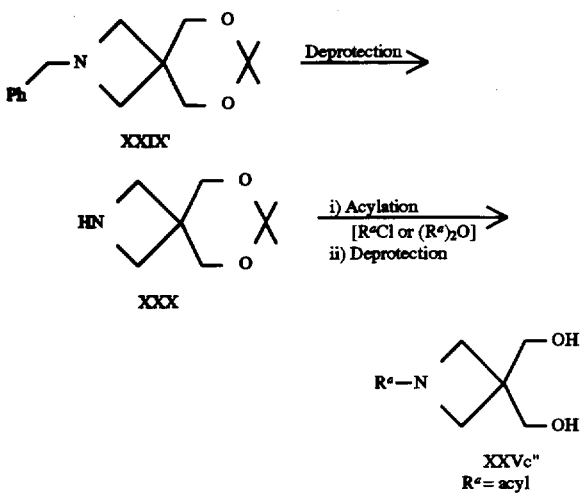

XXIXʹ

XXX

XXVcʺ
Rᵃ = acyl

The first azetidine ring-forming reaction (XXVII)→(XXIX) can be conducted in a manner similar to that of (XXI)→(XXIII).

The second step involves deprotection of the acetonide protecting group present in compound(XXIX) to produce the desired compound (XXVcʹ)

To prepare the starting compound (XXVcʺ) in which Y of the formula(XXV) is a $NR^a$ group(wherein $R^a$ is acyl), the compound(XXIXʹ) having a benzyl group for $R^a$ is subjected to the catalytic hydrogenation conditions similar to those for (XXIIIʹ)→(XXIV). The N-acylation reaction of (XXX) under conditions similar to the case of (XXIV)→(IIIʺ) followed by the deprotection reaction of the acetonide protecting group affords the did compound(XXVcʺ).

As mentioned before, the starting compound having the general formula (XXV), i.e. (XXVa), (XXVb), (XXVcʹ), (XXVcʺ), (XXVd), can readily be convened to the title compound having the general formula II by employing the same general synthetic sequences presented above in Scheme 1-4. For the simplicity of the exposition, the preparation of the title compound II starting from the compound of formula(XXV) is not presented here but will be described in detail in Working Examples.

The title compounds I and II of the present invention exhibit excellent platelet activating factor(PAF) antagonistic activities, and are thus useful as prophylactic and therapeutic agents for circulatory disturbances due to PAF, for example, thrombosis, apoplexy (e.g. cerebral hemorrhage, cerebral thrombosis), myocardial infarction, angina pectoris, venus thrombosis, nephritis, diabetic nephritides, shock(e.g. endotoxin shock, observed after grave infectious diseases or surgical operation, intravascular hemagglutination syndrome caused by endotoxin, anaphylactic shock, hemorrhagic shock). The title compounds I and II are also useful for the treatment of diseases associated with allergy and inflammation(e.g. bronchial asthma, psoriasis), gastroentric diseases caused by PAF(e.g. gastric ulcer), pneumonia, rejection symptoms associated with increase in the mount of PAF produced in the case of internal organ transplantation, insufficiency of internal organ(e.g. heart, kidney, liver) in the case of internal organ operation, ischemic cerebral and cardiac diseases, and renal disorders.

The PAF antagonistic properties of the title compounds I and II can be demonstrated by their ability to displace [³H]PAF from its binding sites in rabbit platelets and to inhibit PAF-mediated effects, such as rabbit platelet aggregation and serotonin release. The following pharmacological test examples explain the effects of the present invention in a more concrete manner.

TEST EXAMPLE I

Inhibitory action on PAF-induced [$^{14}$C]-serotonin release

Blood was collected from the hearts of conscious New Zealand white male rabbits weighing 2 to 3 kg. The blood was immediately subjected to a centrifuge at 1400 rpm for 10 minutes to obtain platelet rich plasma(PRP). PRP was incubated with a trace amount of [$^{14}$C]-serotonin for 20 minutes at 22° C. Prelabelled platelets were prepared by centrifugation at 3500 rpm for 10 minutes. The test compound was added to 80 μl of [$^{14}$C]serotonin-labeled platelets in plastic test tubes, and the mixture was incubated for 2 minutes. PAF (1×10$^{-9}$M) was then added to the reaction mixture and incubated for additional 2 minutes at which time 10 μl of cold formaldehyde was added to stop the reactions. The tubes were immediately cooled to 4° C. and centrifuged at 12000 rpm for 2 minutes. The supernatants (80 μl) were assayed for percentage of [$^{14}$C]serotonin release by the conventional methods of measuring $^{14}$C counts. The test results are shown in Table 1.

TABLE 1

| Test Compound Working Ex. No | Inibition % Concentration of Test Compound | | |
|---|---|---|---|
| | $2 \times 10^{-7}$M | $5 \times 10^{-8}$M | $5 \times 10^{-9}$M |
| 1 | 90% | 51% | |
| 2 | 98% | 93% | 44% |
| 3 | 97% | 85% | 58% |
| 5 | 97% | 95% | 70% |
| 6 | 98% | 96% | 75% |
| 10 | 86% | 43% | |
| 12 | 94% | 58% | |
| 13 | 92% | 85% | |
| 14 | 99% | 98% | 18% |

TEST EXAMPLE

Inhibitory action on PAF-induced platelet aggregation

Blood was collected from the hearts of conscious New Zealand male rabbits weighing 2 to 3 kg using citric acid as an anticoagulant (one volume part of 3% citric acid relative to 9 volume parts of the whole blood). A platelet-rich plasma(PRP) was prepared by centrifugation at 1000 rpm for 10 minutes. The remaining blood after collecting the PRP was subjected to a centrifuge at 3000 rpm for 10 minutes to obtain platelet poor plasma(PPP). PRP was diluted with PPP to adjust the number of platelets to about $3 \times 10^5$/μl. Solution of test compound (30 μl) was added to the PRP(270 μl), and after incubation for 2 minutes at 37° C., 30 μl aliquot of PAF($5 \times 10^{-9}$M) was added. Platelet aggregation was then examined by means of turbidimetry [Born, Nature, 194, 927(1962)] with dual channel aggregometer (Chrono-Log. Corp., Havertown, Pa.). As the control, physiological saline without test sample was used. The platelet aggregation inhibiting activities of the test sample are expressed as $IC_{50}$, that is the concentration of the compound at which 50% of the aggregation is inhibited. The test results are shown in Table 2.

TEST EXAMPLE III

PAF Receptor Binding Assay

Citrated whole rabbit blood was obtained from Pel-Freez (Rogers, AR). Rabbit platelets were prepared by centrifugation and washing. The platelets were lysed by freeze-thawing and sonification; Platelet membranes were prepared by centrifugation and washing. Final membrane preparation were stored frozen in 10 mM Tris/5 mM $MgCl_2$/2 mM EDTA (TME buffer, pH 7.0) with 0.25M sucrose added for membrane stabilization.

The standard PAF receptor binding assay contained 10 μg platelet membrane protein, 0.6 nM $[^3H]C_{18}$-PAF(from Amersham or New England Nuclear, specific activity 120–1800 Ci/mmol) ±test compound, in "binding buffer" consisting of TME with 0.25% bovine serume albumin added(Sigma, RIA grade). The final volume of the assay was 1001 μl. The assay was conducted in Millititer-GV™ (Millipore Corp.) filtration plates; incubation time was for 60 minutes at room temperature (22°–23° C.).

"Specific binding" was operationally defined as the arithmetic difference between "total binding" of 0.6 nM. $[^3H]C_{18}$-PAF(in the absence of added PAF) and "nonspecific binding" (in the presence of 1 μM PAF). After the prescribed incubation, platelet membranes were filtered under vacuum and washed with 1 ml of ice cold "binding buffer". The filters were dried and removed. The bound radioactivity was quantiated with a Berthold TLC-Linear Analyzer model LB2842. Dose-response curves of inhibition of specific $[^3H]C_{18}$-PAF binding by test compounds were conducted in duplicated, with at least four doses covering the active range. Experiments were repeated at least once. $IC_{50}$ values (concentration producing 50% inhibition) were determined by linear regression evaluation. Ki values of inhibitory binding constants were calculated according to the methods of the literature[Cheng et al., Biochem. Pharmacol., 1973, 22, 3099] whereby $Ki=IC_{50}/(1+([^3H]PAF]/Kd[^3H]PAF)=IC_{50}/(1+(0.6\ nM/0.6\ nM)=IC_{50}/2$.

TABLE 2

| Test compound Working Ex. No. | $IC_{50}$ (μM) | Test compound Working Ex. No. | $IC_{50}$ (μM) |
| --- | --- | --- | --- |
| 1 | 0.095 | 2 | 0.057 |
| 3 | 0.097 | 4 | 0.101 |
| 5 | 0.057 | 6 | 0.123 |
| 7 | 0.158 | 8 | 0.093 |
| 9 | 0.219 | 12 | 0.684 |
| 13 | 0.382 | 14 | 0.118 |
| 15 | 0.394 | 16 | 0.573 |
| 17 | 0.286 | 18 | 0.365 |
| 19 | 0.056 | 20 | 0.350 |
| 21 | 1.45 | 22 | 1.14 |
| 23 | 0.095 | 24 | 1.27 |
| 27 | 0.057 | 28 | 0.061 |
| 29 | 0.021 | 30 | 0.084 |
| 31 | 0.069 | 32 | 0.052 |
| 33 | 0.019 | 34 | 0.350 |
| 35 | 0.275 | 37 | 0.125 |
| 38 | 0.178 | 39 | 0.228 |
| 40 | 0.270 | 41 | 0.057 |
| 42 | 0.658 | 43 | 0.029 |
| 44 | 0.138 | 47 | 0.188 |

TABLE 3

| Test compound Working Ex. No. | Ki (nM) | Test compound Working Ex. No. | Ki (nM) |
| --- | --- | --- | --- |
| 1 | 21.2 | 2 | 14.7 |
| 3 | 9.2 | 4 | 15 |
| 5 | 5.7 | 6 | 22.6 |
| 7 | 20 | 8 | 95 |
| 9 | 110 | 12 | 188 |
| 13 | 30.5 | 14 | 6.6 |
| 15 | 13.0 | 16 | 3.8 |
| 17 | 56 | 18 | 110 |
| 19 | 4.3 | 20 | 1.2 |
| 21 | 112 | 23 | 9.4 |
| 27 | 4.3 | 28 | 9.8 |
| 29 | 9.8 | 30 | 34 |
| 31 | 26 | 32 | 20 |
| 33 | 99 | 37 | 9.3 |
| 38 | 278 | 39 | 20 |
| 40 | 28 | 41 | 30 |
| 43 | 35 | 44 | 104 |

[WORKING EXAMPLES]

The following typical working examples will further illustrate the present invention, which by no means limit the invention. Properties of each working example are listed at the end of each procedure.

Example 1 cis-2-[[N-Acetyl-N-[[[2-[(hexadecyloxy)methyl]-4-oxetanyl]methoxy]carbonyl]amino]methyl]-1-ethyl-pyridinium iodide

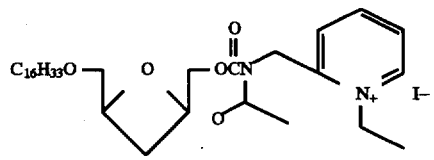

(a) 1-(hexadecyloxy)-4-penten-2-ol

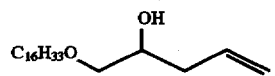

To a cold(0° C.) stirred solution of allyl magnesium bromide (10 ml, 1.0M solution in diethyl ether) in dry ethyl ether(50 ml) was added dropwise n-hexadecyloxy aldehyde (1.82 g) in dry ethyl ether(5 ml). The mixture was then heated at reflux for 1 h. The reaction was quenched by the addition saturated ammonium chloride aqueous solution. The organic layer was washed with brine, dried over anhydrous magnesium sulfate, and concentrated under reduced pressure. The resulting residue was purified by flash chromatography on silica gel (ethyl acetate:hexane=1:10) to afford 1.92 g of the desired product as a white solid (92% yield).

$^1$H-NMR(300 MHz, $CDCl_3$): δ0.97 (t, 3H, J=6.5 Hz), 1.20–1.60 (m, 26H ), 2.22–2.27(m, 2H), 2.30(d, 1H, J=3.5 Hz), 3.27(dd, 1H, J=9.7 Hz, J=7.5 Hz), 3.38–3.51(m, 5H), 3.80–3.85(m, 1H), 5.05–5.15(m, 2H), 5.88(m, 1H)

(b) 1-(hexadecyloxy)-4,5-epoxy-penten-2-ol

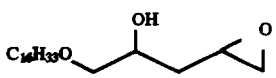

To a stirred solution of the compound prepared in example 1a (1.60 g) in methylene chloride (50 ml) was added 50–60% m-chloroperbenzoic acid (1.69 g) at 0° C., and the mixture was stirred for 12 h at room temperature. The reaction mixture was then washed successively with brine, 10% sodium bicarbonate solution and water. The organic layer was dried, concentrated under reduced pressure, and the resulting residue purified by flash chromatography on silica gel (ethyl acetate:hexane=1:5) to afford 1.41 g of the desired product (84% yield).

$^1$H-NMR(300 MHz, CDCl$_3$): δ0.88(t, 3H, J=6.4 Hz), 1.20–1.90(m, 29H), 2.59–2.63(m, 2H), 2.76–2.83(m, 1H), 3.05–3.15(m, 1H), 3.30–3.50(m, 5H), 3.95–4.05(m, 1H)

(c) cis,trans-4-[(Hexadecyloxy)methyl]oxetane-2-methanol

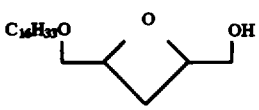

A mixture of the compound prepared in example 1b (316 mg) and tri-n-butyltin methoxide (0.28 ml) was heated at 120° C. under reduced pressure (20 mmHg) for 1 h. The mixture was then heated at 220° C. for 2 h under argon atmosphere. After cooling to room temperature, the reaction mixture was poured into the saturated ammonium chloride solution and extracted with ethyl acetate. The organic layer was dried, concentrated under reduced pressure and the resulting residue purified by flash chromatography on silica gel (ethyl acetate:hexane=1:3) to afford 101 mg of the desired product as a ca. 1:1 mixture of the cis and trans isomers as a colorless solid(32% yield).

mp: 34.6°–35.2° C.

$^1$H-NMR(300 MHz, CDCl$_3$): δ0.88(m, 3H), 1.20–1.65(m, 27H), 2.16–2.95(m, 2H), 3.42–3.81(m, 8H), 4.74–4.85(m, 2H)

IR(KBr):3386, 2925, 2851, 1487, 1376, 1109, 899, 849, 721 cm$^{-1}$

Mass(EI, m/z):343(M$^+$+1)

(d) cis, trans-2-[[N-[[[4-[(Hexadecyloxy)methyl]-2-oxetanyl]methoxy]carbonyl]amino]methyl]pyridine

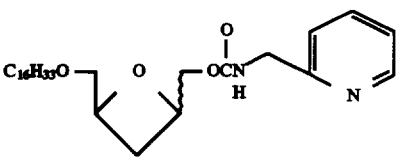

To a cold(0° C.) stirred solution of the compound prepared in example 1c (277 mg) in methylene chloride(15 ml) was added pyridine (0.13 ml) and then phenyl chloroformate (0.12 ml). After stirring at room temperature for 1 h, the reaction mixture was poured into the saturated ammonium chloride(10 ml). The organic phase was washed with 10% sodium bicarbonate, dried, and concentrated under reduced pressure. The resulting residue was dissolved in benzene(5 ml) containing 2-picolyl amine(104 mg), and the mixture was heated at reflux overnight. After cooling to room temperature, the reaction mixture was diluted with ethyl acetate, washed successively with 1N-HCl solution and water. The organic layer was dried, concentrated under reduced pressure, and the resulting residue purified by flash chromatography on silica gel (ethyl acetate:hexane=1:1) to afford 377 mg of the desired product as a ca. 1:1 mixture of the cis- and trans isomers as a colorless solid(85% yield).

$^1$H-NMR(300 MHz, CDCl$_3$): δ0.85–0.94(m, 3H), 1.20–1.60(m, 26H), 2.30–260(m,2H), 3.44–3.66(m, 4H), 4.25(d, 1H, J=4.7 Hz), 4.29(d, 1H, J=4.4 Hz), 4.50(d, 2H, J=5.5 Hz), 4.60–4.90(m, 2H), 5.85–6.05(m, 1H), 7.16–7.21 (m, 1H), 7.26–7.29(m, 1H), 7.66(t, 1H, J=7.7 Hz), 8.53(d, 1H, J=4.7 Hz)

IR(KBr): 3311, 2921, 2851, 1691, 1550, 1466, 1283, 1122, 1033, 992, 858, 753 cm$^{-1}$ (e) cis-2-[[N-Acetyl-N-[[[4-[(hexadecyloxy)methyl]-2-oxetanyl]methoxy]carbonyl]amino]methyl]pyridine and its trans isomer

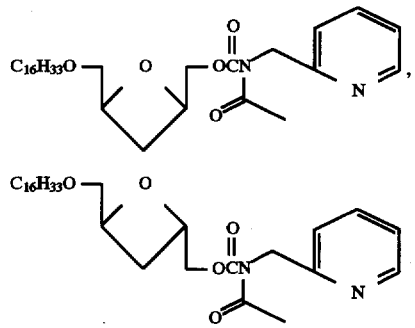

A mixture of the compound prepared in example 1d (84 mg) and acetic anhydride(0.25 ml) was heated at 110° C. in the presence of pyridine(0.35 ml) for 4 h. The mixture was then diluted with methylene chloride(20 ml), washed with 1N-HCl solution and then 10% sodium bicarbonate solution. The organic layer was dried, concentrated under reduced pressure and the resulting residue purified by flash chromatography on silica gel (ethyl acetate:hexane=1:3) to afford 36 mg of the pure cis isomer and 38 mg of the pure trans isomer(79% overall yield).

cis isomer; $^1$H-NMR(300 MHz, CDCl$_3$): δ0.88 (t, 3H, J=6.9 Hz), 1.15–1.62(m, 28H), 2.18–2.27(m, 1H), 2.40–2.55 (m, 1H), 2.62(s, 3H), 3.39–3.49(m, 4H), 4.24–4.37(m, 2H), 4.76–4.82(m, 2H), 5.11(s, 2H), 7.13(d, 2H, J=7.3 Hz), 7.61(t, 1H, J=7.9 Hz), 8.49(d, 1H, J=5.4 Hz)

IR(KBr):2922, 2850, 1736, 1705, 1466, 1370, 1216, 1123, 970 cm$^{-1}$ trans isomer; $^1$H-NMR(300 MHz, CDCl$_3$): δ0.88 (t, 3H, J=6.9 Hz), 1.15–1.62(m, 28H), 2.23–2.30(m, 1H), 2.40–2.50 (m, 1H), 2.64(s, 3H), 3.41–3.51(m, 4H), 424–4.37(m, 2H), 4.49–4.54(m, 1H), 4.75–4.77(m, 1H), 5.14(s, 2H), 7.12(d, 2H, J=7.8 Hz), 7.60(t, 1H, J=7.6 Hz), 8.49(d, 1H, J=3.2 Hz)

IR(KBr):2924, 2852, 1744, 1703, 1444, 1362, 1213, 1101, 981, 763 cm$^{-1}$ (f) Preparation of the title compound of this example A mixture of the cis compound isolated in example 1e (20 mg) and ethyl iodide(0.25 ml) was heated at reflux in acetonitrile(0.5 ml) for 12 h under argon atmosphere, while shielded from light. The mixture was concentrated under reduced pressure and the resulting residue purified by flash chromatography on silica gel (methanol:methylene chloride=1:10) to afford 22 mg of the title compound of this example as a yellow solid(85% yield).

mp: 35.1°–37.5° C.

$^1$H-NMR(300 MHz, CDCl$_3$): δ0.88 (t, 3H, J=6.5 Hz), 1.20–1.62(m, 28H), 1.73(t, 3H, J=6.5 Hz), 2.29–2.36(m, 1H), 2.60–2.73(m, 4H), 3.39–3.53(m, 4H), 4.30–4.35(m,

1H), 4.54–4.61(m, 1H), 4.82–4.90(m, 2H), 5.03(q, 2H, J=7.3 Hz), 5.29–5.49(m, 2H), 7.75(d, 1H, J=8.1 Hz), 8.07(t, 1H, J=7.3 Hz), 8.46(t, 1H, J=8.0 Hz), 9.67(d, 1H, J=6.1 Hz)

IR(KBr): 3450, 2921, 2851, 1748, 1683, 1507, 1218, 770 cm⁻¹

Mass(FAB, m/z): 547(M⁺–I)

Example 2 trans-2-[[N-Acetyl-N-[[[4-[(hexadecyloxy)methyl]-2-oxetanyl]methoxy]carbonyl]amino]methyl]-1-ethyl-pyridinium iodide

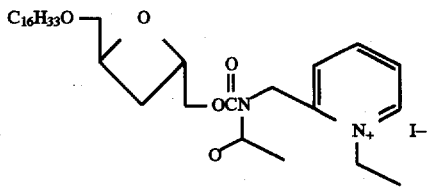

Following the procedure described in example 1f, the trans compound obtained in example 1e (32 mg) was reacted with ethyl iodide (0.8 ml) in acetonitrile(0.5 ml) to afford 35 mg of the title compound of this example as a yellow solid(80% yield).

mp: 39.7°–42.5° C.

¹H-NMR(300 MHz, CDCl₃): δ0.88(t, 3H, J=6.5 Hz), 1.20–1.62(m, 28H), 1.73(t, 3H, J=7.4 Hz), 2.42–2.47(m, 1H), 2.50–2.60(m, 1H), 2.67(s, 3H), 3.43–3.60(m, 4H), 4.43–4.57(m, 2H), 4.68–4.78(m, 1H), 4.85–4.95(m, 1H), 5.10(q, 2H, J=7.4 Hz), 5.44(s, 2H), 7.82(d, 1H, J=8.0 Hz), 8.05(t, 1H, J=7.1 Hz), 8.46(t, 1H, J=7.8 Hz), 9.57(d, 1H, J=6.3 Hz)

IR(KBr): 3446, 2920, 285, 1743, 1684, 1508, 1218, 774 cm⁻¹

Mass(FAB, m/z): 547 (M⁺–I)

Example 3 cis-2-[[N-Acetyl-N-[[[4-[[(octadecylcarbamoyl)oxy]methyl]-2-oxetanyl]methoxy]carbonyl]amino]methyl]-1-ethyl-pyridinium iodide

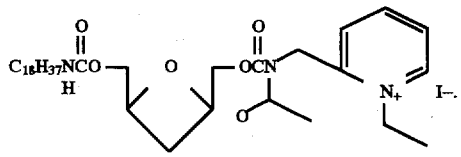

(a) 1-(benzyloxy)-4-penten-2-ol

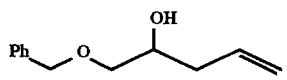

Following the procedure described in example 1a, but replacing n-hexadecyloxy aldehyde with benzyloxy aldehyde, the desired product was obtained as a colorless oil (83% yield).

¹H-NMR(300 MHz, CDCl₃): δ2.26(t, 2H, J=6.9 Hz), 2.44(d, 1H, J=3.4 Hz), 3.37(dd, 1H, J=9.4 Hz, J=3.5 Hz), 3.51(dd, 1H, J=9.4 Hz, J=7.3 Hz), 3.86–3.90(m, 1H), 4.55(s, 2H), 5.07–5.14(m, 2H), 5.78–5.87(m, 1H), 7.26–7.38(m, 5H)

(b) 1-(benzyloxy)-4,5-epoxy-pentan-2-ol

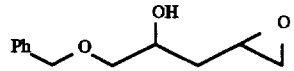

Following the procedure described in example 1b, but replacing the compound prepared in example 1a with the compound prepared in example 3a, the desired product was obtained as a colorless oil (94% yield).

¹-NMR(300 MHz, CDCl₃): δ1.48–1.87(2H), 2.50–2.55 (m, 2H), 2.75–2.83(m, 1H), 3.09–3.13(m, 1H), 3.36–3.59 (m, 2H), 4.02–4.08(m, 1H), 4.56(s, 2H), 7.25–7.39(m, 5H)

(c) cis, trans-4-[(benzyloxy)methyl]oxetane-2-methanol

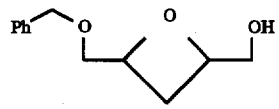

Following the procedure described in example 1c, but replacing the compound prepared in example 1b with the compound prepared in example 3b, the desired product was obtained as a mixture of cis and trans isomer (32% yield).

¹H-NMR(300 MHz, CDCl₃): δ1.73–2.88(m, 2H), 3.49–3.58(m, 4H), 4.51–4.67(m, 3H), 4.81–4.88(m, 2H), 7.25–7.37(m, 5H),

Mass(EI, m/z): 208(M⁺)

(d) cis, trans-4-[[(N-octadecylcarbamoyl)oxy]methyl]-2-[(benzyloxy)methyl]oxetane

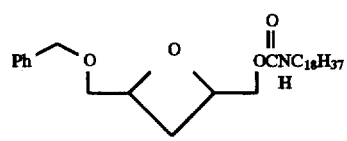

To a stirred solution of the compound prepared in example 3c (120 mg) in benzene (5 ml) was added pyridine (0.5 ml) followed by octadecyl isocyanate(208 mg), and the mixture was heated at 65° C. for 5 h. After cooling, the reaction mixture was diluted with methylene chloride(20 ml), was washed with 1N-HCl solution and water. The organic layer was dried, concentrated under reduced pressure and the resulting residue purified by flash chromatography on silica gel (ethyl acetate:hexane=1:3) to afford 220 mg of the desired product as a white solid(75% yield).

¹H-NMR(300 MHz, CDCl₃): δ0.86(t, 3H, J=6.4 Hz), 1.20–1.60(m, 32H), 2.32–250(m, 1H), 2.55–2.60(m, 1H), 3.06–3.16(m, 2H), 3.57(dd, 2H, J=4.2 Hz, J=4.1 Hz), 4.17–4.24 (m, 2H), 4.53–4.63(m, 2H), 7.24–7.36(m, 5H)

Mass(FAB, m/z): 504 (M⁺+1)

(e) cis, trans-4-[[(N-octadecylcarbamoyl)oxy]methyl]oxetane-2-methanol

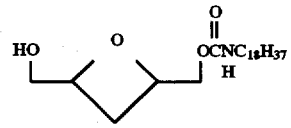

A mixture of the compound prepared in example 3d (200 mg) and palladium hydroxide on carbon (80 mg) was stirred in methanol(20 ml) at room temperature for 12 h under hydrogen atmosphere(1 atm). The mixture was filtered and the filtrate concentrated under reduced pressure to afford 154 mg of the desired compound as a white solid(95% yield).

mp: 79.6°–80.3° C.

¹H-NMR(300 MHz, CDCl₃): δ0.87(t, 3H, J=6.4 Hz), 1.20–1.60(m, 32H), 1.60–2.05 (m, 1H), 2.40–2.68(m, 2H), 3.14–3.22(m, 2H), 3.53–3.82 (m, 2H), 4.08–4.40(m, 2H), 4.76–4.87(m, 3H)

IR(KBr):3346, 2920, 2848, 1687, 1532, 1470, 1252, 1140, 1024, 720 cm⁻¹

Mass(EI, m/z): 413 (M⁺)

(f) cis-[4-[[(N -octadecylcarbamoyl)oxy]methyl]-2-oxetanyl]methyl phenyl carbonate and its trans isomer

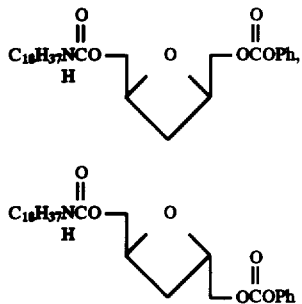

To a stirred solution of the compound prepared in example 3e (277 mg) in chloroform(15 ml) was added pyridine (0.13 ml) followed by phenyl chloroformate(0.12 ml) at 0° C. After stirring at room temperature for 1 h, the reaction mixture was poured into the saturated ammonium chloride (10 ml). The organic layer was washed with 10% sodium bicarbonate solution and water, dried, concentrated under reduced pressure. The resulting residue was purified by flash chromatography on silica gel (ethyl acetate:hexane=1:2) to afford 120 mg of the cis isomer and 125 mg of trans isomer (overall yield 82%).

cis isomer; mp: 69.8°–70.2° C.

¹H-NMR(300 MHz, CDCl₃): δ0.88(t, 3H, J=6.4 Hz), 1.12–1.55(m, 32H), 2.50–2.70 (m, 2H), 3.11–3.18(m, 2H), 4.22(d, 2H, 3.7 Hz), 4.32(dd, 1H, J=12.2 Hz, J=2.9 Hz), 4.41(dd, 1H, J=12.2 Hz, J=4.5 Hz), 4.92–5.02(m, 3H), 7.12–7.42(m, 5H)

IR(KBr): 3338, 2922, 2851, 1767, 1686, 1534, 1471, 1267, 1026, 958, 862, 774 cm⁻¹

Mass(FAB, m/z): 534 (M⁺+1)

trans isomer; mp: 76.2°–76.8° C.

¹H-NMR(300 MHz, CDCl₃): δ0.87(t, 3H, J=6.4 Hz), 1.20–1.60(m, 32H), 2.52–2.69(m,2H), 3.15–3.22(m, 2H), 4.27(d, 2H, J=4.9 Hz), 4.43–4.49(m, 2H), 4.75(br s, 1H) 4.88–4.94(m, 2H), 7.17–7.41 (m, 5H)

IR(KBr): 3353, 2922, 2848, 1762, 1686, 1530, 1469, 1263, 1025, 957, 858, 776, 720 cm⁻¹

Mass(FAB, m/z):534 (M⁺+1)

(g) cis-2-[[N-[[[4-[[(octadecylcarbamoyl)oxy]methyl]-2-oxetanyl]methoxy]carbonyl]amino]methyl]pyridine

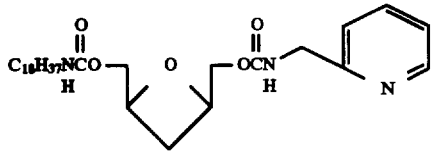

A mixture of the cis compound prepared in example 3f (309 mg) and 2-picolyl amine(0.11 ml) was heated at reflux in toluene(2 ml). After cooling, the mixture was diluted with methylene chloride(20 ml), washed with 1N-HCl solution followed by water. The organic layer was dried, concentrated under reduced pressure and the resulting residue purified by flash chromatography on silica gel (ethyl acetate:hexane=4:1) to afford 250 mg of the desired product as white solid(80% yield).

mp: 104.6°–106.0° C.

¹H-NMR(300 MHz, CDCl₃): δ0.88 (t, 3H, J=6.5 Hz), 1.20–1.60(m, 32H), 2.25–2.38(m, 1H), 2.55–2.70(m, 1H), 3.12–3.19(m, 2H), 4.19(s, 2H), 4.24(d, 2H, J=3.5 Hz), 4.50(d, 2H, J=5.4 Hz), 4.88–4.92 (m, 2H), 5.05(br s, 1H), 5.95(br s, 1H), 7.15–7.20(m, 1H), 7.27(d, 1H, J=6.5 Hz), 7.65(t, 1H, J=7.6 Hz), 8.53(d, 1H, J=4.4 Hz)

IR(KBr): 3317, 2920, 2847, 1692, 1544, 1470, 1435, 1268, 1152, 1033, 919. 864 cm⁻¹

Mass(EI, m/z): 547 (M⁺)

(h) cis-2-[[N-Acetyl-N-[[[4-[[(octadecylcarbonyl)oxy] methyl]-2-oxetanyol]methoxy]carbonyl]amino]methyl] pyridine

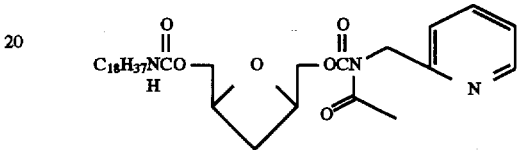

Following the procedure described in example 1e, but replacing the compound prepared in example 1d with the compound prepared in example 3g, the desired product was obtained (90% yield).

¹H-NMR(300 MHz, CDCl₃): δ0.89(t, 3H, J=6.5 Hz), 1.15–1.56(m, 32H), 2.15–2.25(m, 2H), 2.45–2.55(m, 1H), 2.62(s, 3H), 3.13–3.20(m, 2H), 4.03–4.14(m, 2H), 4.28(d, 2H, J=4.7 Hz), 4.80–4.84(m, 2H), 5.12(d, 2H, J=3.3 Hz), 7.13(d, 2H, J=7.7 Hz), 7.62(t, 1H, J=5.9 Hz), 8.51(d, 1H, J=3.8 Hz)

(i) Preparation of the title compound of this example

Following the procedure described in example 1f, but replacing the compound prepared in example 1e with the compound prepared in example 3 h, the title compound of this example was obtained as a yellow solid (88% yield).

mp: 53.7°–56.5° C.

¹H-NMR(300 MHz, CDCl₃): δ0.88(t, 3H, J=6.6 Hz), 1.17–1.59(m, 32H), 1.73(t, 3H, J=7.3 Hz), 2.20–2.72(m, 5H), 3.12–3.20(m, 2H), 4.07(d, 2H, J=4.4 Hz), 4.15–4.30(m, 2H), 4.85–4.95(m, 2H), 4.95–5.10(q, 2H, J=5.9 Hz), 5.31(br s, 1H), 5.47(s, 2H), 7.80(d, 1H), 8.02(t, 1H, J=6.3 Hz), 8.44(t, 1H, J=7.5 Hz), 9.45(d, 1H, J=6.0 Hz)

IR(KBr): 3375, 2919, 2850, 1746, 1686, 1630, 1528, 1358, 1227, 1160, 985, 774 cm⁻¹

Mass(FAB,m/z):618 (M⁺-I)

Example 4 cis-2-[[N-Acetyl-N-[[[4-[[(octadecylcarbamoyl)oxy] methyl]-2-oxetanyl]methoxy]carbonyl]amino]methyl]-1-ethyl-pyridinium chloride

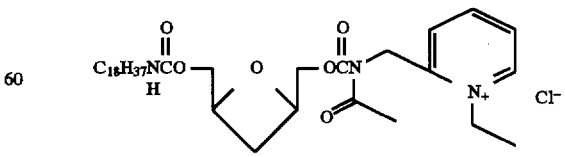

The compound obtained in example 3i (128 mg) dissolved in 70% methanol (0.5 ml) was eluted through the column packed with IRA-410 resin (5 g, Cl⁻ form) using the eluent (methanol:water=7:3) to afford 105 mg of the title compound of this example(94% yield). Mass(FAB, m/z): 618 (M⁺−)

Example 5 trans-2-[[N-Acetyl-N-[[[4-[[(octadecylcarbamoyl)oxy]methyl]-2-oxetanyl]methoxy]carbonyl]amino]methyl]-1-ethyl-pyridinium iodide

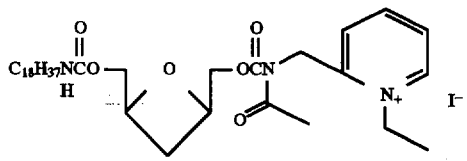

(a) trans-2-[[N -[[[4-[[(octadecylcarbamoyl)oxy]methyl]-2-oxetanyl]methoxy]carbonyl]amino]methyl]pyridine

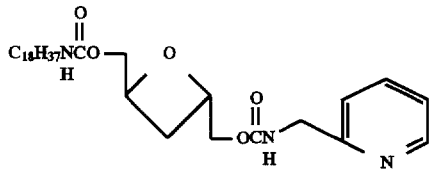

Following the procedure described in example 3g, but replacing the cis compound separated in example 3f with the trans compound separated in example 3f, the desired compound was obtained (93% yield).

mp: 97.0°–98.6° C.

¹H-NMR(300 MHz, CDCl₃): δ0.88(t, 3H, J=6.5 Hz), 1.20–1.56(m, 32H), 2.52(br t, 2H), 3.13–3.21(m, 2H), 4.24 (d, 2H, J=4.1 Hz), 4.29(d, 2H, J=4.5 Hz), 4.50(d, 2H, J=5.5Hz: 4.80–4.88(m, 3H), 5.99(br s, 1H), 7.18(d, 1H, J=7.4 Hz ), 7.27(d, 1H, J=5.4 Hz), 7.65(t, 1H, J=7.7 Hz), 8.53(d, 1H, J=4.4 Hz)

IR(KBr): 3342, 2917, 2849, 1690, 1544, 1470, 1438, 1276, 1151, 1029, 993, 867, 749 cm⁻¹

Mass(EI, m/z): 547 (M⁺)

(b) trans-2-[[N -Acetyl-N-[[[4-[[(octadecylcarbamoyl)oxy]methyl]-2-oxetanyl]methoxy]carbonyl]amino]methyl]pyridine

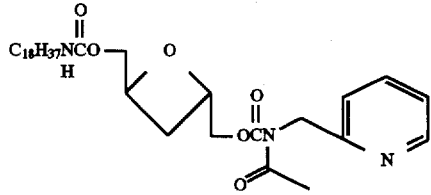

Following the procedure described in example 1e, but replacing the compound prepared in example 1d with the compound prepared in example 5a, the desired compound was obtained as a white solid (93% yield).

¹H-NMR(300 MHz, CDCl₃): δ0.88(t, 3H, J=6.5 Hz), 1.15–1.56(m, 32H), 2.20–2.40 (m, 2H), 2.64(s, 3H), 3.13–3.20(m, 2H), 4.16(d, 2H, J=4.3 Hz), 4.24–4.40(m, 2H), 4.51–4.60(m, 1H), 4.75–4.86 (m, 2H), 5.14(d, 2H, J=2.5 Hz), 7.14(d, 2H, J=7.4 Hz), 7.61(t, 1H, J=6.0 Hz), 8.48(d, 1H, J=4.6 Hz)

(c) Preparation of the title compound of this example

Following the procedure described in example 1f, but replacing the compound prepared in example 1e with the compound prepared in example 5b, the title compound of this example was obtained as a yellow solid (90% yield).

mp: 56.9°–60.3° C.

¹H-NMR(300 MHz, CDCl₃): δ0.88 (t, 3H, J=6.6 Hz), 1.20–1.65(m, 32H), 1.73(t, 3H, J=7.3 Hz), 2.36–2.54(m, 1H), 2.54–2.65(m, 1H), 2.68(s, 3H), 3.14–3.21(m, 2H), 4.18(d, 2H, J=4.8 Hz), 4.35–4.55 (m, 2H), 4.75(br s, 1H), 4.80–4.92(m, 2H), 5.02(q, 2H, J =7.4 Hz), 5.46(s, 2H), 7.78(d, 1H, J=8.1 Hz), 8.01(t, 1H, J=6.0 Hz), 8.45(t, 1H, J=7.7 Hz), 9.44(d, 1H, J=6.7 Hz)

IR(Kbr):3343, 2919, 2850, 1743, 1701; 1630, 1528, 1358, 1227, 1159, 985, 773 cm⁻¹

Mass(FAB, m/z): 618 (M⁺−I)

Example 6

2-[[-Acetyl-N-[[[3-[[(octadecylcarbamoyl)oxy]methyl]-3-oxetanyl]methoxy]carbonyl]amino]methyl]-1-ethyl-pyridinium iodide

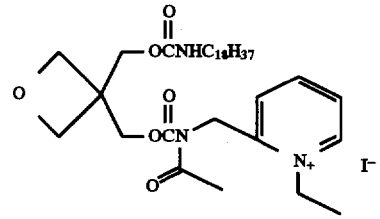

(a) 3,3-bis-(benzyloxymethyl)oxetane

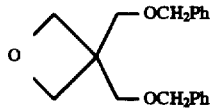

To a cold (0° C.)stirred solution of pentaerythritol dibenzyl ether(420 mg) in dry tetrahydrofuran(20 ml) was added slowly n-butyllithium (0.86 ml, 2.73M in hexane) via a syringe, and the resulting solution was stirred for 10 min under argon atmosphere. A solution of p-toluene sulfonyl chloride (261 mg) in dry tetrahydrofuran(5 ml) was then added over 20 min. After stirring for 1 h at 0° C., an equivalent of n-butyllithium(0.86 ml) was added over 10 min and the reaction mixture allowed to warm to 60° C. After 2 h the reaction mixture was poured into an ice-cold water and extracted with ethyl acetate. The organic layer was dried, concentrated under reduced pressure, and the resulting residue purified by flash chromatography on silica gel (ethyl acetate:hexane=1:4) to afford 293 mg of the desired product as a colorless oil (74% yield).

¹H-NMR(80 MHz, CDCl₃): δ3.70(s, 4H), 4.47(s, 4H), 4.54(s, 4H), 7.30(br s, 10H)

(b) 3,3-bis-(hydroxymethyl)oxetane

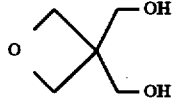

A mixture of the above-described compound (283 mg) and palladium hydroxide on carbon (130 mg) was stirred at room temperature overnight under hydrogen atmosphere(1 atm). The reaction mixture was filtered and the filtrate concentrated to afford 112 mg of the desired product as a colorless oil (quantitative yield).

¹H-NMR(80 MHz, CDCl₃): δ2.60(br s, 2H), 4.12(s, 4H), 4.46(s, 4H)

(c) 3-[[N-(Octadecylcarbamoyl)oxy]methyl]oxetane-3-methanol

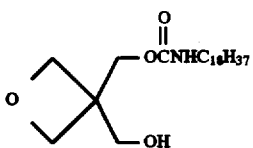

To a cold (0° C.)stirred solution of 3,3-bis-(hydroxymethyl) oxetane(222 mg) in dry tetrahydrofuran (20 ml) was added octadecyl isocyanate(584 mg) and then dibutyltin oxide (35 mg) as the catalyst. After stirring at room temperature for 2 h, the reaction mixture was filtered and the filtrate concentrated under reduced pressure. The resulting residue was purified by flash chromatography on silica gel (ethyl acetate:hexane=1:2) to afford 554 mg of the desired product as a white solid (71% yield).

mp: 66.8°–67.9° C.

$^1$H-NMR(300 MHz, CDCl$_3$): δ0.88(t, 3H, J=6.8 Hz), 1.25(br s, 30H), 1.46(m, 2H), 3.03(br s, 1H), 3.17(q, 2H, J=6.6 Hz), 3.79(s, 2H), 4.40(s, 2H), 4.45(br s, 4H), 4.82(br s, 1H)

IR(KBr): 3400, 2921, 2849, 1692, 1523, 1240, 1048, 966 cm$^{-1}$

Mass(EI, m/z): 414(M$^+$+1)

(d) 2-[[N-[[[3-[[(Octadecylcarbamoyl)oxy]methyl]-3-oxetanyl]methoxy]carbonyl]amino]methyl]pyridine

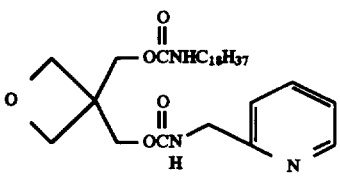

Following the procedure described in example 1d, but replacing the compound prepared in example 1c with the compound prepared in example 6c, the desired compound was obtained as a light yellow solid (87% yield).

mp: 62.7°–63.3° C.

$^1$H-NMR(300 MHz, CDCl$_3$): δ0.88(t, 3H, J=6.8 Hz), 1.25(br s, 30H), 1.48(m, 2H), 3.15 (q, 2H, J=6.3 Hz), 4.29(s, 2H), 4.33(s, 2H), 4.50(br s, 6H), 4.90(br s, 1H), 6.03(br s, 1H), 7.17–7.28(m, 2H), 7.63–7.69(m, 1H), 8.53(d, 1H, J=4.2 Hz)

IR(KBr): 3363, 2920, 2850, 1703, 1530, 1470, 1255, 1148, 1043, 770 cm$^{-1}$ (e) 2-[[N-Acetyl-N-[[[3-[[(octadecylcarbamoyl)oxy]methyl]-3-oxetanyl]]methoxy]carbonyl]amino]methyl]pyridine

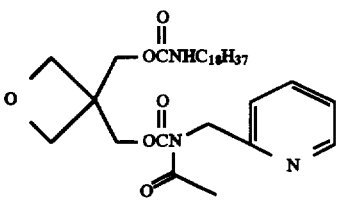

Following the procedure described in example 1e, but replacing the compound prepared in example 1d with the compound prepared in example 6d, the desired compound was obtained as a white solid (84% yield).

mp: 57.5°–58.3° C.

$^1$H-NMR(300 MHz, CDCl$_3$): δ0.88(t, 3H, J=6.8 Hz), 1.25(br s, 30H), 1.49(m, 2H), 2.64(s, 3H), 3.15(q, 2H, J=6.3 Hz), 4.12(s, 2H), 4.17(d, 2H, J=6.4 Hz), 4.28(d, 2H, J=6.4 Hz), 4.37(s, 2H), 5.08(s, 2H), 5.10(br s, 1H), 7.10–7.16(m, 2H), 7.62(m, 1H), 8.47(d, 1H, J=4.5 Hz)

IR(KBr): 3311, 2919, 2849, 1740, 1695, 1535, 1352, 1214, 1078, 980 cm$^{-1}$ (f) Preparation of the title compound of this example Following the procedure described in example 1f, but replacing the compound prepared in example 1e with the compound prepared in example 6e, the title compound of this example was obtained as a yellow solid (75% yield).

mp: 48.2°–51.1° C.

$^1$H-NMR(300 MHz, CDCl$_3$): δ0.88(t, 3H, J=6.8 Hz), 1.25–1.48(m, 32H), 1.73(t, 3H, J=7.3 Hz), 2.66(s, 3H), 3.12(q, 2H, J=6.3 Hz), 4.24(s, 2H), 4.43(d, 2H, J=6.7 Hz), 4.49(d, 2H, J=6.7 Hz), 4.57(s, 2H), 5.02(q, 2H, J=7.2 Hz), 5.03(br s, 1H)5.51(s, 2H), 7.89(d, 1H, J=6.8 Hz), 8.00(t, 1H, J=6.3 Hz), 8.45(t, 1H, J=7.8 Hz), 9.39(d, 1H, J=5.7 Hz)

IR(KBr): 3361, 2919, 2849, 1717, 1527, 1467, 1353, 1226, 1155, 1085, 981, 772, 595 cm$^{-1}$

Mass(FAB, m/z): 746 (M$^+$+1)

Example 7

2-[[N-Acetyl-N-[[[3-[[(octadecylcarbamoyl)oxy]methyl]-3-oxetanyl]methoxy]carbonyl]amino]methyl]-1-ethyl-pyridinium chloride

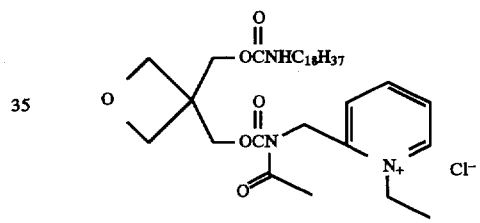

The title compound obtained in example 6f (128 mg) dissolved in 70% methanol (0.5 ml) was passed through the column packed with IRA-410 resin (5 g, Cl$^-$ form) using the eluent (methanol:water =7:3) to afford 105 mg of the title compound of this example(94% yield).

IR(KBr): 3358, 2921, 2850, 1717, 1630, 1527, 1462, 1354, 1226, 1156, 1086, 982, 773, 598 cm$^{-1}$

Mass(FAB, m/z): 618 (M$^+$–Cl)

Example 8

2-[[N-Acetyl-N-[[[3-[[(hexadecylcarbamoyl)oxy]methyl]-3-oxetanyl]methoxy]carbonyl]amino]methyl]-1-ethyl-pyridinium iodide

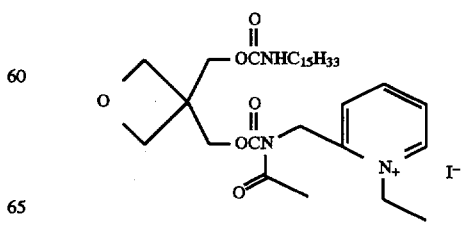

(a) 3,3-Bis[[(phenoxycarbonyl)oxy]methyl]oxetane

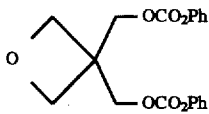

To a cold(0° C.) stirred solution of the compound prepared in example 6b (200 mg) in methylene chloride(15 ml) was added pyridine (0.33 ml) and then phenyl chloroformate (0.47 ml). After stirring at room temperature for 1 h, the reaction mixture was diluted with methylene chloride, and washed with water. The organic layer was dried, concentrated under reduced pressure and the resulting residue purified by flash chromatography on silica gel (ethyl acetate:hexane=1:3) to afford 420 mg of the desired product (78% yield).

$^1$H-NMR(80 MHz, CDCl$_3$): δ4.50(br s, 8H), 7.00–7.30 (m, 10H)

(b) 2-[[N-[[[3-[[(Hexadecylcarbamoyl)oxy]methyl]-3-oxetanyl]methoxy]carbonyl]amino]methyl]pyridine

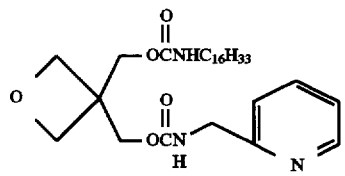

A mixture of the compound prepared in example 8a(300 mg) and n-hexadecyl amine (240 mg) was heated in toluene (2 ml) at 80° C. for 6 h. 2-Picolyl amine (0.2 ml) was then added, and the mixture was heated at 80° C. overnight. After cooling, the reaction mixture was diluted with ethyl acetate (30 ml) and washed successively with 0.1N-HCl solution and water. The organic layer was dried, concentrated under reduced pressure, and the resulting residue purified by flash chromatography on silica gel (ethyl acetate:hexane=1:1) to afford 160 mg of the desired product (37% yield).

mp: 53.1°–53.9° C.

$^1$H-NMR(300 MHz, CDCl$_3$): δ0.87(t, 3H, J=6.4 Hz), 1.25(br s, 26H), 1.48(br s, 2H), 3.15(q, 2H, J=6.4 Hz), 4.29(s, 2H), 4.33(s, 2H), 4.50(s, 4H), 4.79(br s, 1H), 5.92 (brs, 1H), 7.17–7.27(m, 2H), 7.63–7.69(m, 1H), 8.53(d, 1H, J=4.8 Hz)

IR(KBr): 3362, 2920, 2850, 1702, 1530, 1256, 1042, 769 cm$^{-1}$ (c) 2-[[N-Acetyl-N-[[[3-[[(hexadecylcarbamoyl)oxy]methyl]-3-oxetanyl]methoxy]carbonyl]amino]methyl]pyridine

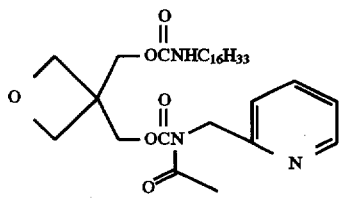

Following the procedure described in example 1e, but replacing the compound prepared in example 1d with the compound prepared in example 8b, the desired compound was obtained as a white solid (79% yield).

$^1$H-NMR(300 MHz, CDCl$_3$): δ0.87(t, 3H, J=6.4 Hz), 1.25(br s, 26H), 1.47(br s, 2H), 2.64(s, 3H), 3.14(q, 2H, J=6.4 Hz), 4.11(s, 2H), 4.17(d, 2H, J=6.4 Hz), 4.28(d, 2H, J=6.4 Hz), 4.36(s, 2H), 5.07(s, 2H), 5.13(br s, 1H), 7.10–7.16(m, 2H), 7.59–7.65(m, 1H), 8.46(d, 1H, J=4.6 Hz)

IR(KBr): 3310, 2920, 2850, 1741, 1694, 1536, 1353, 1220, 1078, 979, 774, 589 cm$^{-1}$ (d) Preparation of the title compound of this example Following the procedure described in example 1f, but replacing the compound prepared in example 1e with the compound prepared in example 8c, the title compound of this example was obtained as a yellow solid (37% yield).

mp: 41.0°–45.5° C.

$^1$H-NMR(300 MHz, CDCl$_3$): δ0.87(t, 3H, J=6.4 Hz), 1.25(br s, 26H), 1.48(br s, 2H), 1.73(t, 3H, J=7.4 Hz), 2.66(s, 3H), 3.11(q, 2H, J=6.4 Hz), 4.24(s, 2H), 4.43(d, 2H, J=6.7 Hz), 4.51(d, 2H, J=6.7 Hz), 4.57(s, 2H), 5.02(q, 2H, J=7.4 Hz), 5.51(s, 2H), 7.91–8.03(m, 2H), 8.46(t, 1H, J=7.9 Hz), 9.48(d, 1H, J=5.6 Hz)

IR(KBr): 3358, 2921, 2850, 1717, 1630, 1527, 1462, 1354, 1226, 1156, 1086, 982, 773 cm$^{-1}$

Mass(FAB, m/z): 718 (M$^+$1), 590 (M$^+$–I)

Example 9

2-[[N-Acetyl-N-[[[3-[(hexadecyloxy)methyl]-3-oxetanyl]methoxy]carbonyl]amino]methyl]-1-ethyl-pyridinium iodide

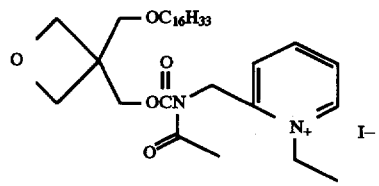

(a) 3-[(hexadecyloxy)methyl]oxetane-3-methanol

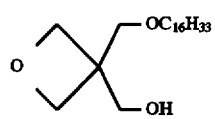

To a cold(0° C.) 60% sodium hydride(640 mg, washed previously with hexane) suspension in dry dimethylformamide(10 ml) was added 3,3-bis-(hydroxymethyl)oxetane (1.18 g) in dry dimethylformamide (10 ml). After the evoution of hydrogen gas subsided, n-hexadecyl bromide (0.65 ml) in dry dimethylformamide(1 ml) was added, and the mixture was then heated at 60° C. for 7 h. After cooling, the reaction mixture was poured into an ice-cold water, neutralized with 1N-HCl solution, and extracted with ethyl acetate. The organic layer was dried, concentrated under reduced pressure and the resulting residue purified by flash chromatography on silica gel (ethyl acetate:hexane=1:2) to afford 313 mg of the desired product as a white solid(50% yield).

mp: 46.7°–48.3° C.

$^1$H-NMR(300 MHz, CDCl$_3$): δ0.88(t, 3H, J=6.8 Hz), 1.26(br s, 26H), 1.57(q, 2H, J=6.7 Hz), 2.47(t, 1H, J=5.7 Hz), 3.47(t, 2H, J=6.4 Hz), 3.78 (s, 2H), 3.93(d, 2H, J=5.4 Hz), 4.41(d, 2H, J=6.4 Hz), 4.47 (d, 2H, J=6.0 Hz)

IR(KBr): 3397, 2919, 2852, 1473, 1121, 1063, 963, 716 cm$^{-1}$ (b) 2-[[N-[[3-[(hexadecyloxy)methyl]3-oxetanyl]methoxy]carbonyl]amino]methyl]pyridine

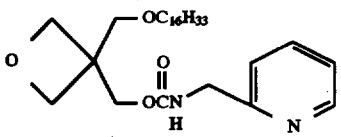

Following the procedure described in example 1d, but replacing the compound prepared in example 1c with the compound prepared in example 9a, the desired compound was obtained as a white solid(72% yield).

mp: 42.2°–43.0° C.

$^1$H-NMR(300 MHz, CDCl$_3$): δ0.88(t, 3H, J=6.8 Hz), 1.26(br s, 26H), 1.55(m, 2H), 3.43(t, 2H, J=6.4 Hz), 3.61(s, 2H), 4.31(s, 2H), 4.44–4.51(m, 6H), 5.94(br s, 1H), 7.18(m, 1H), 7.27(m, 1H), 7.65 (m, 1H), 8.53(d, 1H, J=4.9 Hz)

IR(KBr): 3265, 2924, 2851, 1721, 1550, 1469, 1259, 981, 769 cm$^{-1}$ (c) 2-[[N-Acetyl-N-[[[3-[(hexadecyloxy)methyl]3-oxetanyl]methoxy]carbonyl]amino]methyl]pyridine

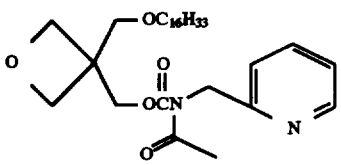

Following the procedure described in example 1e, but replacing the compound prepared in example 1d with the compound prepared in example 9b, the desired compound was obtained as a light yellow oil(94% yield).

$^1$H-NMR(300 MHz, CDCl$_3$): δ0.87(t, 3H, J=6.9 Hz), 1.25(br s, 26H), 1.49(m, 2H), 2.65(s, 3H), 3.31(t, 2H, J=6.7 Hz), 3.3.9(s, 2H), 4.21(d, 2H, J=6.2 Hz), 4.27 (d, 2H, J=6.4 Hz), 4.35(s, 2H), 5.08(s, 2H), 7.08–7.15(m, 2H), 7.58–7.64 (m, 1H), 8.48 (d, 1H, J=4.4 Hz)

(d) Preparation of the title compound of this example

Following the procedure described in example 1f, but replacing the compound prepared in example 1e with the compound prepared in example 9c, the title compound of this example was obtained as a yellow solid (38% yield).

mp: 37.1°–41.4° C.

$^1$H-NMR(300 MHz, CDCl$_3$): δ0.87(t, 3H, J=6.8 Hz), 1.26(br s, 26H), 1.50(br s, 2H), 1.71–1.77(m, 3H), 2.67(s, 3H), 3.35–3.45(m, 2H), 3.63(s, 2H), 4.40(d, 2H, J=4.0 Hz), 4.42(d, 2H, J=6.5 Hz), 4.55(s, 2H), 4.99–5.08(m, 2H), 5.50(s, 2H), 7.85(d, 1H, J=8.1 Hz), 8.02–8.08(m, 1H), 8.46–8.49(m, 1H), 9.53(d, 1H, J=4.9 Hz)

IR(KBr): 2919, 2850, 1749, 1685, 1629, 1462, 1371, 1217, 1166, 981, 772 cm$^{-1}$

Mass(FAB, m/z): 575 (M$^+$)

Example 10

N-[5-[[[3-[(Hexadecyloxy)methyl]-3-oxetanyl]methoxy]carbonyl]pentyl]pyridinium bromide

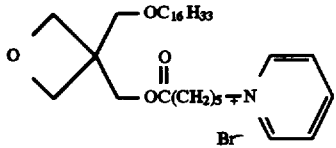

(a)[3-[(Hexadecyloxy)methyl]-3-oxetanyl]methyl 6-bromohexanoate

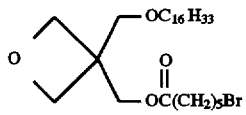

To a cold (0° C.) stirred solution of the compound prepared in example 9a (600 mg) in methylene chloride(10 ml) was added pyridine(0.2 ml) and then 6-bromo hexanoyl chloride (0.32 ml), and the mixture was allowed to warm to room temperature. After stirring at room temperature for 3 hrs, the reaction mixture was diluted with ethyl acetate, washed with water. The organic layer was concentrated under reduced pressure and the resulting residue purified by flash chromatography on silica gel (ethyl acetate:hexane= 1:3) to afford 720 mg of the desired product as a light yellow solid(79% yield).

$^1$H-NMR(300 MHz, CDCl$_3$): δ0.88(t, 3H, J=6.8 Hz), 1.25(br s, 26H), 1.50–1.55(m, 4H), 1.65(m, 2H), 1.88(m, 2H), 2.37(2H, J=7.5 Hz), 3.38–3.46(m, 4H), 3.61(s, 2H), 4.29(s, 2H), 4.45–4.50(m, 4H)

IR(KBr): 2925, 2856, 1739, 1461, 1249, 1116, 986, 839, 727 cm$^{-1}$ (b) Preparation of the title compound of this example The above-described compound (200 mg) was dissolved in dry pyridine (2 ml) and heated at 100° C. for 3 h. After removal of excess pyridine under reduced pressure, the residue obtained was purified by flash chromatography on silica gel (chloroform:methanol=20:1) to afford 204 mg of the title compound (89% yield).

mp: 46.8°–47.4° C.

$^1$H-NMR(300 MHz, CDCl$_3$): δ0.88(t, 3H, J=6.6 Hz), 1.26(br s, 26H), 1.34–1.58(m, 4H), 1.68–1.75(m, 2H), 2.05–2.10(m, 2H), 2.37(t, 2H, J=7.2 Hz), 3.46(t, 2H, J=6.5 Hz), 3.61(s, 2H), 4.27(s, 2H), 4.49(s, 4H), 4.74(m, 2H), 8.13(t, 2H, J=6.8 Hz), 8.54(t, 1H, J=7.8 Hz), 9.12(t, 2H, J=4.8 Hz)

IR(KBr): 3412, 2918, 2849, 1732, 1634, 1487, 1369, 1176, 1115, 974, 777, 719 cm$^{-18}$

Mass(FAB, m/z): 598 (M$^+$), 518 (M$^+$–Br)

Example 11

N-[5-[[[3-[(Hexadecyloxy)methyl]-3-oxetanyl]methoxy]carbonyl]pentyl]thiazolium bromide

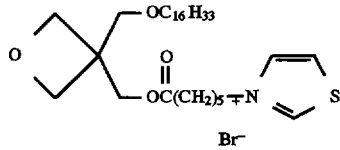

The compound prepared in example 10a(300 mg) was dissolved in thiazole (1 ml) and heated at 100° C. for 3 h. After removal of excess thiazole under reduced pressure, the residue obtained was purified by flash chromatography on silica gel (chloroform:methanol=20:1) to afford 116 mg of the title compound (33% yield).

m.p.: 48.2°–52.9° C.

$^1$H-NMR(300 MHz, CDCl$_3$): δ0.88(t, 3H, J=6.7 Hz), 1.25(br s, 26H), 1.43–1.55(m, 4H), 1.66–1.74(m, 2H), 2.03–2.13(m, 2H), 2.38(t, 2H, J=6.6 Hz), 3.44(t, 2H, J=6.9 Hz), 3.60(s, 2H), 4.26(s, 2H), 4.46(s, 4H), 4.90(t, 2H, J=7.4 Hz), 8.27(m, 1H), 8.46(d, 1H, J=3.7 Hz), 11.30(s, 1H)

IR(KBr): 3400, 2919, 2850, 1731, 1550, 1466, 1143, 976, 839, 720 cm$^{-1}$

Mass(FAB, m/z): 604 (M⁺), 524 (M⁺−Br)

Example 12

N-[5-[[[3-[[(Octadecylcarbamoyl)oxy]methyl]-3-oxetanyl]methoxy]carbonyl]pentyl]pyridinium bromide

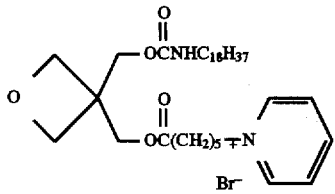

(a)[3-[[(N-Octadecylcarbamoyl)oxy]methyl]-3-oxetanyl]methyl-6-bromo hexanoate

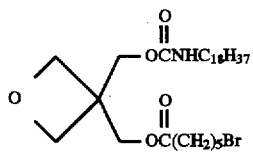

Following the procedure described in example 10a, but replacing the compound prepared in example 9a with the compound prepared in example 6c, the compound prepared in example 6c was reacted with 6-bromohexanoyl chloride to afford the desired compound as a white solid (76% yield).

mp: 44.7°–46.5° C.

¹H-NMR(300 MHz, CDCl₃): δ0.85(t, 3H, J=6.9 Hz), 1.23(br s, 30H) 1.41–1.53(m, 4H), 1.65(m, 2H), 1.85(m, 2H), 2.34(t, 2H, J=4.5 Hz), 3.15(q, 2H, J=6.4 Hz), 3.37(m, 2H), 4.25(d, 4H, J=5.4 Hz), 4.43(d, 2H, J=6.4 Hz), 4.48(d, 2H, J=6.4 Hz), 4.70(br s, 1H)

IR(KBr): 3267, 2919, 2850, 1732, 1690, 1557, 1407, 1265, 1170, 995, 721 cm⁻¹

(b) Preparation of the title compound of this example

The compound prepared in example 12a(600 mg) was dissolved in pyridine (2 ml) and heated at 100 C. for 12 h. After removal of excess pyridine under reduced pressure, the residue obtained was purified by flash chromatography on silica gel (chloroform:methanol=20:1) to afford 600 mg of the title compound of this example (88% yield).

mp: 52.1°–59.3° C.

¹H-NMR(300 MHz, CDCl₃): δ0.89(t, 3H, J=6.8 Hz), 1.27(br s, 30H), 1.43–1.50(m, 4H), 1.68–1.75(m, 2H), 2.05–2.10(m, 2H), 2.43(t, 2H, J=6.9 Hz), 3.12(t, 2H, J=6.9 Hz), 4.25–4.57(m, 8H), 4.70(t, 2H, J=7.8 Hz), 8.14(t, 2H, J=6.8 Hz), 8.59(t, 1H, J=7.5 Hz), 9.06(t, 2H, J=6.0 Hz)

IR(KBr): 3379, 2918, 2849, 1718, 1634, 1538, 1467, 1254, 1164, 982, 775, 684 cm⁻¹

Mass(FAB, m/z): 589 (M⁺−Br)

Example 13

3-[5-[[[3-[[(Octadecylcarbamoyl)oxy]methyl]-3-oxetanyl]methoxy]carbonyl]pentyl]thiazolium bromide

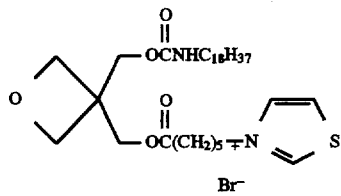

The compound prepared in example 12a(300 mg) was dissolved in thiazole (0.8 ml) and heated at 100° C. for 8 h. After removal of excess pyridine under reduced pressure, the residue obtained was purified by flash chromatography on silica gel (chloroform:methanol:water=100:15:2) to afford 154 mg of the title compound (45% yield).

mp: 42.3°–46.0° C.

¹H-NMR(300 MHz, CDCl₃): δ0.88(t, 3H, J=6.7 Hz), 1.25(br s, 30H), 1.35–1.50 (m, 4H), 1.65–1.72(m, 2H), 2.04–2.09(m, 2H), 2.38(t, 2H, J=6.6 Hz), 3.15(m, 2H), 3.47(s, 2H), 3.55(s, 2H), 4.11(s, 4H), 4.86(t, 2H, J=6.8 Hz), 5.25(brs, 1H), 8.33(d, 1H, J=2.5 Hz), 8.57(d, 1H, J=2.5 Hz), 10.95(br s, 1H)

IR(KBr): 3347, 2918, 2849, 1713, 1541, 1466, 1256, 1049 cm⁻¹

Mass(FAB, m/z): 675 (M⁺), 595 (M⁺−Br)

(g) preparation of the title compound of this example

Following the procedure described in example 11, but replacing the compound prepared in example 10a with the compound prepared in example 12a, the title compound of this example was obtained as a light yellow solid(50% yield).

mp: 48.3°–521° C.

¹H-NMR(300 MHz, CDCl₃): d 0.87(t, 3H, J=6.3 Hz), 1.25(s, 26H), 1.48(br s, 2H) 1.71 (t, 2H, J=3.8 Hz), 1.63(s, 3H), 2.64(s, 3H), 3.11(brs, 2H), 3.73(s, 2H), 3.99–4.21(m, 4H), 4.47(s, 2H), 5.12(br s, 2H), 5.35(br s, 1H), 5.59(s, 2H), 7.79(d, 1H, J=7.1 Hz), 7.97(br s, 1H), 8.39(t, 1H, J=7.7 Hz), 9.43(br s, 1H)

IR(KBr): 3410, 2924, 2853, 1706, 1635, 1526, 1460, 1363, 1226, 1160, 1087, 984, 772, 596 cm⁻¹

Example 14

2-[[N-Acetyl-N-[[[1-[[(octadecylcarbamoyl)oxy]methyl]-1-cyclobutyl]methoxy]carbonyl]amino]methyl]-1-ethyl-pyridinium iodide

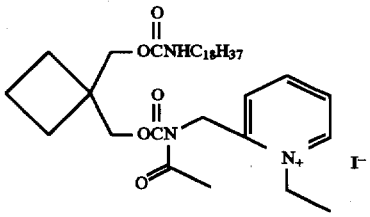

(a) 1-[[(N-Octadecylcarbamoyl)oxy]methyl]cyclobutane-1-methanol

[Structure: cyclobutane with -CH2-OCNHC18H37 (C=O) and -CH2-OH substituents]

To a cold (0° C.) stirred solution of 1,1-bis-(hydroxymethyl) cyclobutane(167 mg) in dry tetrahydrofuran (10 ml) was added octadecyl isocyanate(425 mg) and then dibutyltin oxide(35 mg) as the catalyst. After stirring at room temperature for 4 h, the reaction mixture was filtered and the filtrate concentrated under reduced pressure. The resulting residue was purified by flash chromatography on silica gel (ethyl acetate:hexane=1:5) to afford 580 mg of the desired product at a colorless solid (98% yield).

mp: 46.2°–46.5° C.
$^1$H-NMR(300 MHz, CDCl$_3$): δ0.88(t, 3H, J=6.4 Hz), 1.15–1.75(m, 33H), 1.76–1.89(m, 4H), 1.89–1.96(m, 2H), 3.10–3.20(m, 2H), 3.51(s, 2H), 4.16(s, 2H), 4.72(br s, 1H)
IR(KBr): 3327, 2919, 2859, 1692, 1541, 1468, 1269 cm$^{-1}$
Mass(EI, m/z): 411 (M$^+$)

(b) 2-[[N-[[[1-[[(Octadecylcarbamoyl)oxy]methyl]-1-cyclobutyl]methoxy]carbonyl]amino]methyl]pyridine

[Structure: cyclobutane with -CH2-OCNHC18H37 and -CH2-OC(=O)NH-CH2-pyridyl]

Following the procedure described in example 1d, but replacing the compound prepared in example 1c with the compound prepared in example 14a, the desired compound was obtained as a white solid(90% yield).

$^1$H-NMR(300 MHz, CDCl$_3$): δ0.88(t, 3H, J=6.3 Hz), 1.10–1.55(m, 32H), 1.73–2.00(m, 6H), 3.12–3.19(m, 2H)4.09(s, 2H), 4.12(s, 2H), 4.50(d, 2H, J=5.3Hz), 4.72(br s, 1H), 5.80(br s, 1H), 7.19(d, 1H, J=7.4 Hz), 7.26(d, 1H, J=7.0 Hz), 7.67(t, 1H, J=7.9 Hz), 8.54(d, 1H, J=4.5 Hz)
IR(KBr): 3346, 2919, 2849, 1693, 1543, 1467, 1263 cm$^{-1}$
Mass(FAB, m/z): 546 (M$^+$+1)

(c) 2-[[N-Acetyl-N-[[[1-[[(octadecylcarbamoyl)oxy]methyl]-1-cyclobutyl]methoxy]carbonyl]amino]methyl pyridine

[Structure: cyclobutane with -CH2-OCNHC18H37 and -CH2-OC(=O)N(COCH3)-CH2-pyridyl]

Following the procedure described in example 1e, but replacing the compound prepared in example 1d with the compound prepared in example 14b, the desired compound was obtained. (85% yield).

$^1$H-NMR(300 MHz, CDCl$_3$): δ0.88 (t, 3H, J=6.5 Hz), 1.20–1.60(m, 32H), 1.60–1.70 (m, 4H), 1.70–1.90(m, 2H), 2.65(s, 3H), 3.12–3.17(m, 2H), 3.90(s, 2H), 4.12(s, 2H), 5.10(s, 2H), 5.19(br t, 1H), 7.10(d, 1H, J=8.4 Hz), 7.13(d, 1H, J=5.3 Hz), 7.62(t, 1H, J=7.7 Hz), 8.48(d, 1H, J=4.5 Hz)
Mass(FAB, m/z): 588 (M$^+$+1)

(d) Preparation of the title compound of this example

Following the procedure described in example 1f, but replacing the compound prepared in example 1e with the compound prepared in example 14c, the title compound of this example was obtained as a yellow solid (80% yield).

mp: 41.8°–43.6° C.
$^1$H-NMR(300 MHz, CDCl$_3$): δ0.88(t, 3H, J=6.8 Hz), 1.25–1.55(m, 32H), 1.73(t, 3H, J=7.3 Hz), 1.85(d, 4H, J=5.6 Hz), 1.96–2.15(m, 2H), 2.65(s, 3H), 3.07–3.14(m, 2H), 3.97(s, 2H), 4.33(s, 2H), 4.94(br t, 1H), 5.06(q, 2H, J=7.2 Hz), 5.45(s, 2H), 7.89(d, 1H, J=7.8 Hz), 8.07(t, 1H, J=6.2 Hz), 8.52(t, 1H, J=7.9 Hz), 9.84(d, 1H, J=6.1 Hz)
IR(KBr): 3349, 2920, 2850, 1745, 1689, 1630, 1525, 1342, 1222, 773 cm$^{-1}$
Mass(FAB, m/z): 616(M$^+$–I)

Example 15–18

Following the same procedure as described in Example 13, but replacing 1,1-bis-hydroxymethyl) cyclobutane as the starting compound with 1,1-bis-(hydroxymethyl) cycloprane(Example 15), 1,1-bis-(hydroxymethyl) cyclopentane(Example 16), 1,1-bis-cyclopropane cyclohexane(Example 17), and 1,1-bis-(hydroxymethyl) cycloheptane (Example 18), the corresponding title compounds were obtained in similar overall yields.

Example 15

2-[[N-Acetyl-N-[[[1-[[(octadecylcarbamoyl)oxy]methyl]-1-cyclopropyl]methoxy]carbonyl]amino]methyl]-1-ethyl-pyridinium iodide

[Structure: cyclopropane with -CH2-OCNHC18H37 and -CH2-OC(=O)N(COCH3)-CH2-pyridinium ethyl, I-]

mp: 38.5°–45.5° C.

$^1$H-NMR(300 MHz, CDCl$_3$): δ0.67(s, 4H), 0.88(t, 3H, J=6.9), 1.20–1.35(m, 30H), 1.35–1.55(m, 2H), 1.75(t, 3H, J=7.32 Hz), 2.67(s, 3H), 3.11 (q, 2H, J=6.7 Hz), 3.84(s, 2H), 4.20(s, 2H), 4.95–5.10(m, 1H), 5.10(q, 2H, J=7.3 Hz), 5.46(s, 2H), 7.80(d, 1H, J=7.8 hz), 8.07(t, 1H, J=7.1 Hz), 8.54(t, 1H, J=7.9 Hz), 9.65(d, 1H, J=6.0 Hz)

IR(KBr): 3334, 2922, 2852, 1744, 1695, 1530, 1326, 1227, 1152, 1013, 768, cm$^{-1}$

Mass(FAB, m/z): 602(M$^+$–I)

Example 16

2-[[N-Acetyl-N-[[[1-[[(octadecylcarbamoyl)oxy]methyl]-1-cyclopentyl]methoxy]carbonyl]amino]methyl]-1-ethyl-pyridinium iodide

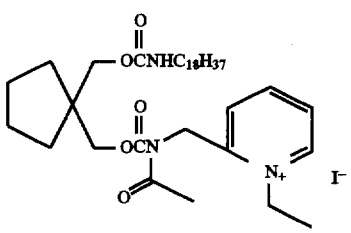

mp: 45.1°–55.8° C.

¹H-NMR(300 MHz, CDCl₃): δ0.88(t, 3H, J=6.9 Hz), 1.20–1.35(m, 30H) 1.35–1.50(m, 6H), 1.50–1.68m, 4H), 1.75(t, 3H J=7.3 Hz), 2.66(s, 3H), 3.05–3.24(m, 2H), 3.60(s, 2H) 4.17(s, 2H), 4.90–5.01(m, 1H), 5.05(q, 2H, J=7.1 Hz), 5.44(s, 2H), 7.92(d, 1H J=7.8 Hz), 8.09(t, 1H, J=6.5 Hz), 8.54(t, 1H, J=7.6 Hz), 9.65(d, 1H, J=5.5 Hz)

IR(KBr): 3401, 2920, 2851, 1720, 1701, 1629, 1526, 1462, 1344, 1226, 1159, 774, cm⁻¹

Mass(FAB, m/z): 630(M⁺–I)

Example 17

2-[[N-Acetyl-N-[[[1-[[(octadecylcarbamoyl)oxy]methyl]-1-cyclohexyl]methoxy]carbonyl]amino]methyl]-1-ethyl-pyridinium iodide

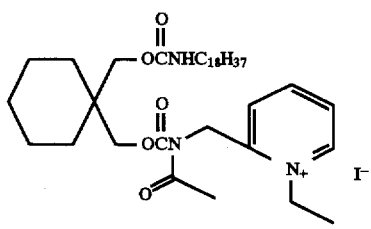

mp: 74.5°–78.5° C.

¹H-NMR(300 MHz, CDCl₃): δ0.88(t, 3H, J=6.9 Hz), 1.20–1.35(m, 30H), 1.35–1.50(m, 8H), 1.50–1.68(m, 4H), 1.75(t, 3H, J=7.3 Hz), 2.66(s, 3H), 3.05–3.20 (m, 2H), 3.60 (s, 2H), 4.17(s, 2H), 4.90–5.01(m, 1H), 5.05(q, 2H, J=7.1 Hz), 5.44(s, 2H), 7.92(d, 1H, J=7.8 Hz), 8.09(t, 1H, J=6.5 Hz), 8.54(t, 1H, J=7.6 Hz), 9.65(d, 1H, J=5.5 Hz)

IR(KBr): 3401, 2920, 2851, 1720, 1701, 1629, 1526, 1462, 1344, 1226, 1159, 774, cm⁻¹

Mass(FAB,m/z): 644(M⁺–I)

Example 18

2-[[N-Acetyl-N-[[[1-[[(octadecylcarbamoyl)oxy]methyl]-1-cycloheptyl]methoxy]carbonyl]amino]methyl]-1-ethyl-pyridinium iodide

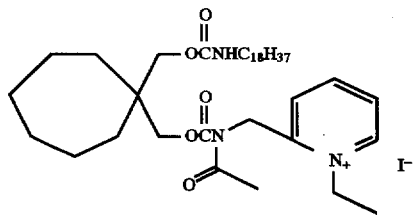

mp: 93.7–99.8° C.

¹H-NMR(300 MHz, CDCl₃): δ0.88(t, 3H, J=6.9 Hz), 1.19–1.65(m, 44H), 1.75(t, 3H, J=7.3 Hz), 2.65(s, 3H), 3.07–3.09(m, 2H), 4.09(s, 2H), 5.00–5.10(m, 3H), 5.42(s, 2H), 7.89(d, 1H, J=7.8 Hz), 8.08(t, 1H, J=6.6 Hz), 8.50(t, 1H, J=7.8 Hz), 9.67(d, 1H, J=6.1 Hz)

IR(KBr): 3311, 2922, 2853, 1747, 1705, 1630, 1524, 1457, 1364, 1230, 1167, 1088, 977 cm⁻¹

Mass(FAB, m/z): 658(M⁺–I)

Example 19 trans-2-[[N-Acetyl-N-[[[3-[[(octadecylcarbamoyl)oxy]methyl]-1-cyclobutyl]methoxy]carbonyl]amino]methyl]-1-ethyl-pyridinium iodide

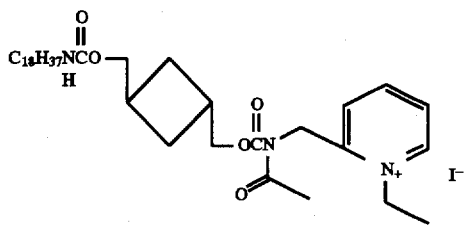

Following the same procedure as described in Example 13, but replacing 1,1-bis-(hydroxymethyl) cyclobutane as the starting compound with tans-1,3-bis-(hydroxymethyl) cyclobutane, the title compound of this example was obtained as a light yellow solid in a similar overall yield.

mp: 50.4°–58.8° C.

¹H-NMR(300 MHz, CDCl₃): δ0.88(t, 3H, J=6.9 Hz), 1.18–1.60(m, 32H), 1.74(t, 3H, J=7.3 Hz), 1.81–1.98(m, 4H), 2.50–2.74(m, 5H), 3.14(q, 2H, J=6.0 Hz), 4.05(d, 2H, J=6.5 Hz), 4.35(d, 2H, J=7.5 Hz), 4.88(br s, 1H), 5.07(q, 2H, J=7.4 Hz), 5.42(s, 2H), 7.70(d, 1H, J=8.0 Hz), 8.03–8.08(m, 1H), 8.46(t, 1H, J=8.0 Hz), 9.66(d, 1H J=5.8 Hz)

IR(KBr): 3365, 2919, 2850, 1739, 1696, 1528, 1358, 1220, 775 cm⁻¹

Mass(FAB, m/z): 616(M⁺–I)

Example 20

2-[[N-Acetyl-N-[[[1-[[(hexadecylcarbamoyl)oxy]methyl]-1-cyclopentyl]methoxy]carbonyl]amino]methyl]-1-ethyl-pyridinium iodide

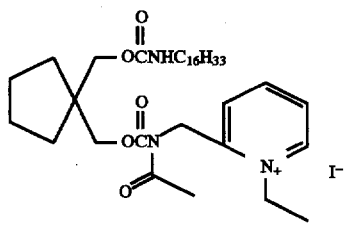

(a) 1,1-Bis-[[(phenoxycarbonyl)oxy]methyl]cyclobutane

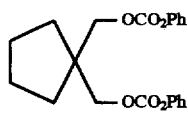

Following the procedure described in example 8a, but replacing the compound prepared in example 6b with 1,1-bis-(hydroxy methyl) cyclopentane, the desired compound was obtained as a white solid (95% yield).

¹H-NMR(80 MHz, CDCl₃): δ1.32–1.67(m, 8H), 3.9(s, 4H), 7.25–7.43(m, 10H)

(b) 2-[[N-[[[1-[[(Hexadecylcarbamoyl)oxy]methyl]-1-cyclopentanyl]methoxy]carbonyl]amino]methyl]pyridine

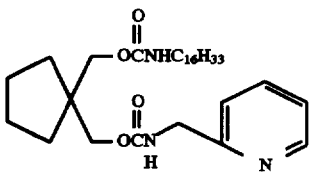

Following the procedure described in example 8b, but replacing the compound prepared in example 8a with the compound prepared in example 20a, the desired compound was obtained as a white solid (35% yield).

mp: 54.7°–56.2° C.

$^1$H-NMR(80 MHz, CDCl$_3$): δ0.88(t, 3H, J=6.8 Hz), 1.10–1.80(m, 36H), 3.00–3.25(m, 2H), 3.93(s, 2H), 3.98(s, 2H), 4.47(d, 2H, J=5.5 Hz), 4.75–5.00(m, 1H), 5.90–6.10(m, 1H), 7.05–7.30(m, 2H), 7.50–7.68(m, 1H), 8.52(d, 1H, J=4.8 Hz)

IR(KBr): 3338, 2919, 2851, 1691, 1547, 1468, 1434, 1258, 1155, 1033, 996 cm$^{-1}$ (c) 2-[[N-Acetyl-N-[[[1-[[(hexadecylcarbamoyl)oxy]methyl]-1-cyclopentanyl]methoxy]carbonyl]amino]methyl]pyridine

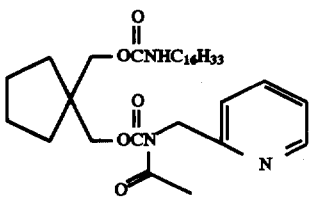

Following the procedure described in example 8c, but replacing the compound prepared in example 8b with the compound prepared in example 20b, the desired compound was obtained as a light yellow oil. (80% yield).

$^1$H-NMR(80 MHz, CDCl$_3$): δ0.88(t, 3H, J=6.9 Hz), 1.10–1.70(m, 36H), 2.65(s, 3H), 3.00–3.20(m, 2H), 3.73(s, 2H), 4.00(s, 2H), 5.11(s, 2H), 5.10–5.20(m, 1H), 7.05–7.25 (m, 2H), 7.52–7.70(m, 1H), 8.51 (d, 1H, J=4.5 Hz)

IR(neat):3343, 2927, 2853, 1740, 1710, 1629, 1521, 1457, 1374, 1294, 1224, 1162, 981 cm$^{-1}$ (d) Preparation of the title compound of this example Following the procedure described in example 1f, but replacing the compound prepared in example 1e with the compound prepared in example 20c, the title compound of this example was obtained as a yellow solid (70% yield).

$^1$H-NMR(300 MHz, CDCl$_3$): δ0.88(t, 3H, J=6.3 Hz), 1.26–1.64(m, 36H), 1.77(t, 3H, J=7.2 Hz), 2.66(s, 3H), 3.06–3.13(m, 2H), 3.81(s, 2H), 4.17 (s, 2H), 4.93(br s, 1H), 5.08(q, 2H, J=7.5 Hz), 5.44(s, 2H), 7.88–7.95(m, 1H), 8.10(t, 1H, J=7.7 Hz), 8.53(t, 1H, J=7.9 Hz), 9.71(d, 1H, J=6.1 Hz)

IR(KBr): 3346, 2926, 2853, 1743, 1712, 1593, 1529, 1465, 1354, 1289, 1213, 1153, 1078 cm$^{-1}$

Example 21

N-[4-[[[1-[[(Octadecylcarbamoyl)oxy]methyl]1-cyclopentyl]methoxy]carbonyl]butyl]pyridinium bromide

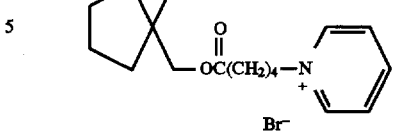

(a) 1-[[(N-Octadecylcarbamoyl)oxy]methyl]cyclopentane-1-methanol

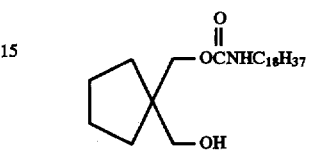

Following the procedure described in example 14a, but replacing 1,1-bis(hydroxymethyl) cyclobutane with 1,1-bis(hydroxy methyl)cyclopentane, the desired compound was obtained as a white solid (89% yield).

mp: 60.4°–61.7° C.

$^1$H-NMR(80 MHz, CDCl$_3$): δ0.77(t, 3H, J=7.0 Hz), 1.01–1.24(m, 32H), 1.39–1.71(m, 8H), 2.96–3.17(m, 2H), 3.26(s, 2H), 3.98(s, 2H), 4.50–4.80(m, 1H)

IR(KBr): 3318(br), 2920, 2850, 1684, 1552, 1468, 1272, 1151, 1045, 718 cm$^{-1}$

Mass(FAB, m/z): 426 (M $^+$+1)

(b)[1-[[(N-Octadecylcarbamoyl)oxy]methyl]-1-cyclopentyl]methyl-5-bromopentanoate

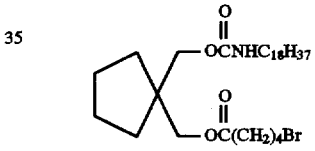

To a cold (0° C.) stirred solution of the compound prepared in example 21a (425 mg) in methylene chloride(15 ml) was added pyridine(0.097 ml) and then 5-bromo pentanoyl chloride (0.166 ml), and the mixture was allowed to warm to room temperature. After stirring for 3 hrs, the reaction mixture was diluted with ethyl acetate, washed with water. The organic layer was concentrated under reduced pressure and the resulting residue purified by flash chromatography on silica gel (ethyl acetate:hexane=1:5) to afford 525 mg of the desired product as a white solid (89% yield).

mp: 44.8°–45.7° C.

$^1$H-NMR(80 MHz, CDCl$_3$): δ0.88(t, 3H, J=6.9 Hz), 1.10–1.70(m, 40H), 1.71–200(m, 4H), 2.05–2.45(m, 2H), 3.02–3.20(m, 2H), 3.20–3.49(m, 2H), 3.95(s, 4H), 4.40–4.60 (m, 1H)

IR(KBr): 3384, 2919, 2849, 1731, 1699, 1521, 1468, 1392, 1276, 1176, 1028, 779 cm$^{-1}$ (c) Preparation of the title compound of this example The above-described compound (100 mg) was dissolved in dry pyridine (0.5 ml) and heated at 100° C. for 16 hrs. After removal of excess pyridine under reduced pressure, the residue obtained was purified by flash chromatography on silica gel (chloroform:methanol=10:1) to afford 80 mg of the title compound as a yellow solid (71% yield).

mp: 54.5°–56.2° C.

$^1$H-NMR(300 MHz, CDCl$_3$): δ0.86(t, 3H, J=6.3 Hz), 1.23–1.78(m, 42H), 2.07–2.14(m, 2H), 2.40(t, 2H, J=6.9

Hz), 3.07–3.14(m, 2H); 3.88(s, 2H), 3.91(s, 2H), 4.77(brs, 1H), 5.06(t, 2H, J=7.2 Hz), 8.07(t, 2H, J=6.6 Hz), 8.45(t, 1H, J=7.5 Hz), 9.55(d, 2H, J=5.1 Hz)

IR(KBr): 3326, 2919, 2851, 1726, 1700, 1547, 1473, 1260, 1171, 1048, 780, 681 cm$^{-1}$

Mass(FAB, m/z): 587 (M$^+$–Br)

Example 22

3-[4-[[[1-[[(Octadecylcarbamoyl)oxy]methyl]-1-cyclopentyl]methoxy]carbonyl]butyl]thiazolium bromide.

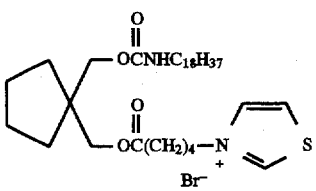

The compound prepared in example 21b(200 mg) was dissolved in thiazole (0.5 ml) and heated at 100° C. for 18 hrs. After removal of excess thiazole under reduced pressure, the residue obtained was purified by flash chromatography on silica gel (chloroform:methanol=10:1) to afford 189 mg of the title compound as a yellow solid. (83% yield).

mp: 54.2°–56.5° C.

$^1$H-NMR(300 MHz, CDCl$_3$): δ0.88(t, 3H, J=6.7 Hz), 1.25–1.78(m, 42H), 2.07–2.14(m, 2H), 2.42(t, 2H, J=6.9 Hz), 3.10–3.16(m, 2H), 3.92(s, 2H), 3.94(s, 2H), 4.82(br s, 1H), 4.85–4.95(m, 2H), 8.23 (br s, 1H), 8.58(br s, 1H), 11.36(br s, 1H)

IR(KBr): 3325, 2919, 2850, 1724, 1692, 1541, 1465, 1385, 1260, 1163, 1036, 834, 722, 635 cm$^{-1}$

Mass(FAB, m/z): 593 (M$^+$–Br)

Example 23

N-[4-[[[1-[[(Octadecylcarbamoyl)oxy]methyl]1-cyclopentyl]methoxy]carbonyl]butyl]quinolinium bromide

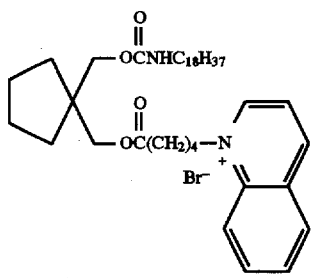

The compound prepared in example 10a(100 mg) was dissolved in quinoline (1 ml) and heated at 50° C. for 8 hrs. After removal of excess quinoline under reduced pressure, the residue obtained was purified by flash chromatography on silica gel (chloroform:methanol=10:1) to afford 72 mg of the title compound as a purple solid. (60% yield).

mp: 56.2°–59.2° C.

$^1$H-NMR(300 MHz, CDCl$_3$): δ0.84(t, 3H, J=6.7 Hz), 1.25–1.88(m, 42H), 2.15–222(m, 2H), 2.41(t, 2H, J=6.9 Hz), 3.05–3.16(m, 2H), 3.85(s, 2H), 3.87(s, 2H), 4.82(br s, 1H), 5.44(m, 2H), 7.93(t, 1H, J=7.6 Hz), 8.15–8.23(m, 2H), 8.37(d, 1H, J=7.5 Hz), 8.48 (d, 1H, J=8.7 Hz), 9.14(d, 1H, J=8.4 Hz), 10.45(br s, 1H)

IR(KBr): 3326, 2918, 2850, 1724, 1693, 1533, 1465, 1379, 1256, 1168, 1038, 819, 777, 722 cm$^{-1}$

Mass(FAB, m/z): 637 (M$^+$–Br)

Example 24

1-[[(N-Octadecylcarbamoyloxy)methyl]cyclopentan-1-yl] methyl 2-pyridinioethyl phosphate (Inner salt)

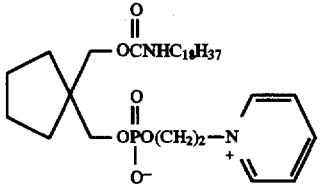

(a) 1-[[(N-Octadecylcarbamoyloxy)methyl]cyclopentan-1-yl]methyl 2-bromoethyl phosphate

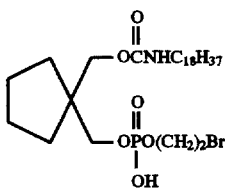

To a cold (0° C.) stirred solution of the compound prepared in example 21a (150 mg) in dry methylene chloride(2 ml) was added slowly dry triethyl amine(0.1 ml) and then a freshly prepared 2-bromoethyl phosphodichloridate (127 mg), and the mixture was allowed to warm to room temperature. After stirring for 12 h, the reaction mixture was diluted with methylene chloride and washed with water. The organic layer was dried, concentrated under reduced pressure and the resulting residue purified by flash chromatography on silica gel (chloroform:methanol=8:1) to afford 214 mg of the desired product as a white solid(85% yield).

mp: 108.0°–110.9° C.

$^1$H-NMR(300 MHz, CDCl$_3$): δ0.87(t, 3H, J=6.9 Hz), 1.10–1.71(m, 40H), 2.95–3.15(m, 2H), 3.53(t, 2H, J=6.0 Hz), 3.60–4.25(m, 6H), 5.20–5.40 (m, 1H), 6.70–6.80(m, 1H)

IR(KBr): 3329, 2925, 2583, 2696, 1526, 1461, 1237, 1068, 909, 803 cm$^{-1}$

Mass(FAB, m/z): 612 (M$^+$)

(b) Preparation of the title compound of this example

A mixture of the above-described compound (154 mg) and dry pyridine(0.2 ml) was heated at 80° C. overnight. The reaction mixture was then treated with methanol(5 ml) solution of silver carbonate(250 mg) and stirred for 2 h at room temperature. After filteration and concentration of the filtrate under reduced pressure, the residue obtained was purified by flash chromatography on silica gel (chloroform:methanol:water=65:25:4) to afford 82 mg of the desired product (54% yield).

mp: 105.5°–115.8° C.

$^1$H-NMR(300 MHz, CD$_3$OD): δ0.89(t, 3H, J=6.9 Hz), 1.20–1.65(m, 40H), 3.09(t, 2H, J=7.2 Hz), 3.67(d, 2H, J=4.3 Hz), 3.89(s, 2H), 4.20–4.30 (m, 2H), 4.80(m, 2H), 8.07(t, 2H, J=6.9 Hz), 8.54(t, 1H, J=7.9 Hz), 8.96(d, 2H, J=6.0 Hz)

IR(KBr): 3375, 2918, 2851, 1694, 1526, 1473, 1239, 1085, 1052, 925, 850, 750, 681, cm$^{-1}$

Mass(FAB, m/z): 611 (M$^+$+1)

Example 25

1-[[(N-Octadecylcarbamoyloxy)methyl]cyclopentan-1yl] methyl 2-thiazolioethyl phosphate (Inner salt)

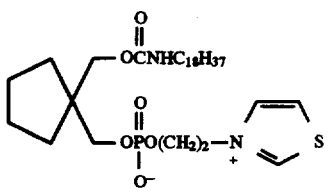

Following the procedure described in example 24b, the compound obtained in example 24a was reacted with thiazole to afford the title compound of this example(54% yield).

mp: 69.3°–75.5° C.

$^1$H-NMR(300 MHz, CDCl$_3$+trace DMSO-d$_6$): δ0.88(t, 3H, J=6.9 Hz), 1.20–1.70(m, 40H), 3.01–3.09(m, 2H), 3.67 (d, 2H, J=4.2 Hz), 3.91(s, 2H), 4.20–4.30(m, 2H), 4.93(s, 2H), 6.20–6.30(m, 1H), 8.23(s, 1H), 8.64(s, 1H), 10.71(s, 1H)

IR(KBr): 3329, 2920, 2851, 1701, 1540, 1468, 1244, 1063, 945, 846, 533 cm$^{-1}$

Mass(FAB, m/z): 618 (M$^+$+2)

Example 26

1-[[(N-Octadecylcarbamoyloxy)methyl]cyclopentan-1yl]methyl 2-quinolinioethyl phosphate (Inner salt)

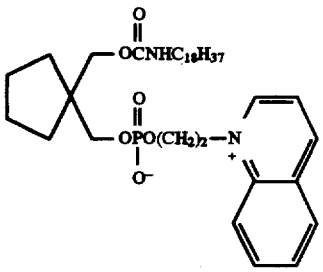

Following the procedure described in example 24b, the compound obtained in example 24a was reacted with quinoline to afford the title compound of this example(50% yield).

$^1$H-NMR(300 MHz, CDCl$_3$): δ0.89(t, 3H, J=6.9 Hz), 1.20–1.70(m, 40H), 3.01–3.09(m, 2H), 3.57(d, 2H, J=4.3Hz), 3.80(s, 2H), 4.38–4.45(m, 2H), 5.35(t, 2H, J=4.8 Hz), 8.03(t, 2H, J=7.5 Hz), 8.15(dd, 1H, J=8.4 Hz, J=5.9 Hz), 8.27(t, 1H, J=7.0 Hz), 8.38 (d, 1H, J=8.0 Hz), 8.57(d, 1H, J=9.0 Hz), 9.15(d, 1H, J=8.3 Hz), 9.45(d, J=5.6 Hz)

Example 27 trans-2-[[N-Acetyl-N-[[[4-[[(octadecylcarbamoyl)oxy]methyl]-2-thietanyl]methoxy]carbonyl]amino]methyl]-1-ethyl-pyridinium chloride

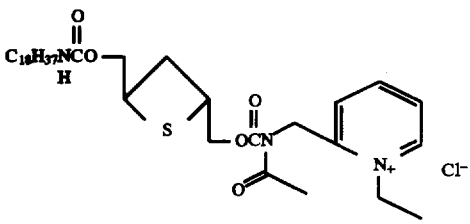

(a) trans-2,4-Bis[(carbomethoxy)methyl]thietane and its cis isomer

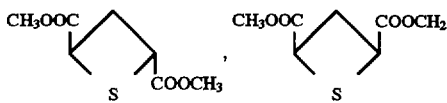

To a stirred solution of 2,4-dibromoglutarate(15.30 g)in methylene chloride(120 ml) was added slowly sodium sulfide (11.50 g) in dry dimethyl sulfoxide(80 ml) at –30° C. The mixture was stirred for 1 h, and concentrated under reduced pressure, diluted with ethyl acetate and washed with an ice-cold water. The organic layer was dried, concentrated under reduced pressure and the resulting residue purified by flash chromatography on silica gel (ethyl acetate:hexane= 1:9) to afford 2.50 g of trans isomer and 2.40 g of cis isomer as a colorless oil (51% yield).

trans isomer; $^1$H-NMR(300 MHz, CDCl$_3$): δ3.31(t, 2H, J=7.3 Hz), 3.77(s, 6H), 4.13(t, 2H, J=7.4 Hz)

Mass(EI, m/z): 190(M$^+$)

cis ismer; $^1$H-NMR(300 MHz, CDCl$_3$): δ3.05 (dt, 1H, J=12.9 Hz, J=8.7 Hz), 3.61(dt, 1H, J=12.9 Hz, J=7.5 Hz), 3.75(s, 6H), 4.13(t, 2H, J=7.9 Hz)

Mass(EI, m/z): 190(M$^+$)

(b) trans-2,4-Bis-(hydroxymethyl)thietane

To a stirred solution of the above-described compound (1.50 g) in dry ethyl ether(50 ml) was added lithium borohydride(0.35 g), and the mixture was stirred at room temperature overnight. The reaction was quenched by adding an ice-cold water(5 ml), and the aqueous layer was extracted with ethyl acetate. The combined organic layer was dried, concentrated under reduced pressure, and the resulting residue purified by flash chromatography on silica gel (ethyl acetate:hexane=2:1) to afford 0.93 g of the desired product as a white solid(88% yield).

$^1$H-NMR(300 MHz, CDCl$_3$): δ2:13(br s, 2H), 2.77(t, 2H), 3.71(m, 6H)

IR(KBr): 3220, 2940, 2830, 1462, 1309, 1242, 1040, 981, 701 cm$^{-1}$ (c) trans-2,4-Bis-[[(phenoxycarbonyl)oxy]methyl]thietane

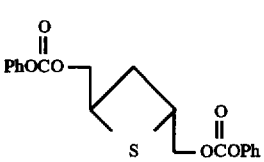

Following the procedure described in example 8a, the diol compound prepared in example 27b (0.81 g) in methylene chloride(20 ml) was reacted with two equivalents of phenyl chloro formate(1.70 ml) in the presence of pyridine (1.3 ml) to afford 2.0 g of the desired compound as a white solid(88% yield).

$^1$H -NMR(80 MHz, CDCl$_3$): δ2.88 (t, 2H,J=7.2 Hz), 3.86(q, 2H, J=6.8 Hz), 4.42 (dd, 2H, J=11.0 Hz, J=6.1 Hz), 4.53(dd, 2H, J=11.3 Hz, J=6.9 Hz), 7.17–7.41 (m, 10H)

IR(KBr): 2952, 1761, 1492, 1386, 1232, 1061, 964, 772 cm$^{-1}$ (d) tans-2-[[N-[[[4-[[(Octadecylcarbamoyl)oxy]methyl]-2-thietanyl]methoxy]carbonyl]amino]methyl]pyridine

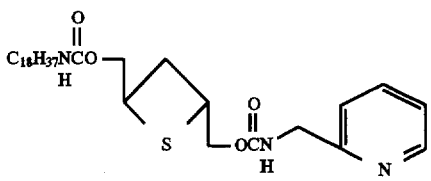

Following the procedure described in example 8b, but replacing the compound prepared in example 8a with the compound prepared in example 27c, the desired compound was obtained as a white solid(46% yield).

mp: 121.3°–122.1° C.

$^1$H-NMR(300 MHz, CDCl$_3$): δ0.88(t, 3H, J=6.9 Hz), 1.20–1.40(m, 30H), 1.40–1.60(m, 2H), 2.71(app t, 2H, J=7.0 Hz), 3.15 (q, 2H, J=6.4 Hz), 3.67–3.76(m, 2H), 4.16–4.26 (m, 2H), 4.28–4.43(m, 2H), 4.49(d, 2H, J=5.2 Hz), 4.69(br s, 1H), 5.85(br s, 1H), 7.17–7.28(m, 2H), 7.66(t, 1H, J=7.7 Hz), 8.53(d, 1H, J=5.0 Hz)

IR(KBr): 3324, 2921, 2851, 1686, 1539, 1463, 1258, 1144, 1050, 647 cm$^{-1}$ (e) trans-2-[[N-Acetyl-N-[[[4-[[(octadecylcarbamoyl)oxy]methyl]-2-thietanyl]methoxy]carbonyl]-amino]methyl]pyridine

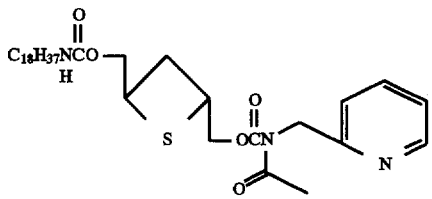

Following the procedure described in example 1e, but replacing the compound prepared in example 1d with the compound prepared in example 27d, the desired compound was obtained as a white solid(88% yield).

$^1$H-NMR(300 MHz, CDCl$_3$): δ0.88(t, 3H, J=6.4 Hz), 1.20–1.40(m, 30H), 1.40–1.60(m, 2H), 2.47–2.55(m, 2H), 2.62(s, 3H), 3.13(q, 2H, J=6.4 Hz), 3.54–3.61(m, 2H), 4.12–4.43(m, 4H), 4.80(br s, 1H), 5.08(s, 2H), 7.09–7.15(m, 2H), 7.60(app t, 1H, J=7.7 Hz), 8.49(d, 1H, J=4.9 Hz)

(f) preparation of the title compound of this example

A mixture of the compound prepared in example 27e (109 mg) and ethyl iodide(0.5 ml) was heated at 80° C. in acetonitrile(0.5 ml) for 10 h, while shielded from light. The mixture was concentrated under reduced pressure, and the resulting crude was eluted through the column packed with IRA -410 resin (5 g, Cl form) using the eluent (methanol:water=7:3). The residue obtained after evaporation of the solvent was then purified by flash chromatography on silica gel (methanol:methylene chloride=1:10) to afford 94 mg of the title compound of this example as a light yellow solid(78% yield).

mp: 51.9°–54.7° C.

$^1$H-NMR(300 MHz, CDCl$_3$): δ0.88(t, 3H, J=6.5 Hz), 1.20–1.60(m, 32H), 1.73(t, 3H, J=7.2 Hz), 2.66–2.72(m, 5H), 3.10–3.22(m, 2H), 3.50–3.80 (m, 2H), 4.12–4.56(m, 4H), 5,10–5.40(m, 3H), 5.48(s, 2H), 7.65(d, 1H, J=8.0 Hz), 8.00–8.15(m, 1H), 8.39(t, 1H, J=8.3 Hz), 9.99(d, 1H, J=4.8 Hz)

IR(KBr): 3385, 2920, 2851, 1744, 1694, 1631, 1530, 1357, 1226, 988, 775 cm$^{-1}$

Mass(FAB, m/z): 634(M$^+$–Cl)

Example 28 cis-2-[[N-Acetyl-N-[[[4-[[(octadecylcarbamoyl)oxy]methyl]-2-thietanyl]methoxy]carbonyl]amino]methyl]-1-ethyl-pyridinium chloride

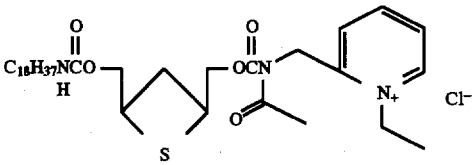

(a) cis-2,4-Bis-(hydroxymethyl)thietane

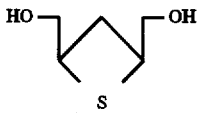

Following the procedure described in example 27b, but replacing the compound prepared in example trans-27a with the compound prepared in example cis-27a, the desired compound was obtained as a white solid (70% yield).

$^1$H-NMR(80 MHz, CDCl$_3$): δ2.45–3.08(m, 4H), 3.44–3.94(m, 6H)

IR(KBr): 3346(br), 2925, 2858, 1648, 1461, 1357, 1060, 1016, 838 cm$^{-1}$ (b) cis-2,4-Bis-[[(phenoxycarbonyl)oxy]methyl]thietane

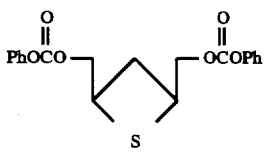

Following the procedure described in example 27c, but replacing the compound prepared in example 27b with the compound prepared in example 28a, the desired compound was obtained as a white solid (82% yield).

$^1$H-NMR(80 MHz, CDCl$_3$): δ2.33–3.33(m, 2H), 3.72–4.65(m, 6H), 7.09–7.51(m, 10H)

(c) cis-2-[[N-[[[4-[[(Octadecylcarbamoyl)oxy]methyl]-2-thietanyl]methoxy]carbonyl]amino]methyl]pyridine

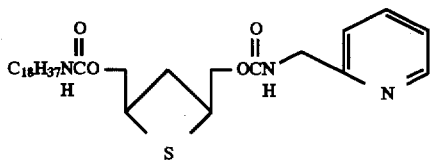

Following the procedure described in example 27d, but replacing the compound prepared in example 27c with the compound prepared in example 28b, the desired compound was obtained as a light yellow solid (37% yield)

mp: 103.4°–10.6.3° C.

$^1$H-NMR(300 MHz, CDCl$_3$): δ0.88(t, 3H, J=6.6 Hz), 1.15–1.55(m, 32H) 2.40–2.44(m, 1H), 2.97–3.01(m, 1H), 3.10–3.20(m, 2H), 3.75–3.79(m, 2H), 4.10–4.39(m, 4H), 4.49(d, 2H, J=4.9 Hz), 4.87(br s, 1H), 5.90(br s, 1H), 7.16–7.28(m, 2H), 7.66(t, 1H, J=7.6 Hz), 8.53(d, 1H, J=4.5 Hz)

IR(KBr): 3334, 2920, 2850, 1689, 1537, 1464, 1258, 1142, 1048, 990, 770, 639 cm$^{-1}$ (d) cis-2-[[N-Acetyl-N-[[[4-[[(octadecylcarbamoyl)oxy]

methyl]-2-thietanyl]methoxy]carbonyl]amino]methyl]
pyridine

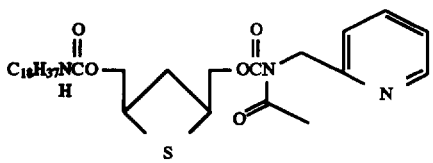

Following the procedure described in example 27e, but replacing the compound prepared in example 27d with the compound prepared in example 28c, the desired compound was obtained as a white solid (89% yield).

mp: 64.4°–67.2° C.

$^1$H-NMR(300 MHz, CDCl$_3$): δ0.88(t, 3H, J=6.6 Hz), 1.21–1.55(m, 32H), 2.20–2.29(m, 1H), 2.62(s, 3H), 2.73–2.80(m, 1H), 3.12–3.18(m, 2H), 3.63–3.75(m, 2H), 3.96–4.40(m, 4H), 4.87(br s, 1H), 5.10(s, 2H), 7.09–7.16(m, 2H), 7.62(t, 1H, J=7.6 Hz), 8.50(d, 1H, J=4.8 Hz)

IR(KBr): 3347, 2920, 2850, 1734, 1695, 1529, 1469, 1304, 1216, 1153, 1084, 1040, 981 cm$^{-1}$ (e) preparation of the title compound of this example Following the procedure described in example 27f, but replacing the compound prepared in example 27e with the compound prepared in example 28d, the title compound of this example was obtained as a white solid (73% yield).

$^1$H-NMR(300 MHz, CDCl$_3$): δ0.88(t, 3H, J=6.6 Hz), 1.21–1.57(m, 32H), 1.72(t, 3H, J=6.8 Hz), 2.23–2.45(m, 1H), 2.65(s, 3H), 2.93–3.20(m, 3H), 3.59–4.05(m, 3H), 4.14–4.57(m, 3H), 5.10–5.19(m, 2H), 5.47(s, 2H), 7.66–7.69(m, 1H), 8.01–8.06(m, 1H), 8.42(t, 1H, J=7.8 Hz), 9.78(d, 1H, J=6.2 Hz)

IR(KBr): 3367, 2919, 2850, 1736, 1715, 1708, 1631, 1530, 1357, 1226, 988, 774 cm$^{-1}$

Mass(FAB, m/z): 634(M$^+$–Cl)

Example 29 trans-2-[[N-Acetyl-N-[[[4-[[(hexadecylcarbamoyl)oxy]methyl]-2-thietanyl]methoxy]carbonyl]amino]methyl]-1-ethyl-pyrindinium chloride

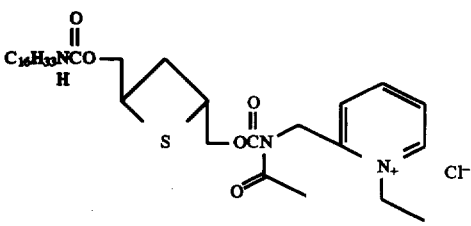

(a)trans-2-[[N-[[[4-[[(hexadecylcarbamoyl)oxy]methyl]-2-thietanyl]methoxy]carbonyl]amino]methyl]pyridine

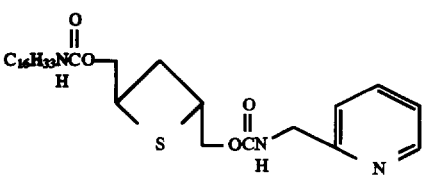

Following the procedure described in example 27d, but replacing octadecyl amine with hexadecyl amine, the desired compound was obtained as a white solid(49% yield).

mp: 118.2°–119.7° C.

$^1$H-NMR(300 MHz, CDCl$_3$): δ0.88(t, 3H, J=6.4 Hz), 1.20–1.40(m, 26H), 1.40–1.55(m, 2H), 2.71(app t, 2H, J=7.0 Hz), 3.15(q, 2H, J=6.4 Hz), 3.66–3.76(m, 2H), 4.16–4.28(m, 2H), 4.32–4.43(m, 2H), 4.49(d, 2H, J=5.2 Hz), 4.71(br s, 1H), 5.86(br s, 1H), 7.17–7.27 (m, 2H), 7.66(app t, 1H, J=7.7 Hz), 8.53(d, 1H, J=5.0 Hz)

IR(KRr): 3324, 2922, 2852, 1686, 1539, 1463, 1258, 1144, 1050, 771, 648, cm$^{-1}$ (b) trans-2-[[N-Acetyl-N-[[[4-[[(hexadecylcarbamoyl)oxy]methyl]-2-thietanyl]methoxy]carbonyl]amino]methyl]pyridine

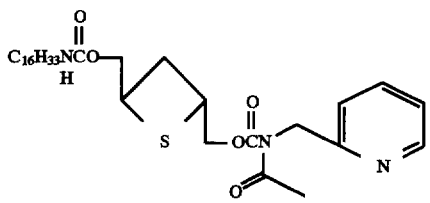

Following the procedure described in example 1e, but replacing the compound prepared in example 1d with the compound prepared in example 29a, the desired compound was obtained as a white solid(80% yield).

$^1$H-NMR(300 MHz, CDCl$_3$): δ0.88(t, 3H, J=0.65 Hz), 1.18–1.40(m, 26H), 1.40–1.55(m, 2H), 2.46–2.55(m, 2H), 2.62(s, 3H), 3.11–3.15 (m, 2H), 3.54–3.61(m, 2H), 4.13–4.43(m, 4H), 4.77(br s, 1H), 5.08 (s, 2H), 7.09–7.15 (m, 2H), 7.60(app t, 1H, J=7.8 Hz), 8.49(d, 1H, J=4.5 Hz)

IR(KBr): 3358, 2921, 2851, 1740, 696, 1527, 1459, 1384, 1341, 1221, 1149, 1074, 985 cm$^{-1}$ (c) preparation of the title compound of this example Following the procedure described in example 27f, but replacing the compound prepared in example 27e with the compound prepared in example 29b, the title compound of this example was obtained as a white solid(75% yield).

mp: 45.6°–50.4° C.

$^1$H-NMR(300 MHz, CDCl$_3$): δ0.88(t, 3H, J=6.8 Hz), 1.20–1.55(m, 28H), 1.72(t, 3H, J=7.2 Hz), 2.64–2.75(m, 5H), 3.10–3.25(m, 2H), 3.50–3.90 (m, 2H), 4.10–4.60(m, 4H), 5.10–5.30(m, 3H), 5.48(s, 2H), 7.66(d, 1H, J=7.9 Hz), 8.02–8.06(m, 1H), 8.38–8.44 (m, 1H), 9.97(d, 1H, J=4.5 Hz)

IR(KBr): 3379, 2919, 2850, 1729, 1696, 1530, 1223, 774 cm$^{-1}$

Mass(FAB, m/z): 606(M$^+$–Cl)

Example 30 trans-2-[[N-(2-Methoxy)benzoyl-N-[[[4-[[(octadecylcarbamoyl)oxy]ethyl]-2-thietanyl]methoxy]carbonyl]amino]-1-ethyl-pyridinium chloride

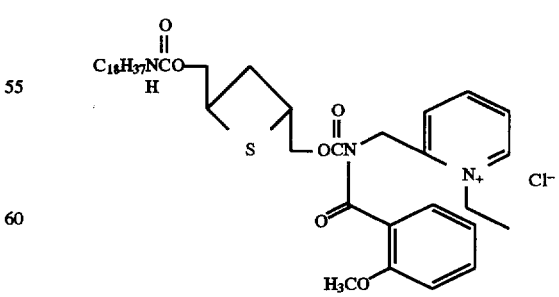

(a) trans-2-[[N-(2-methoxy)benzoyl-N-[[[4-[[(octadecylcarbamoyl)oxy]methyl]-2-thietanyl]methoxy]carbonyl]amino]methyl]pyridine

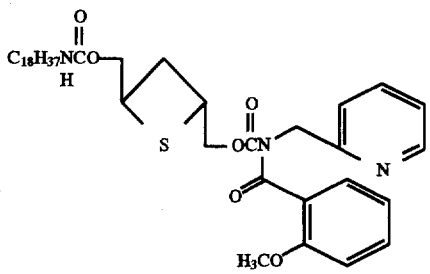

To a cold (0° C.) stirred solution of the compound prepared in example 27d(220 mg) in methylene chloride(3 ml) was added triethylamine(56 μl) and then o-methoxy benzoyl chloride (65 μl) and the mixture was allowed to warm to room temperature. After stirring overnight, the reaction mixture was diluted with methylene chloride, washed successively with 1N- HCl solution and water. The organic layer was dried, concentrated under reduced pressure, and the resulting residue purified by flash chromatography on silica gel (ethyl acetate:hexane=1:1) to afford 266 mg of the desired product as a white solid(95% yield).

$^1$H-NMR(300 MHz, CDCl$_3$): δ0.88(t, 3H, J=6.9 Hz), 1.20–1.40(m, 30H), 1.40–1.55(m, 2H), 2.28–2.33(m, 1H), 2.37–2.42(m, 1H), 3.11–3.18(m, 2H), 3.25–3.30(m, 1H), 3.84(s, 3H), 4.08–4.16(m, 2H), 4.20–4.27(d, 1H, J=8.2 Hz), 7.00(t, 1H J=7.5 Hz), 7.13–7.18(m, 1H), 7.33–7.47(m, 3H), 7.64(app t, 1H, J=7.6 Hz), 8.54(d, 1H, J=4.9 Hz)

(b)Preparation of the title compound of this example

Following the procedure described in example 27f, but replacing the compound prepared in example 27e with the compound prepared in example 30a, the desired compound was obtained as a white solid(71% yield).

mp: 55.8°–58.9° C.

$^1$H-NMR(300 MHz, CDCl$_3$): δ0.88(t, 3H, J=6.5 Hz), 1.19–1.55(m, 32H), 1.79(t, 3H, J=7.1 Hz), 2.25–2.55(m, 2H), 3.10–3.25(m, 2H), 3.30–3.55 (m, 2H), 3.92(s, 3H), 3.93–4.34(m, 4H), 5.01(br s, 1H), 5.25(q, 2H, J=7.0 Hz), 5.55(s, 2H), 6.95(d, 1H, J=8.4 Hz), 7.04–7.09(m, 1H), 7.44–7.53(m, 2H), 8.03–8.11(m, 2H), 8.41–8.47(m, 1H), 10.24(d, 1H, J=5.8 Hz)

IR(KBr): 3357, 2923, 2852, 1731, 1695, 1630, 1525, 1458, 1344, 1233, 1151, 977, 748, cm$^{-1}$

Mass(FAB, m/z): 726(M$^+$Cl)

Example 31 trans-2-[[N-(2-Methoxy)benzoyl-N-[[[4-[[(hexadecylcarbamoyl)oxy]methyl]-2-thietanyl]methoxy]carbonyl]amino]methyl]1-ethyl-pyridinium chloride

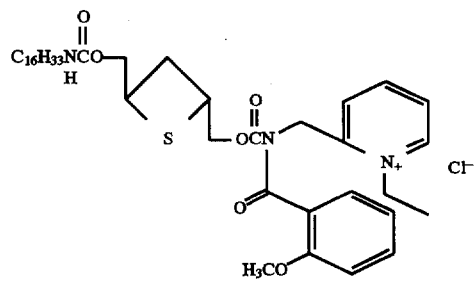

(a) trans-2-[[N-(2-Methoxy)benzoyl-N-[[[4-[[(hexadecylcarbamoyl)oxy]methyl]-2-thietanyl]methoxy]carbonyl]amino]methyl]pyridine

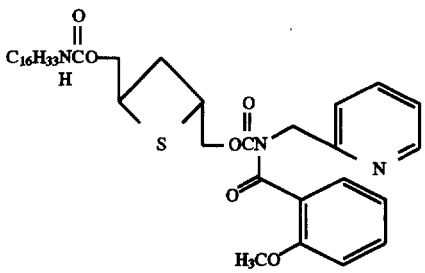

Following the procedure described in example 30a, but replacing the compound prepared in example 27d with the compound prepared in example 29a, the desired compound was obtained as a white solid(91% yield).

$^1$H-NMR(300 MHz, CDCl$_3$): δ0.88(t, 3H, J=6.9 hz), 1.20–1.40(m, 26H), 1.40–1.55(m, 2H), 2.27–2.33(m, 1H), 2.39–2.43(m, 1H), 3.11–3.15(m, 2H), 3.25–3.30(m, 1H), 3.40–3.60(m, 1H), 3.83(s, 3H), 4.07–4.26(m, 4H), 4.71(br s, 1H), 5.22(s, 2H), 6.90(d, 1H, J=8.3 Hz), 7.00(app t, 1H, J=7.2 Hz), 7.13–7.17(m, 1H), 7.33–7.47(m, 3H), 7.65(app t, 1H, J=7.6 Hz), 8.54(d, 1H, J=4.3 Hz)

(b) Preparation of the title compound of this example

Following the procedure described in example 27f, but replacing the compound prepared in example 27e with the compound prepared in example 31 a, the desired compound was obtained as a white solid(76% yield).

mp: 92.5°–93.8° C.

$^1$H-NMR(300 MHz, CDCl$_3$): δ0.88(t, 3H, J=6.6 Hz), 1.19–1.65(m, 28H), 1.79(t, 3H, J=7.3 Hz), 2.29–2.54(m, 2H), 3.05–3.20(m, 2H), 3.30–3.55 (m, 2H), 3.91(s, 3H), 4.02–4.34(m, 4H), 5.01(br s, 1H), 5.24(q, 2H, J=7.3 Hz), 5.55(s, 2H), 6.95(d, 1H, J=8.4 Hz), 7.04–7.10(m, 1H), 7.44–7.53(m, 2H), 8.03–8.11(m, 2H), 8.41–8.47(m, 1H), 10.19(d, 1H, J=6.3 Hz)

IR(KBr): 3370, 2920, 2851, 1729, 1696, 1601, 1527, 1461, 1343, 1234, 1151, 1017, 977 cm$^{-1}$

Mass(FAB, m/z): 698(M$^+$–Cl)

Example 32 trans-2-[[N-Acetyl-N-[[[4-[(hexadecyloxy)methyl]-2-thietanyl]methoxy]carbonyl]amino]methyl]-1-ethyl-pyridinium chloride

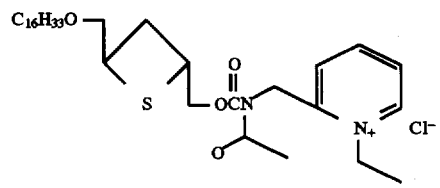

(a) trans-4-[(Hexadexyloxy)methyl]thietane-2-methanol

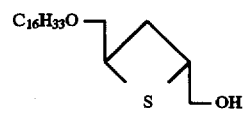

To a stirred suspension of 60% sodium hydride(230 mg), washed previously with pentane, in dry dimethyl formamide (10 ml)was added slowly trans -2,4-bis(hydroxymethyl) thietane dissolved in dry dimethyl formamide(10 ml) at 0° C. After 10 min, 1-bromohexadecane(1.4 ml)was added, and the reaction mixture was then allowed to warm to 50° C. and stirred overnight.

The reaction was quenched by adding saturated ammonium chloride solution and extracted with ethyl acetate. The organic layer was dried, concentrated under reduced pressure and the resulting residue purified by flash chromatography on silica gel (ethyl acetate:hexane=1:2) to afford 617 mg of the desired product as a white solid(51% yield).

mp: 48.7°–50.0° C.

¹H-NMR(300 MHz, CDCl₃): δ0.88(t, 3H, J=6.6 Hz), 1.21–1.39(m, 26H), 1.52–1.59(m, 2H), 2.21(br s, 1H), 2.64–2.80(m, 2H), 3.46(t, 2H, J=6.6 Hz), 3.59–3.72(m, 6H)

IR(KBr): 3307(br), 2920, 2848, 1469, 1368, 1302, 1125, 1027, 965, 718 cm⁻¹

(b) trans-2-[[N-[[[4-[(Hexadecyloxy)methyl]-2-thietanyl]methoxy]carbonyl]amino]methyl]pyridine

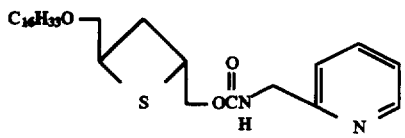

Following the procedure described in example 1d, but replacing the compound prepared in example 1c with the compound prepared in example 32a, the desired compound was obtained as a white solid(90% yield).

mp: 76.1°–77.8° C.

¹H-NMR(300 MHz, CDCl₃): δ0.88(t, 3H, J=6.6 Hz), 1.16–1.41(m, 26H), 1.51–1.58(m, 2H), 2.69(t, 2H, J=6.3H), 3.45(t, 2H, J=6.9 Hz), 3.58–3.72 (m, 4H), 4.23–4.44(m, 2H), 4.49(d, 2H, J=5.1 Hz), 5.79(br s, 1H), 7.17–7.28(m, 2H), 7.66(t, 1H, J=7.8 Hz), 8.53(d, 1H, J=4.8 Hz)

IR(KBr): 3346, 2918, 2850, 1681, 1558, 1542, 1508, 1457, 1261, 1121, 1054, 766, 719 cm⁻¹

(c) trans-2-[[N-Acetyl-N-[[[4-[(hexadecyloxy)methyl]-2-thietanyl]methoxy]carbonyl]amino]methyl]pyridine

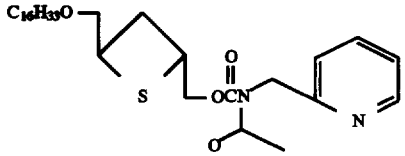

Following the procedure described in example 1e, but replacing the compound prepared in example 1d with the compound prepared in example 32b, the desired compound was obtained as a white solid(81% yield).

mp: 52.6°–55.3° C.

¹H-NMR(300 MHz, CDCl₃) δ0.88(t, 3H, J=6.6 Hz), 1.18–1.39(m, 26H), 1.52–1.56(m, 2H), 2.49–2.54(m, 2H), 2.62(s, 3H), 3.42(t, 2H, J=6.6 Hz), 3.52–3.63(m, 4H), 4.26–4.44(m, 2H), 5.08(s, 2H), 7.09–7.14(m, 2H), 7.60(t, 1H, J=7.8 Hz), 8.49(d, 1H, J=4.6 Hz)

IR(KBr): 2923, 2851, 1740; 1698, 1592, 1471, 1436, 1379, 1340, 1283, 1119, 1074, 981 cm⁻¹

(d) preparation of the title compound of this example

Following the procedure described in example 27f, but replacing the compound prepared in example 27e with the compound prepared in example 32c, the title compound of this example was obtained as a white solid(75% yield)

¹H-NMR(300 MHz, CDCl₃): δ0.88(t, 3H, J=6.6 Hz), 1.19–1.32(m, 26H), 1.53–1.62(m, 2H), 1.73(t, 3H, J=7.2 Hz), 2.50–2.75(m, 5H), 3.40–3.67 (m, 6H), 4.44–4.57(m, 2H), 5.19(q, 2H, J=7.2 Hz), 5.45(s, 2H), 7.68–7.71(m, 1H), 8.02–8.07(m, 1H), 8.36–8.47(m, 1H), 10.05(d, 1H, J=6.3 Hz)

IR(KBr): 2921, 2852, 1743, 1686, 1630, 1582, 1455, 1368, 1166, 1098, 982, 898 cm⁻¹

Mass(FAB, m/z): 563(M⁺–Cl)

Example 33 trans-2-[[N-(2-Methoxy)benzoyl-N-[[[4-[(hexadecyloxy)methyl]-2-thietanyl]methoxy]carbonyl]amino]methyl]-1-ethyl-pyridinium chloride

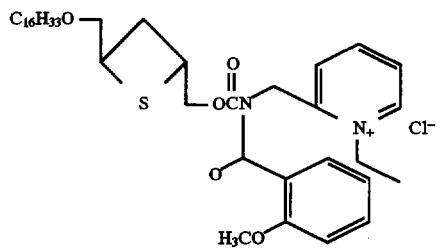

(a)trans-2-[[N-(2-Methoxy)benzoyl-N-[[[4-[(hexadecyloxy)methyl]-2-thietanyl]methoxy]carbonyl]amino]methyl]pyridine

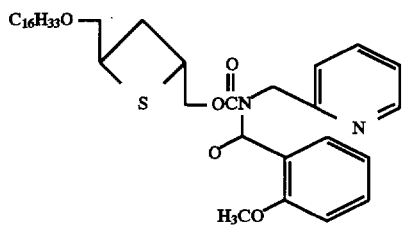

Following the procedure described in example 30a, but replacing the compound prepared in example 27d with the compound prepared in example 32b, the desired compound was obtained as a light yellow oil (79% yield).

¹H-NMR(300 MHz, CDCl₃): δ0.88(t, 3H, J=6.6 Hz), 1.20–1.32(m, 26H), 1.51–1.56(m, 2H), 2.27–2.46(m, 2H), 3.24–3.58(m, 7H), 3.84(s, 3H), 4.11–4.27(m, 2H), 5.22(s, 2H), 6.89(d, 1H, J=8.3 Hz), 7.00 (t, 1H, J=7.8 Hz), 7.13–7.47(m, 3H), 7.64(t, 1H, J=7.8 Hz), 8.55(d, 1H, J=4.5 Hz)

IR(neat): 2928, 2854, 1714, 1671, 1598, 1463, 1437, 1390, 1346, 1249, 1112, 981, 908 cm⁻¹

(b) preparation of the title compound of this example

Following the procedure described in example 27f, but replacing the compound prepared in example 27e with the compound prepared in example 33a, the title compound of this example was obtained as a white solid(77% yield).

¹H-NMR(300 MHz, CDCl₃): 0.88(t, 3H, J=6.6 Hz), 1.21–1.35(m, 26H), 1.52–1.58(m 2H), 1.78(t, 3H, J=6.9 Hz), 2.21–2.55(m, 2H), 3.29–3.59 (m, 6H), 3.92(s, 3H), 4.21–4.30(m, 2H), 5.25(q, 2H, J=7.2 Hz), 5.54(s, 2H), 6.94(d, 1H, J=8.4 Hz), 7.06(t, 1H, J=7.4 Hz), 7.44–7.51(m, 2H), 8.03–8.15(m, 2H), 8.46(t, 1H, J=7.5 Hz), 10.23(d, 1H, J=5.9 Hz)

IR(neat):2923, 2853, 1742, 1671, 1630, 1601, 1489, 1335, 1249, 1136, 1018, 977, 889 cm⁻¹

Mass(FAB, m/z): 655(M⁺–Cl)

Example 34 trans-N-[4-[[[4-[[(Octadecylcarbamoyl)oxy]methyl]-2-thietanyl]methoxy]carbonyl]butyl]quinolinium bromide

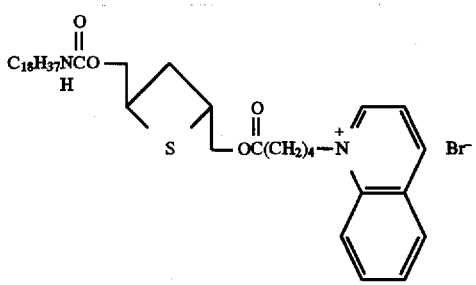

(a) trans-[4-[[(Octadecylcarbamoyl)oxy]methyl]-2-thietanyl]methyl 5-bromopentanoate

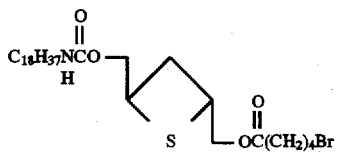

Following the procedure described in example 21b, but replacing the compound prepared in example 21a with trans-4-[[N-Octadecylcarbamoyl)oxy]methyl]thietane-2-methanol, the desired compound was obtained as a white solid(97% yield).

mp: 80.7°–81.8° C.

$^1$H-NMR(300 MHz CDCl$_3$): δ0.88(t, 3H, J=6.9 Hz), 1.20–1.40(m, 30H), 1.45–1.55(m, 2H), 1.75–1.96(m, 4H), 2.37(t, 2H, J=7.3 Hz), 2.68–2.74(m, 2H), 3.15(q, 2H, J=6.6 Hz), 3.41(t, 2H, J=6.4H), 3.66–3.76 (m, 2H), 4.17–4.25(m, 2H), 4.33–4.42(m, 2H), 4.65(br s, 1H)

IR(KBr): 3334, 2920, 2849, 1737, 1689, 1535, 1464, 1252, 1160, 1031, 777, 723, 641 cm$^{-1}$ (b) preparation of the title compound of this example Following the procedure described in example 23, but replacing the compound prepared in example 21b with the compound prepared in example 34a, the title compound of this example was obtained as a light purple solid(75% yield).

mp: 55.3°–57.8° C.

$^1$H-NMR(300 MHz, CDCl$_3$): δ0.88(t, 3H, J=6.8 Hz), 1.19–1.51(m, 32H), 1.89–1.97(m, 2H), 2.17–1.25(m, 2H), 2.48(t, 2H, J=6.9 Hz), 2.66–2.72 (m, 2H), 3.11–3.18(m, 2H), 3.63–3.71(m, 2H), 4.14–4.36 (m, 4H), 4.85(br s, 1H), 5.51(t, 2H, J=7.7 Hz), 7.97(t, 1H, J=7.6 Hz), 8.15–8.36(m, 2H), 8.30(d, 1H J=7.4 Hz), 8.46(d, 1H, J=9.0 Hz), 9.01(d, 1H, J=8.4 Hz), 10.72(d, 1H, J=5.7 Hz)

IR(KBr): 3370, 2920, 2850, 1729, 1690, 1530, 1466, 1375, 1250, 1161, 761 cm$^{-1}$

Mass(FAB, m/z): 641 (M$^+$–Br)

Example 35 trans-N-[4-[[4-[[(Octadecylcarbamoyl)oxy]methyl]-2-thietanyl]methoxy]butyl]quinolinium bromide

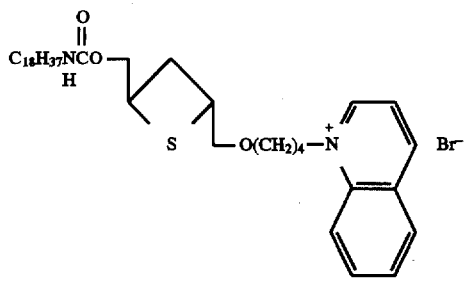

(a) trans-N-[4-[4-[[(Octadecylcarbamoyl)oxy]methyl]-2-thietanyl]methoxy]butyl bromide

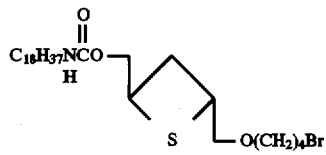

To a cold (5° C.) stirred solution of trans-4-[[N-Octadecylcarbamoyl)oxy]methyl]thietane-2-methanol (100 mg) in dimethyl sulfoxide (2 ml) was added potassium hydroxide(20 mg) and then 1,4-dibromobutane(0.036 ml) at room temperature. After stirring for 12 h, the mixture was diluted with ethyl acetate, washed successively with 1N-HCl solution and water. The organic layer was dried, concentrated under reduced pressure, and the resulting residue purified by flash chromatography on silica gel (ethyl acetate:hexane=1:5) to afford 60 mg of the desired product as a colorless oil(46% yield).

$^1$H-NMR(300 MHz, CDCl$_3$): δ0.87(t, 3H, J=6.2 Hz), 1.25(s, 30H), 1.55(m, 4H), 1.77(m, 4H), 2.67(m, 2H), 3.10 (q, 2H, J=6.4 Hz), 3.43(q, 4H, J=6.4 Hz), 3.64(br s, 4H), 4.28(t, 2H, J=5.6 Hz), 4.65(br s, 1H).

(b) Preparation of the title compound of this example

Following the procedure described in example 23, but replacing the compound prepared in example 21b with the compound prepared in example 35a, the desired compound was obtained as a yellow solid(76% yield).

mp: 46.3°–48.1° C.

H-NMR(300 MHz, CDCl$_3$): δ0.87(t, 3H, J=6.2 Hz), 1.25 (br s, 30H), 1.48(br s, 2H), 1.88 (m, 2H), 2.27(m, 2H), 2.67(t, 2H, J=6.8 Hz), 3.13(q, 2H, J=6.3 Hz), 3.61–3.75(m, 6H), 4.20–4.36(m, 4H), 4.85(br s, 1H), 5.48(t, 2H, J=8.0 Hz), 7.96(t, 1H, J=7.6 Hz), 8.15–8.29 (m, 3H), 8.41(d, 1H, J=9.0 Hz), 8.95(d, 1H, J=8.4 Hz), 10.71(d, 1H, J=5.4 Hz).

IR(KBr): 3401, 2919, 2850, 1707, 1530, 1463, 1377, 1266, 1121, 775 cm$^{-1}$

Mass(FAB, m/z): 613(M$^+$–Br)

Example 36

2-[[N-Acetyl-N-[[[3-[[(octadecylcarbamoyl)oxy]methyl]-3-thietanyl]methoxy]carbonyl]amino]methyl]-1-ethyl-pyridinium iodide (a) Isopropylidene ketal of 3,3-bis-(hydroxymethyl)thietane To a stirred solution of 5,5-bis(bromomethyl)-2,2-dimethyl-1,3-dioxane(5.00 g) in dimethyl sulfoxide (30 ml) was added sodium sulfide($Na_2S$ $9H_2O$, 0.32 g) at room temperature. After stirring for 3 h, the reaction mixture was diluted with ethyl acetate, washed with brine and water. The organic layer was dried, concentrated under reduced pressure and the resulting residue purified by flash chromatography on silica gel (ethyl acetate:hexane=1:5) to afford 2.50 g of the desired product as a viscous solid (87% yield).

$^1$H-NMR(80 MHz, $CDCl_3$): δ1.37(s, 6H), 2.95(s, 4H), 3.86(s, 4H)

IR(KBr): 2997, 2937, 2860, 1445, 1379, 1185, 1114, 1050, 929, 824, 730, 660, 516 cm$^{-1}$ (b) 3,3-Bis-(hydroxymethyl)thietane The above-described acetonide compound(0.50 g) dissolved in ethyl acetate(20 ml) containing water(0.1 ml) and trace 1N-HCl was stirred at room temperature for 1 h. The reaction mixture was diluted with ethyl acetate, washed with 10% sodium bicarbonate solution and brine.

The organic layer was dried, concentrated under reduced pressure, and the resulting residue purified by flash chromatography on silica gel (ethyl acetate:hexane=1:5) to afford 0.30 g of the desired product as a white solid (98% yield).

mp: 69.1°–69.8° C.

$^1$H-NMR(80 MHz, $CDCl_3$+trace DMSO-d6): δ2.89(s, 4H), 3.63(d, 4H, J=5.6 Hz), 4.32(t, 2H, J=5.6 Hz)

IR(KBr): 3247, 2931, 1452, 1356, 1100, 1123, 1023, 690, 586 cm$^{-1}$ (c) 3-[[(N-Octadecylcarbamoyl)oxy]methyl]thietane-3-methanol Following the procedure described in example 14a, but replacing 1,1-bis-hydroxymethyl)cyclobutane with the compound prepared in example 36b, the desired compound was obtained as a white solid(84% yield).

mp: 55.9°–57.3° C.

$^1$H-NMR(80 MHz, $CDCl_3$): δ0.87(t, 3H, J=5.6 Hz), 1.25 (s, 32H), 2.91(s, 4H), 3.12(q, 2H, J=7.2 Hz), 3.61(d, 2H, J=5.4 Hz), 4.30(s, 2H), 4.78(m, 1H)

IR(KBr): 3400, 2922, 2851, 1710, 1538, 1464, 1255, 1044, 721 cm$^{-1}$ (d) 2-[[N-[[[3-[[(Octadecylcarbamoyl)oxy]methyl]-3-thietanyl]methoxy]carbonyl]amino]methyl]pyridine Following the procedure described in example 1d, but replacing the compound prepared in example 1c with the compound prepared in example 36c, the desired compound was obtained as a white solid(89% yield).

mp: 54.1°–56.5° C.

$^1$H-NMR(80 MHz, $CDCl_3$): δ0.87(t, 3H, J=5.6 Hz), 1.25 (s, 32H), 2.99(s, 4H), 3.11(q, 2H, J=7.2 Hz), 4.20(s, 2H), 4.24(s, 2H), 4.45(d, 2H, J=5.6 Hz), 4.75(m, 1H), 5.89(m, 1H), 7.10–7.34(m, 2H), 7.56–7.67(m, 1H), 8.52(d, 1H, J=3.2 Hz)

IR(KBr): 3389, 3290, 2918, 2850, 1724, 1687, 1545, 1510, 1263, 1205, 1145, 1029, 761 cm$^{-1}$ (e) 2-[[N-Acetyl-N-[[[3-[[(octadecylcarbamoyl)oxy]methyl]-3-thietanyl]methoxy]carbonyl]amino]-methyl]pyridine Following the procedure described in example 1e, but replacing the compound prepared in example 1d with the compound prepared in example 36d, the desired compound was obtained as a white solid(88% yield).

mp: 57.3°–58.5° C.

$^1$H-NMR(80 MHz, $CDCl_3$) δ0.86(t, 3H, J=4.8 Hz), 1.24 (s, 32H), 2.63(s, 3H), 2.69(s, 2H), 2.74(s, 2H), 3.16(q, 2H, J=5.6 Hz), 4.00(s, 2H), 4.25(s, 2H), 5.08(s, 2H), 5.20(m, 1H), 7.07–7.16(m, 2H), 7.52–7.67(m, 1H), 8.46(d, 1H, J=3.2 Hz)

Mass(FAB, m/z): 606($M^+$+1)

(f) Preparation of the title compound of this example

Following the procedure described in example 1f, but replacing the compound prepared in example 1e with the compound prepared in example 36e, the desired compound was obtained as a yellow solid(12% yield).

$^1$HNMR(300 MHz, $CDCl_3$): δ0.87(t, 3H, J=6.9 Hz), 1.25 (s, 30H), 1.48(m, 2H), 1.73(t, 3H, J=5.1 Hz), 2.64(s, 3H), 2.66(q, 4H, J=5.1 Hz), 3.13(q, 2H, J=5.6 Hz), 4.06(s, 2H), 4.29(d, 2H, J=4.8 Hz), 5.04(q, 2H, J=7.2 Hz), 5.08(br s, 1H), 5.47(s, 2H), 7.88–8.03(m, 2H), 8.44(m, 1H), 9.51(d, 1H, J=6.0 Hz)

Mass(FAB, m/z): 762($M^+$+1), 634($M^+$–I)

Example 37

2-[[N-Acetyl-N-[[[3-[[(octadecylcarbamoyl)oxy]methyl]thietane-1-oxide-3-yl]methoxy]carbonyl]amino]methyl]-1-ethyl-pyridinium iodide (a) 2-[[N-Acetyl-N-[[[3-[[(octadecylcarbamoyl)oxy]methyl]thietane-1-oxide-3-yl]methoxy]carbonyl]amino]methyl]pyridine To a stirred solution of the compound prepared in example 36d (100 mg) in methylene chloride (10 ml) was added m-chloroperbenzoic acid(50–60%, 48 mg) at −78° C. After stirring at −78° C. for 1 h, the reaction mixture was diluted with methylene chloride, washed successively with 10% sodium bicarbonate solution and water. The organic layer was dried, concentrated under reduced pressure and the resulting residue purified by flash chromatography on silica gel (methanol:methylene chloride=1:15) to afford 102 ml of the desired product as a light yellow solid(99% yield).

mp: 37.4°–39.0° C.

$^1$H-NMR(300 MHz, CDCl$_3$): δ0.88(t, 3H, J=6.9 Hz), 1.26(s, 30H), 1.50(m, 2H), 2.62(s, 3H), 3.01–3.17(m, 4H), 3.15(q, 2H, J=6.0 Hz), 3.92(d, 2H, J=4.2 Hz), 4.10 and 4.17(s, 2H), 5.02(br s, 1H), 5.09(s, 2H), 7.16–7.19(m, 2H), 7.65(m, 1H), 8.49(br s, 1H)

Mass(FAB, m/z): 622(M$^+$+1)

(b) preparation of the title compound of this example

Following the procedure described in example 1f, but replacing the compound prepared in example 1e with the compound prepared in example 37a, the desired compound was obtained as a light yellow solid(76% yield).

mp: 67.8°–73.3° C.

$^1$H-NMR(300 MHz, CDCl$_3$): δ0.87(t, 3H, J=6.9 Hz), 1.25(br s, 30H), 1.49(t, 2H, J=6.9 Hz), 1.74(t, 3H, J=7.2 Hz), 2.67 and 2.69(s, 3H), 3.09–3.20(m, 4H), 3.66 and 3.88(d, 2H,J=13.7 Hz), 4.03(d, 2H, J=15 Hz ), 4.38(d, 2H,J=12.3 Hz), 4.98–5.05(m, 2H), 5.25 and 5.35(br s, 1H), 5.58(d, 2H, 12.3 Hz), 7.98–8.05(m,2H), 8.05–8.56(m, 1H), 9.18 and 9.26 (d, 1H,J=6.0 Hz)

IR(KBr): 3366, 2920, 2850, 1718, 1630, 1525, 1456, 1359, 1225, 1156, 1069, 771 cm$^{-1}$

Example 38

2-[[N-Acetyl-N-[[[3-[[(octadecylcarbamoyl)oxy]methyl]thietane 1,1-dioxide-3-yl]methoxy]carbonyl]amino]methyl]-1-ethyl-pyridinium iodide (a) [3-[[(Octadecylcarbamoyl)oxy]methyl]-3-thietanyl]methyl phenyl carbonate Following the procedure described in example 3f, but replacing the compound prepared in example with 3e the compound prepared in example 36c, the desired compound was obtained as a white solid(72% yield).

mp: 56.3°–58.7° C.

$^1$H-NMR(80 MHz, CDCl$_3$): δ0.87(t, 3H, J=6.2 Hz), 1.25 (br s, 30H), 1.55(m, 2H), 3.05(s, 4H), 3.12(q, 2H, J=6.3 Hz), 4.28(s, 2H), 4.41(s, 2H), 4.75 (br s, 1H), 7.14–7.31(m, 5H)

(b) [3-[[(Octadecylcarbamoyl)oxy]methyl]thietane 1,1-dioxide-3-yl]methyl phenyl carbonate To a stirred solution of the compound prepared in example 38a(240 mg) in methylene chloride (10 ml) was added two equivalents of m-chloroperbenzoic acid(50–60%, 276 mg) at −78° C., and the mixture was allowed to warm to room temperature. After stirring overnight, the reaction mixture was diluted with methylene chloride, washed successively with 10% sodium bicarbonate solution and water. The organic layer was dried, concentrated under reduced pressure, and the resulting residue purified by flash chromatography on silica gel (ethyl acetate:hexane=1:5) to afford 190 mg of the desired product as a white solid (75% yield).

mp: 65.9°–67.4° C.

$^1$H-NMR(80 MHz, CDCl$_3$): δ0.87(t, 3H, J=6.2 Hz), 1.25 (br s, 32H), 3.13(q, 2H, J=6.2 Hz), 3.98(s, 4H), 4.35(s, 2H), 4.46(s, 2H), 4.88(br s, 1H), 7.10–7.52 (m, 5H)

IR(KBr): 3350, 2919, 2851, 1763, 1704, 1537, 1322, 1252, 1064, 773 cm$^{-1}$ (c) 2-[[N-[[[3-[[(Octadecylcarbamoyl)oxy]methyl]thietane 1,1-dioxide-3-yl]methoxy]carbonyl]amino]methyl]pyridine

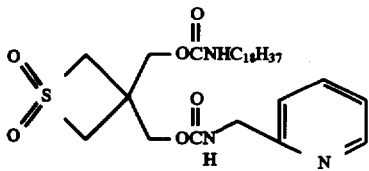

Following the procedure described in example 3 g, but replacing the compound prepared in example 3f with the compound prepared in example 38b, the desired compound was obtained as a white solid(87% yield).

mp: 79.1°–80.3° C.

$^1$H-NMR(80 MHz, CDCl$_3$): δ0.87(t, 3H, J=6.2 Hz), 1.25 (br s, 32H), 3.12(q, 2H, J=6.2 Hz), 4.02(s, 4H), 4.27(s, 2H), 4.31(s, 2H), 4.46(d, 2H, J=5.6 Hz), 4.85(br s, 1H), 6.01(br s, 1H), 7.20–7.28(m, 2H), 7.57–7.78 (m, 1H), 8.51(d, 1H, J=4.8 Hz)

IR(KBr): 3340, 2919, 2850, 1715, 1536, 1321, 1249, 1191, 1042, 770 cm$^{-1}$ (d) 2-[[N-Acetyl-N-[[[3-[[(octadecylcarbamoyl)oxy]methyl]thietane 1,1-dioxide-3-yl]methoxy]carbonyl]amino]methyl]pyridine

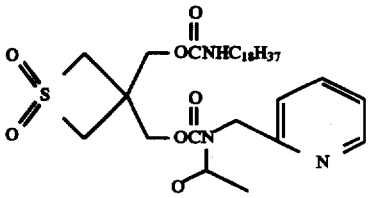

Following the procedure described in example 1e, but replacing the compound prepared in example 1d with the compound prepared in example 38c, the desired compound was obtained as a yellow solid(90% yield).

mp: 79.6°–81.6° C.

$^1$H-NMR(300 MHz, CDCl$_3$): δ0.88(t, 3H, J=6.9 Hz), 1.25(br s, 30H), 1.48(m, 2H), 2.63(s, 3H), 3.15(q, 2H, J=6.6 Hz), 3.73(q, 4H, J=13.8 Hz), 4.10(s, 2H), 4.32(s, 2H), 5.08(s, 2H), 5.27(br s, 1H), 7.15–7.19(m, 2H), 7.62–7.68(m, 1H), 8.46(d, 1H, J=4.5 Hz)

IR(KBr): 3352, 2920, 2851, 1720, 1536, 1328, 1210, 1103, 985, 771 cm$^{-1}$

Mass(FAB, m/z): 638(M$^+$1)

(e) preparation of the title compound of this example

Following the procedure described in example 1f, but replacing the compound prepared in example 1e with the compound prepared in example 38d, the desired compound was obtained as a light yellow solid(75% yield).

mp: 53.2°–56.4° C.

$^1$H-NMR(300 MHz, CDCl$_3$): δ0.88(t, 3H, J=6.9 Hz), 1.25 (br s, 30H), 1.48(br s, 2H), 1.75 (t, 3H, J=7.2 Hz), 2.69(s, 3H), 3.13(q, 2H, J=6.6 Hz), 4.05(d, 2H, J=14.4 Hz), 4.23(s, 2H), 4.26(d, 2H, J=15.3 Hz), 4.55(s, 2H), 4.91(q, 2H, J=7.2 Hz), 5.10(br s, 2H), 5.36(t, 1H, J=5.7 Hz), 5.57(s, 2H), 7.99(t, 1H, J=6.6 Hz), 8.10(d, 1H, J=8.4 Hz), 8.53(t, 1H, J=7.8 Hz), 9.14(d, 1H, J=6.0 Hz)

IR(KBr): 3355, 2919, 2850, 1724, 1630, 1526, 1459, 1330, 1224, 1175, 1085, 981, 772 cm$^{-1}$

Mass(FAB, m/z): 666(M$^+$-I)

Example 39

N-[5-[[[3-[[(Octadecylcarbamoyl)oxy]methyl]-3-thietanyl]methoxy]carbonyl]pentyl]pyridinium bromide

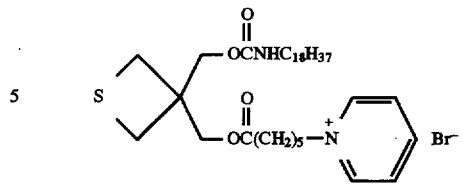

(a) [3-[[(N-Octadecylcarbamoyl)oxy]-3-thietanyl]methyl-6-bromohexanoate

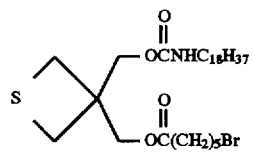

To a stirred solution of the compound prepared in example 36c(800 mg) in methylene chloride (10 ml) was added dry pyridine(0.18 ml) and then 6-bromohexanoyl chloride(523 mg) at 0° C., and the mixture was allowed to warm to room temperature.

After stirring for 3 h, the reaction mixture was diluted with methylene chloride, washed successively with 1N-HCl solution and water. The organic layer was dried, concentrated under reduced pressure and the resulting residue purified by flash chromatography on silica gel (ethyl acetate:hexane=1:3) to afford 980 mg of the desired product as a white solid (87% yield).

mp: 56.7°–57.8° C.

$^1$H-NMR(80 MHz, CDCl$_3$): δ0.88(t, 3H, J=6.4 Hz), 1.26 (br s, 30H), 1.50–1.95(m, 8H), 2.37(t, 2H, J=6.4 Hz), 2.99(s, 2H), 3.01(s, 2H), 3.13(q, 2H, J=5.6 Hz), 3.40(t, 2H, J=6.4 Hz), 4.20(s, 2H), 4.22(s, 2H), 4.75(m, 1H)

IR(KBr): 3282, 2919, 2850, 1731, 1690, 1551, 1264, 1153, 1023, 721 cm$^{-1}$ (b) Preparation of the title compound of this example The compound prepared in example 39a(100 mg) was dissolved in dry pyridine (1.0 ml) and heated at 80° C. overnight. After removal of excess pyridine under reduced pressure, the residue obtained was purified by flash chromatography on silica gel (methanol:methylene chloride= 1:20) to afford 100 mg of the title compound as a white solid (88% yield).

mp: 66.4°–67.8° C.

$^1$HNMR(300 MHz, CDCl$_3$): δ0.87(t, 3H, J=6.9 Hz), 1.25 (br s, 30H), 1.49(m, 4H), 1.70(m, 2H), 2.09(m, 2H), 2.37(t, 2H, J=7.2 Hz), 2.92(d, 2H, J=9.9 Hz), 3.03(d, 2H, J=9.9 Hz), 3.14(q, 2H, J=6.3 Hz), 4.16(s, 2H), 4.21(s, 2H), 4.96(br s, 1H), 5.03(t, 2H, J=7.2 Hz), 8.14(t, 2H, J=7.8 Hz), 8.51(t, 1H, J=7.8 Hz), 9.53(d, 2H, J=6.0 Hz)

IR(KBr): 3385, 2918, 2849, 1727, 1691, 1548, 1467, 1260, 1170, 1027, 776 cm$^{-1}$

Mass(FAB, m/z): 605(M$^+$-Br)

Example 40

3-[5-[[[3-[[(Octadecylcarbamoyl)oxy]methyl]-3-thietanyl]methoxy]carbonyl]pentyl]thiazolium bromide

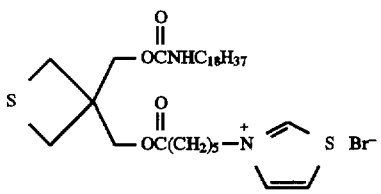

The compound prepared in example 39a (200 mg) was dissolved in thiazole (0. 5 ml) and heated at 100 ° C. for 15 hrs. After removal of excess thiazole under reduced pressure, the residue obtained was purified by flash chromatography on silica gel (methanol:methylene chloride= 1:10) to afford 152 mg of the title compound as a white solid (67% yield).

mp: 60.9°–61.4° C.

$^1$H-NMR(300 MHz, CDCl$_3$): δ0.87(t, 3H, J=6.6 Hz), 1.25(br s, 30H), 1.46(m, 4H), 1.70(m, 2H), 2.07(m, 2H), 2.37(t, 2H, J=7.2 Hz), 2.92(d, 2H, J=9.9 Hz), 3.04(d, 2H, J=9.9 Hz), 3.14(q, 2H, J=6.3 Hz), 4.16(s, 2H), 4.22(s, 2H), 4.89(t, 2H, J=7.2 Hz), 4.92(br s, 1H), 8.31(t, 1H, J=3.0 Hz), 8.56(d, 1H, J=3.3 Hz), 11.23(s, 1H)

IR(KBr): 3384, 2918, 2849, 1727, 1693, 1544, 1465, 1260, 1161, 1027, 721 cm$^{-1}$

Mass(FAB, m/z): 611(M$^+$–Br)

Example 41

N-[5-[[[3-[[(Octadecylcarbamoyl)oxy]methyl]-3-thietanyl]methoxy]carbonyl]pentyl]quinoline bromide

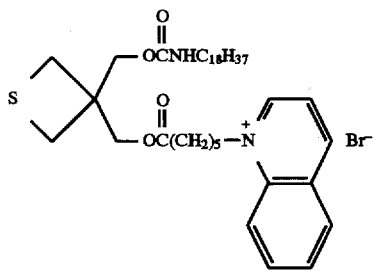

The compound prepared in example 39a(130 mg) was dissolved in quinoline (0.5 ml) and heated at 70° C. for 24 hrs. After removal of excess quinoline under reduced pressure, the residue obtained was purified by flash chromatography on silica gel (methanol:methylene chloride= 1:10) to afford 120 mg of the title compound as a light yellow solid (76% yield).

mp: 50.7°–52.6° C.

$^1$H-NMR(300 MHz, CDCl$_3$): δ0.87(t, 3H, J=6.9 Hz), 1.25(br s, 30H), 1.50(br s, 2H), 1.61–1.76(m, 4H), 2.16(t, 2H, J=6.6 Hz), 2.37(t, 2H, J=6.0 Hz, 2.91(d, 2H, J=9.6 Hz), 3.01(d, 2H, J=9.3 Hz), 3.11(q, 2H, J=6.6 Hz), 4.17(s, 2H), 4.20(s, 2H), 4.89(br s, 1H), 5.48(t, 2H, J=6.9 Hz), 7.96(t, 1H, J=7.5 Hz), 8.17(m, 2H), 8.24(d, 1H, J=8.9 Hz), 8.43(d, 1H, J=8.9 Hz), 9.02(d, 1H, J=8.1 Hz), 10.68(d, 1H, J=3.9 Hz)

IR(KBr): 3388, 2918, 2849, 1715, 1530, 1463, 1376, 1250, 775, 721 cm$^{-1}$

Mass(FAB, m/z): 655(M$^+$–Br)

Example 42

N-[4-[[[3-[(Hexadecyoxy)methyl]-3-thietanyl]methoxy]carbonyl]butyl]quinolinium bromide

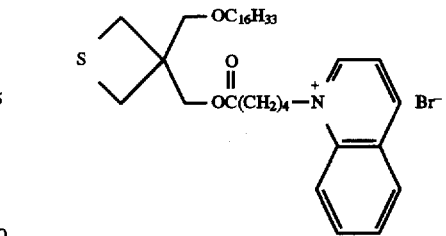

(a) 3-[(Hexadecyloxy)methyl]thietane-3-methanol

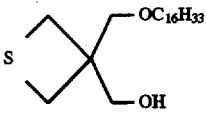

To a stirred solution of 3,3-bis-(hydroxymethyl) thietane (100mg) in dimethyl sulfoxide (3 ml) was added potassium hydroxide(50 mg) and then 1-bromohexadecane (0.23 ml) at room temperature. After stirring for .12 h, the reaction mixture was diluted with ethyl acetate, washed successively with 1N-HCl solution and water. The organic layer was dried, concentrated under reduced pressure, and the resulting residue purified by flash chromatography on silica gel (ethyl acetate:hexane=1:5) to afford 130 mg of the desired product as a light yellow solid(50% yield).

mp: 31.1°–33.2° C.

$^1$H-NMR(80 MHz, CDCl$_3$): δ0.87(t, 3H, J=5.6 Hz), 1.25 (br s, 28H), 2.27(br s, 1H), 2.93(s, 2H), 2.95(s, 2H), 3.46(t, 2H, J=6.0 Hz), 3.66(s, 2H), 3.80(s, 2H)

IR(KBr): 3387, 2924, 2852, 1462, 1109, 1042 cm$^{-1}$ (b) 3-[[(Hexadecyloxy)methyl]-3-oxetanyl]methyl 5-bromopentanoate

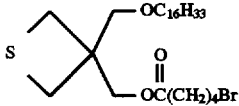

Following the procedure described in example 21b, but replacing the compound prepared in example 21a with the compound prepared in example 42a, the desired compound was obtained as a colorless oil(89% yield).

$^1$H-NMR(300 MHz, CDCl$_3$) δ0.88(t, 3H, J=6.9 Hz), 1.26(br s, 26H), 1.54(br s, 2H), 1.80–1.92(m, 4H), 2.39(t, 2H, J=6.9 Hz), 2.97(d, 4H, J=2.4 Hz), 3.39–3.46(m, 4H), 3.52(s, 2H), 4.20(s, 2H)

(c) preparation of the title compound of this example

Following the procedure described in example 23, but replacing the compound prepared in example 21b with the compound prepared in example 42b, the title compound of this example was obtained as a light yellow solid(73% yield).

mp: 33.7°–35.3° C.

$^1$H-NMR(300 MHz, CDCl$_3$): δ0.87(t, 3H, J=3.4 Hz), 1.26(s, 26H), 1.53(br s, 2H), 1.95(m, 2H), 2.24(m, 2H), 2.50(m, 2H), 2.90(m, 4H), 3.42(m, 2H), 3.48(d, 2H, J=4.0 Hz), 4.14(d, 2H, J=5.4 Hz), 5.54(m, 2H), 7.95(m, 1H), 8.22(m, 2H), 8.33(t, 1H, J=6.8 Hz), 8.50 (t, 1H, J=7.5 Hz), 9.07(dd, 1H, J=8.4 Hz, 8.2 Hz), 10.73(d, 1H, J=5.7 Hz)

IR(KBr): 3414, 2919, 2850, 1731, 1624, 1593, 1528, 1464, 1376, 1250, 1170, 1112 776 cm$^{-1}$

Mass(FAB, m/z): 570(M$^+$–Br)

Example 43

2-[[N-Acetyl-N-[[[4-[[(octadecylcarbamoyl)oxy]methyl]-1-acetyl azetidine-2-yl]methoxy]carbonyl]amino]methyl]-1-ethyl-pyridinium chloride

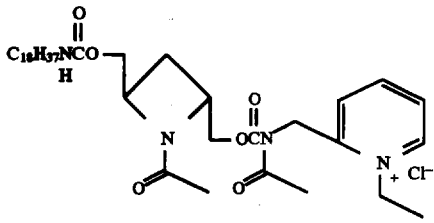

(a) trans-N-benzyl-2,4-Bis-(carbomethoxy)azetidine and its cis isomer

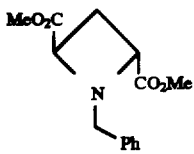

To a stirred solution of dimethyl 2,4-dibromo-glutarate (41.0 g) in acetonitrile(100 ml) was added 3 equivalent of benzylamine(14.9 ml) at room temperature. The reaction mixture was stirred for 1 h at room temperature and at 80° C. for 12 h. After removal of the solvent, the mixture was partitioned between ethyl acetate and water. The organic layer was dried, concentrated under reduced pressure, and the resulting residue purified by flash chromatography on silica gel (ethyl acetate:hexane=1:4) to afford 3.2 g(30%) of the trans isomer and 5.12 g(45%) of the cis isomer.

trans isomer: $^1$H-NMR(80 MHz, CDCl$_3$): δ2.50(t, 2H, J=6.8 hz), 3.65(s, 6H), 3.87(s, 2H), 4.21(t, 2H, J=6.7 Hz), 7.26(s, 5H)

cis isomer: $^1$H-NMR(80 MHz, CDCl$_3$): δ2.25–2.65(m, 2H), 3.34–3.75(m, 2H), 3.63(s, 6H), 3.88(s, 2H), 7.29(s, 5H)

(b) trans-2,4-Bis-(carbomethoxy)azetidine

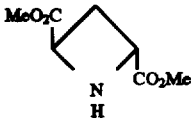

A mixture of trans-N-benzyl-2,4-Bis-(carbomethoxy)azetidine(250 mg) and palladium hydroxide on carbon(130 mg) in methanol(20 ml) was stirred in a Parr hydrogenator at 50 psi for 5 hrs. The reaction mixture was filtered, and the filtrate was concentrated under reduced pressure. The resulting residue was purified by flash chromatography on silica gel (ethyl acetate:hexane=2:1) to afford 110 mg of the desired compound(67% yield)

$^1$H-NMR(300 MHz, CDCl$_3$): δ2.72 (t, 2H, J=7.6 Hz), 2.79(s, 1H), 3.78(s, 6H), 4.32(t, 2H, J=7.5 Hz)

(c) trans-N-Acetyl-2,4-bis-(carbomethoxy)azetidine

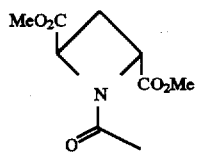

To a stirred solution of the compound obtained in example 43b (1.95 g) in methylene chloride (3 ml) at 0° C. was added dry triethylamine (3.3 ml) and then acetyl chloride(0.96 ml). The reaction mixture was stirred for 5 h at room temperature. After removal of the volatiles, the residue was partitioned between ethyl acetate and water. The organic layer was dried, concentrated under reduced pressure and the resulting residue purified by flash chromatography on silica gel (methanol:methylene chloride=1:20) to afford 2.25 g of the desired compound (67% yield).

$^1$H-NMR(80 MHz, CDCl$_3$): δ1.98(s, 3H), 2.75(t, 2H, J=7.5 Hz), 3.80(s, 6H), 4.75(t, 2H, J=7.6 Hz)

IR(KBr): 2968, 1752, 1655, 1424, 1358, 1202, 1031, 981, 903, 760, 704 cm$^{-1}$ (d) trans-N-Acetyl-2,4-bis-(hydroxymethyl)azetidine

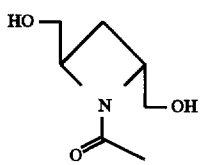

To a stirred solution of the compound obtained in example 43c (2.20 g) in dry ethyl ether(50 ml) was added lithium borohydride(0.65 g) at 0° C. The reaction mixture was then allowed to warm to room temperature and stirred overnight. The reaction was quenched by adding a trace amount of cold water. After drying and concentration under reduced pressure, the resulting residue was purified by flash chromatography on silica gel (ethyl acetate:hexane=2:1) to afford 0.83 g of the desired compound as a light yellow solid(57% yield).

$^1$H-NMR(300 MHz, CDCl$_3$): δ1.91–2.04(m, 4H), 2.12–2.25(m, 1H), 3.35(br s, 1H), 3.64–3.99 (m, 4H), 4.31–4.60(m, 2H), 5.15(br s, 1H)

IR(KBr): 3303, 2918, 2850, 1615, 1458, 1363, 1087, 1060, 949, 623 cm$^{-1}$ (e) trans-N-Acetyl-2,4-bis-[[(phenoxycarbony)oxy]methyl] azetidine

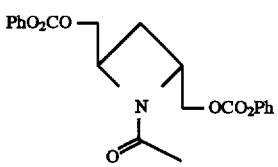

Following the procedure described in example 8a, but replacing the compound prepared in example 6b with the compound prepared in example 43d, the desired compound was obtained as a white solid(79% yield).

$^1$H-NMR(80 MHz, CDCl$_3$): δ1.96(s, 3H), 2.20–2.55(m, 2H), 4.21–4.96(m, 6H), 6.85–7.55(m, 10H)

(f) 2-[[N-[[[4-[[(Octadecylcarbamoyl)oxy]methyl]-1-acetyl azetidine-2-yl]methoxy]carbonyl]amino]methyl]pyridine

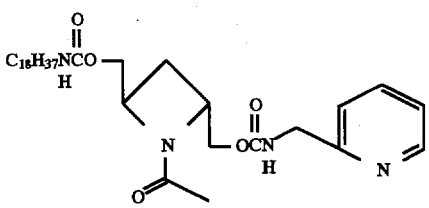

Following the procedure described in example 8b, but replacing the compound prepared in example 8a with the compound prepared in example 43e, the desired compound was obtained as a white solid(41% yield).

¹H-NMR(300 MHz, CDCl₃): δ0.88(t, 3H, J=6.9Hz), 1.20–1.55(m, 32H), 1.92(s, 3H), 2.10–2.35(m, 2H), 3.10–3.25(m, 2H), 4.21–4.58(m, 8H), 4.80–4.95(m, 1H), 5.88–6.12(m, 1 h), 7.17–7.29(m, 2H), 7.67(t, 1H, J=7.7 Hz), 8.54(d, 1H, J=4.6 Hz)

(g) 2-[[N-Acetyl-N-[[[4-[[(octadecylcarbamoyl)oxy]methyl]-1-acetyl azetidine-2-yl]methoxy]carbonyl]amino]methyl]pyridine

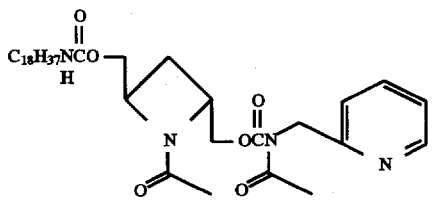

Following the procedure described in example 1e, but replacing the compound prepared in example 1d with the compound prepared in example 43f, the desired compound was obtained as a white solid(59% yield).

mp: 66.6°–67.8° C.

¹H-NMR(300 MHz, CDCl₃): δ0.88(t, 3H, J=7.1 hz), 1.20–1.55(m, 32H), 1.75(s, 3H), 1.95–2.05(m, 2H), 2.65(s, 3H), 3.15–3.25(m, 2H), 4.05–4.50(m, 6H), 4.70–4.80(m, 2H), 5.00–5.20(m, 3H), 7.10–7.25(m, 2H), 7.15–7.20(m, 1H), 8.50(d, 1H, J=5.1 Hz)

IR(KBr): 3372, 3237, 2920, 2850, 1710, 1623, 1535, 1448, 126, 1146, 755, 723 cm⁻¹

(h)Preparation of the title compound of this example

Following the procedure described in example 27f, but replacing the compound prepared in example 27e with the compound prepared in example 43 g, the desired compound was obtained as a light yellow solid(75% yield).

mp: 88.9°–97.0° C.

¹H-NMR(300 MHz, CDCl₃): δ0.86(t, 3H, J=6.6 Hz), 1.20–1.55(M, 32H), 1.67(t, 3H, J=7.2 Hz), 1.84(s, 3H), 2.05–2.30(m, 2H), 2.63(s, 3H), 3.05–3.20(m, 2H), 4.10–4.75(m, 6H), 5.15(q, 2H, J=7.2 Hz), 5.51(d, 2H, J=2.4 Hz), 5.80–5.90(m, 1H), 7.80–8.10(m, 2H), 8.42(app t, 1H, J=7.8 Hz), 9.75(d, 1H, J=6.1 Hz)

IR(KBr): 3404, 2920, 2851, 1741, 1695, 1633, 1532, 1438, 1227, 1160, 989, 774 cm⁻¹

Mass(FAB, m/z): 659(M⁺–Cl)

Example 44

2-[[N-Acetyl-N-[[[4-[[(octadecylcarbamoyl)oxy]methyl]-1-benzoyl azetidine-2-yl]methoxy]carbonyl]amino]methyl]-1-ethyl-pyridinium chloride

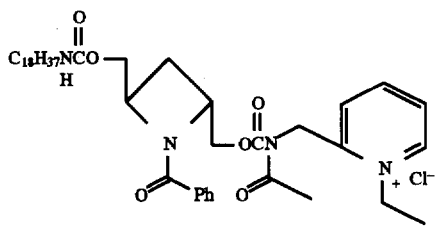

(a) trans-N-Benzoyl-2,4-bis-(carbomethoxy)azetidine

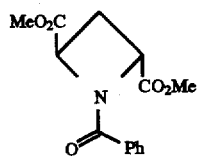

Following the procedure described in example 43c, but replacing acetyl chloride with benzoyl chloride, the desired compound was obtained as a white solid(70% yield).

mp: 81.6°–83.6° C.

¹H-NMR(80 MHz, CDCl₃) δ2.52(q, 2H, J=7.2 Hz), 3.37 (s, 3H), 3.67(s, 3H), 4.95(m, 2H), 7.18–7.56(m, 5H)

IR(KBr): 2957, 1747, 1631, 1578, 1420, 1285, 1207, 1033, 887, 717 cm⁻¹

(b) trans-N-Benzoyl-2,4-bis-(hydroxymethyl)azetidine

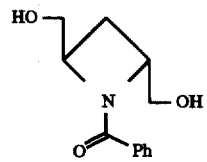

Following the procedure described in example 43d, but replacing the compound prepared in example 43c with the compound prepared in example 44a, the desired compound was obtained as a white solid(97% field).

¹H-NMR(80 MHz, CDCl₃): δ1.97–2.16(m, 2H), 3.19(br s, 2H), 3.72(q, 3H, J=4.8 Hz), 4.37–4.88(m, 3H), 7.25–7.48 (m, 5H)

(c)trans- N-Benzoyl-2,4-bis-[[(phenoxycarbony)oxy]methyl]azetidine

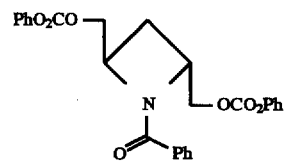

Following the procedure described in example 8a, but replacing the compound prepared in example 6b with the compound prepared in example 44b, the desired compound was obtained as a white solid(95% yield).

¹H-NMR(80 MHz, CDCl₃): δ2.12–2.53(m, 2H), 3.81–3.95(m, 3H), 4.55–4.87(m, 3H), 7.19–7.61(m, 15H)

(d)2-[[N-[[[4-[[(octadecylcarbamoyl)oxy]methyl]-1- benzoyl azetidine-2-yl]methoxy]carbonyl]amino]methyl] pyridine

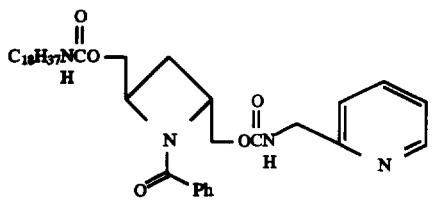

Following the procedure described in example 8b, but replacing the compound prepared in example 8a with the compound prepared in example 44c:, the desired compound was obtained as a light yellow solid(40% yield).

mp: 36.2°–38.5° C.

$^1$H-NMR(300 MHz, CDCl$_3$): δ0.88(t, 3H, J=6.6 Hz), 1.15–1.56(m, 32H), 2.12–2.45(m, 2H), 3.05–3.19(m, 2H), 3.62–3.75(m, 1H), 3.90–3.98(m, 1H), 4.38–5.10(m, 7H), 6.00(br s, 1H), 7.16–7.67(m, 8H), 8.54(d, 1H, J=4.5 Hz)

IR(KBr): 3315, 2919, 2850, 1714, 1624, 1573, 1530, 1467, 1254, 1146, 1038, 765 cm$^{-1}$ (e) 2-[[N- Acetyl-N-[[[4-[[(octadecylcarbamoyl)oxy]methyl]-1- benzoyl azetidine-2-yl]methoxy]carbonyl]amino]methyl]pyridine

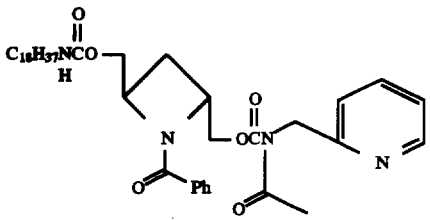

Following the procedure described in example 8c, but replacing the compound prepared in example 8b with the compound prepared in example 44d, the desired compound was obtained as a light yellow oil (72% yield).

$^1$H-NMR(300 MHz, CDCl$_3$): δ0.88(t, 3H, J=6.6 Hz), 1.20–1.56(m, 32H), 2.02–2.10(m, 2H), 2.66(s, 3H), 3.04–3.06(m, 2H); 3.55–3.95(m, 2H), 4.32–4.52(m, 2H), 4.66–4.68(m, 2H), 5.12–5.36(m, 2H), 7.13–7.62(m, 8H), 8.51(d, 1H, J=3.9 Hz)

IR(neat): 3335, 2924, 2853, 1738, 1710, 1633, 1593, 1530, 1389, 1344, 1212, 1153, 840 cm$^{-1}$ (f) Preparation of the title compound of this example Following the procedure described in example 27f, but replacing the compound prepared in example 27e with the compound prepared in example 44e, the desired compound was obtained as a light yellow solid (64% yield).

mp: 103.2°–105.7° C.

$^1$H-NMR(300 MHz, CDCl$_3$): δ0.88(t, 3H, J=6.6 Hz), 1.20–1.46(m, 32H), 1.64(t, 3H, J=7.2 Hz), 2.16–2.29(m, 2H), 2.66(s, 3H), 3.06–3.06(m, 2H), 3.58–3.62(m, 1H), 3.90–3.93(m, 1H), 4.39–4.42(m, 1H), 4.59–4.92(m, 3H), 5.17–5.19(m, 3H), 5.41–5.55(m, 2H), 7.38–8.07(m, 8H), 9.80(d, 1H, J=5.7 Hz)

IR(KBr): 3426, 2922, 2851, 1737, 1714, 1695, 1682, 1529, 1410, 1225, 987, 717 cm$^{-1}$

Mass(FAB, m/z): 721(M$^+$–Cl)

Example 45

2-[[N-Acetyl-N-[[[4-[[(octadecylcarbamoyl)oxy]methyl]-1-benzyl azetidine-2-yl]methoxy]carbonyl]amino]methyl]-1-ethyl-pyridinium chloride

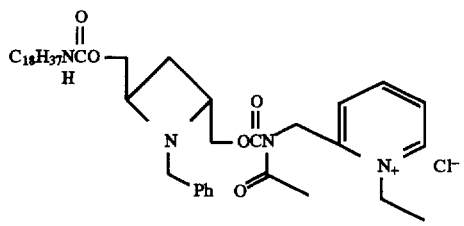

(a) trans-N-Benzyl-2,4-bis-(hydroxymethyl)azetidine

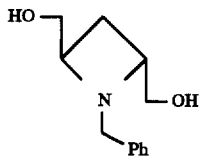

Following the procedure described in example 43d, but replacing the compound prepared in example 43c with the compound prepared in example 43a, the desired compound was obtained as a white solid (89% yield).

$^1$H-NMR(80 MHz, CDCl$_3$): δ2.03–2.89(m, 4H), 3.26–3.59(m, 2H), 3.96–4.46(m, 6H), 7.26–7.57(m, 5H)

(b) tans-N-Benzyl-2,4-bis-[[(phenoxycarbony)oxy]methyl]azetidine

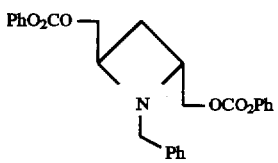

Following the procedure described in example 43e, but replacing the compound prepared in example 43d with the compound prepared in example 45a, the desired compound was obtained as a colorless oil (98% yield).

$^1$H-NMR(300 MHz, CDCl$_3$): δ2.12–2.47(m, 2H), 4.17–4.82(m, 8H), 7.09–7.40(m, 15H)

IR(neat): 3027, 2939, 1763, 1716, 1593, 1547, 1492, 1295, 1211, 1069, 1023, 779 cm$^{-1}$ (c) 2-[[N-[[[4-[[(octadecylcarbamoyl)oxy]methyl]-1-benzyl azetidine-2-yl]methoxy]carbonyl]amino]methyl]pyridine

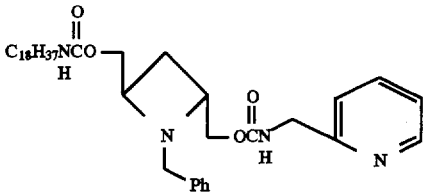

Following the procedure described in example 8b, but replacing the compound prepared in example 8a with the compound prepared in example 45a, the desired compound was obtained as a white solid(41% field).

$^1$H-NMR(300 MHz, CDCl$_3$): δ0.88(t, 3H, J=6.9 Hz), 1.17–1.51(m, 32H), 2.01–2.43(m, 2H), 3.05–3.10(m, 2H), 3.95–5.20(m, 11H), 6.09(br s, 1H), 7.10–7.61(m, 8H), 8.50 (d, 1H, J=4.5 Hz)

(d) 2-[[N-Acetyl-N-[[[4-[[(octadecylcarbamoyl)oxy]methyl]-1-benzyl azetidine-2-yl]methoxy]carbonyl]amino]methyl]pyridine

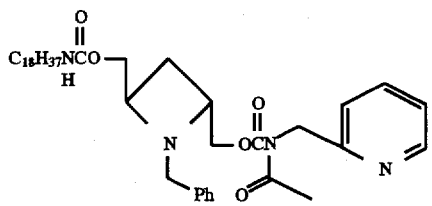

Following the procedure described in example 8c, but replacing the compound prepared in example 8b with the compound prepared in example 45b, the desired compound was obtained as a light yellow oil (82% yield).

$^1$H-NMR(300 MHz, CDCl$_3$): δ0.88(t, 3H, J=6.5 Hz), 1.15–1.57(m, 32H), 1.88–2.15(m, 2H), 2.56(s, 3H), 3.05–3.70(m, 4H), 4.22–5.05(m, 9H), 7.05–7.60(m, 8H), 8.48(d, 1H, J=4.2 Hz)

IR(neat): 3343, 2924, 2853, 1740, 1717, 1593, 1494, 1358, 1191, 1081, 980, 823, 773 cm$^{-1}$ (e) Preparation of the title compound of this example Following the procedure described in example 27f, but replacing the compound prepared in example 27e with the compound prepared in example 45c, the title compound of this example was obtained as a light yellow solid(90% yield).

$^1$H-NMR(300 MHz, CDCl$_3$): δ0.88(t, 3H, J=6.6 Hz), 1.15–1.58(m, 32H), 1.64(t, 3H, J=7.2 Hz), 2.15–2.30(m, 4H), 2.55(s, 3H), 3.03–3.70(m, 4H), 4.33–5.35(m, 9H), 7.03–7.97(m, 8H), 9.73(d, 1H, J=5.4 Hz)

IR(KBr): 3438, 2924, 2853, 1738, 1715, 1708, 1455, 1371, 1213, 981, 756 cm$^{-1}$

Example 46

2-[[N-(2-methoxy)benzoyl-N-[[[4-[[(octadecylcarbamoyl)oxy]methyl]-1-benzyl azetidine-2-yl]methoxy]carbonyl]amino]methyl]-1-ethyl-pyridinium chloride

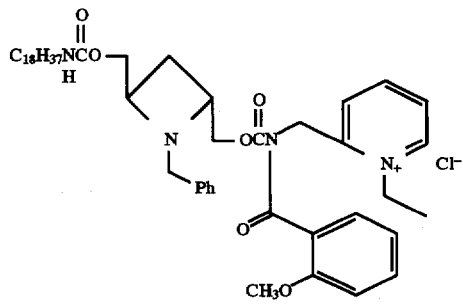

(a) 2-[[N-(2-methoxy)benzoyl-N-[[[4-[[(octadecylcarbamoyl)oxy]methyl]-1-benzyl azetidine-2yl]methoxy]carbonyl]amino]methyl]pyridine

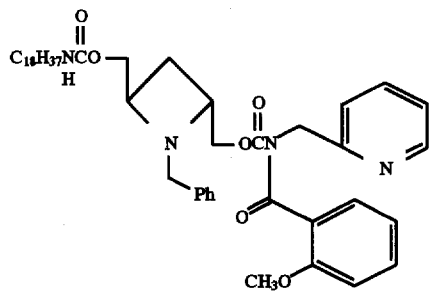

Following the procedure described in example 30a, but replacing the compound prepared in example 27d with the compound prepared in example 45b, the desired compound was obtained as a light yellow oil (74% yield).

$^1$H-NMR(300 MHz, CDCl$_3$): δ0.88(t, 3H, J=6.6 Hz), 1.15–1.53(m, 32H), 1.87–2.09(m, 2H), 3.09–3.16(m, 2H), 3.77(s, 3H), 3.81–4.47(m, 8H), 5.10–5.23(m, 3H), 6.86–7.63(m, 12H), 8.53(d, 1H, J=4.5 Hz)

IR(neat): 3366, 3018, 2920, 2853, 1713, 1681, 1596, 1526, 1491, 1352, 1173, 1024, 984 cm$^{-1}$ (b) preparation of the title compound of this example Following the procedure described in example 27f, but replacing the compound prepared in example 27e with the compound prepared in example 46a, the title compound of this example was obtained as a yellow solid(87% yield).

mp: 81.3°–82.7° C.

$^1$H-NMR(300 MHz, CDCl$_3$): δ0.88(t, 3H, J=6.6 Hz), 1.20–1.55(m, 32H), 1.72(t, 3H, J=7.2 Hz), 1.83–2.09(m, 2H), 3.10–3.17(m, 2H), 3.84(s, 3H), 3.87–4.55(m, 8H), 5.14–5.45(m, 5H), 6.89–8.30(m, 12H), 10.08(d, 1H, J=4.6 Hz)

IR(KBr): 3441,2924, 2853, 1735, 1715, 1705, 1521, 1459, 1219, 978, 756 cm$^{-1}$

Example 47

2-[[N-Acetyl-N-[[[3-[[(octadecylcarbamoyl)oxy]methyl]-1-acetyl azetidine-3-yl]methoxy]carbonyl]amino]methyl]-1-ethyl-pyridinium chloride

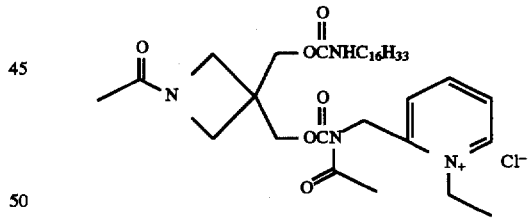

(a) Isopropylidene ketal of N-benzyl-3,3-bis-(hydroxymethyl)azetidine

To a stirred solution of 5,5-bis-(bromomethyl)-2,2-dimethyl-1,3-dioxane(10.0 g) in dimethyl sulfoxide (50 ml) was added benzyl amine(12 ml) at room temperature, and the mixture was allowed to warm to 80° C. After stirring for 12 h, the reaction mixture was diluted with ethyl acetate and washed with brine. The organic layer was dried, concentrated under reduced pressure, and the resulting residue purified by flash chromatography on silica gel (ethyl acetate:hexane=2:3) to afford 6.5 g of the desired product as a colorless oil (80% yield).

¹H-NMR(80 MHz, CDCl₃): δ1.37(s, 6H), 3.05(s, 4H), 3.61(s, 2H), 3.89(s, 4H), 7.26(s, 5H)

IR(KBr): 3277, 2886, 1653, 1535, 1454, 1386, 1154, 826, 698 cm⁻¹

Mass(EI, m/z): 247(M⁺)

(b) Isopropylidene ketal of 3,3-bis-(hydroxymethyl) azetidine

A mixture of the above-described compound(2.0 g) and 10% palladium on carbon(0.5 g) was stirred in methanol(30 ml) at room temperature for 36 h in a Parr hydrogenator(60 psi). After evaporation of the solvent, the residue was treated with 30 ml of a mixture of ethyl acetate and hexane(1:1). The resulting insoluble solid was filtered off and the filtrate concentrated to afford 1.0 g of the desired product as a colorless oil (80% yield).

¹H-NMR(80 MHz, CDCl₃): δ1.39(s, 6H), 2.82(br s, 1H), 3.93(s, 4H), 3.93(s, 4H)

IR(KBr): 3440, 2958, 1332, 1200, 1078, 937, 824, 519 cm⁻¹

(c) Isopropylidene ketal of N-Acetyl-3,3-bis-(hydroxymethyl)azetidine

To a stirred solution of the compound prepared in example (1.0 g) in methylene chloride(15 ml) at 0° C. was added triethyl amine(1.77 ml) and then acetic anhydride(0.72 ml), and the mixture was allowed to warm to room temperature. After stirring for 2 h, the reaction mixture was diluted with methylene chloride, washed successively with water, 10% sodium bicarbonate solution, and brine. The organic layer was dried, concentrated under reduced pressure, and the resulting residue purified by flash chromatography on silica gel (methanol:methylene chloride=1:50) to afford 0.98 g of the desired product as a light yellow solid (77% yield).

¹H-NMR(80 MHz, CDCl₃): δ1.38(s, 3H), 1.41(s, 3H), 1.85(s, 3H), 3.64(s, 2H), 3.89(s, 4H), 3.91(s, 2H)

IR(KBr): 2996, 2946, 2871, 1649, 1451, 1388, 1371, 1204, 1154, 1086, 824 cm⁻¹

(d)N-Acetyl-3,3-bis-[[(phenoxycarbony)oxy]methyl] azetidine

A mixture of the compound prepared in example 47c (0.36 g) and trifluoroacetic acid(0.5 ml) was stirred at room temperature in methylene chloride(10 ml) containing water (0.5 ml) for 8 h. After removal of the volatiles under reduced pressure, the residue obtained was dissolved in methylene chloride(10 ml) and treated with pyridine(0.48 ml) and phenyl chloroformate(0.55 ml). The mixture was stirred at room temperature for 2 h and washed with brine. The organic layer was dried, concentrated under reduced pressure, and the resulting residue purified by flash chromatography on silica gel (methanol:methylene chloride= 1:20) to afford 0.17 g of the desired product as a colorless oil (24% overal yield).

¹H-NMR(80 MHz, CDCl₃): δ1.87(s, 3H), 3.89(s, 2H), 4.02(s, 2H), 4.46(s, 4H), 7.19–7.30(m, 10H)

(e) 2-[[N-[[[3-[[(Octadecylcarbamoyl)oxy]methyl]-1-acetyl azetidine-3-yl]methoxy]carbonyl]amino]methyl]pyridine

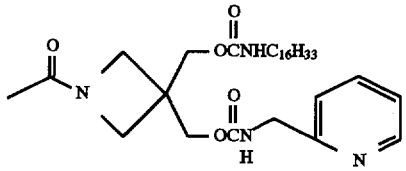

Following the procedure described in example 8b, but replacing the compound prepared in example 8a with the compound prepared in example 47d, the desired compound was obtained as a light yellow oil(49% yield).

¹H-NMR(80 MHz, CDCl₃): δ0.87(t, 3H, J=6.2 Hz), 1.25 (br s, 28H), 1.84(s, 3H), 3.11(q, 2H, J=6.0 Hz), 3.79(s, 2H), 3.92(s, 2H), 4.21(s, 2H), 4.25(s, 2H), 4.45(d, 2H, J=5.6 Hz), 4.80(br s, 1H), 6.01(br s, 1H), 7.20–7.30(m, 2H), 7.58(m, 1H), 8.52(d, 1H, J=3.2 Hz)

IR(neat): 3299, 2922, 2852, 1716, 1642, 1537, 1464, 1254, 1041, 744 cm⁻¹

(f) 2-[[N-Acetyl-N-[[[3-[[(octadecylcarbamoyl)oxy]methyl]-1-acetyl azetidine-3-yl]methoxy]carbonyl]amino]methyl] pyridine

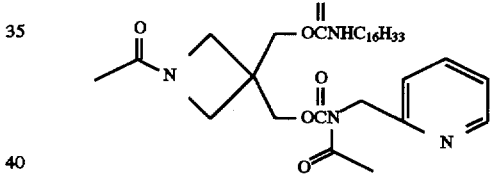

Following the procedure described in example 1e, but replacing the compound prepared in example 1d with the compound prepared in example 47e, the desired compound was obtained as a light yellow oil (74% yield).

¹H-NMR(80 MHz, CDCl₃): δ0.87(t, 3H, J=5.6 Hz), 1.25 (s, 28H), 1.76(s, 3H), 2.63(s, 3H), 3.10(q, 2H, J=6.0 Hz), 3.58(s, 2H), 3.70(s, 2H), 4.04(s, 2H), 4.27(s, 2H), 5.07(s, 2H), 5.08(br s, 1H), 7.08–7.23(m, 2H), 7.54–7.66(m, 1H), 8.45(d, 1H, J=4.0 Hz)

IR(neat): 3315, 2925, 2853, 1724, 1650, 1449, 1352, 1221, 979, 768 cm⁻¹

(g) Preparation of the title compound of this example

Following the procedure described in example 27f, but replacing the compound prepared in example 27e with the compound prepared in example 47f, the title compound of this example was obtained as a light yellow solid(50% yield).

mp: 48.3°–52.1° C.

¹H-NMR(300 MHz, CDCl₃): δ0.87(t, 3H, J=6.3 Hz), 1.25(br s, 26H), 1.48(br s, 2H), 1.71(t, 3H, J=3.8 Hz), 1.63(s, 3H), 2.64(s, 3H), 3.11(br s, 2H), 3.73(s, 2H), 3.99–4.21(m, 4H), 4.47(s, 2H), 5.12(br s, 2H), 5.35(br s, 1H), 5.59(s, 2H), 7.79(d, 1H, J=7.1 Hz), 7.97(br s, 1H), 8.39(t, 1H, J=7.7 Hz), 9.43(br s, 1H)

IR(KBr): 3410, 2924, 2853, 1706, 1635, 1526, 1460, 1363, 1226, 1160, 1087, 984, 772, 596 cm⁻¹

Mass(FAB, m/z): 631($M^+$–Cl)

We claim:

1. A compound of the formula I or pharmaceutically acceptable salts thereof:

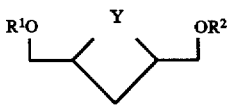

in which

Y represents a divalent group selected from the class consisting of S, SO, $SO_2$, $CH_2$, and $NR^a$ group wherein $R^a$ is hydrogen, lower alkyl, lower alkoxycarbonyl, phenyl, naphthyl, phenylalkyl, naphthylalkyl or alkylacyl;

$R^1$ represents either an alkyl, alkenyl or alkynyl group, of 10 to 24 carbon atoms or a $CONR^3R^4$ group, wherein $R^3$ is hydrogen or lower alkyl and $R^4$ is an alkyl, alkenyl or alkynyl group, of 10 to 24 carbon atoms;

$R^2$ represents a group having formula T—$(CH_2)_n$—V, wherein T refers to a simple covalent linkage, or a CO, $PO_3$, C(O)), or $CONR^b$ group wherein $R^b$ is hydrogen, lower alkyl or acyl;

n refers to an integer of from 1 to 10;

V represents

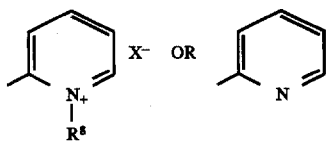

wherein $R^8$ represents lower alkyl group; and $X^-$ represents a pharmaceutically acceptable anion such as halide (chloride, bromide, or iodide), lower alkyl sulfonate, arylsulfonate, carboxylate, nitrate or phosphate.

2. A compound according to claim 1, wherein Y is a sulfur atom, a methylene or $NR^a$ group in which $R^a$ is alkylacyl.

3. A compound according to claim 2, wherein $R^a$ is $C_1$-$C_3$ alkanoyl or benzoyl.

4. A compound according to claim 1, wherein $R^1$ is an alkyl group of 14 to 20 carbon atoms.

5. A compound according to claim 1, wherein $R^1$ is a $CONR^3R^4$ group where one of $R^3$ and $R^4$ is hydrogen and the other group is an alkyl chain of 14 to 20 carbon atoms.

6. A compound according to claim 1, wherein $R^2$ represents a group of formula:

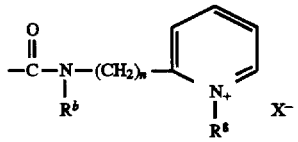

in which $R^b$ is a $C_1$-$C_3$ alkanoyl or benzoyl group unsubstituted or substituted by a o-, m- or p-methoxy group, n is an integer of 1 to 3, $R^8$ is a $C_1$-$C_3$ alkyl group, and $X^-$ represents a pharmaceutically acceptable anion.

7. A compound according to claim 6, wherein $R^b$ is an acetyl or o-methoxy benzoyl group, n is an integer of 1, $R^8$ is ethyl, and $X^-$ represents chloride, bromide or iodide.

8. A pharmaceutical composition for use as a PAF antagonist comprising a therapeutically effective amount of a compound according to claim 1 in combination with a pharmaceutically acceptable carrier or diluent.

* * * * *

UNITED STATES PATENT AND TRADEMARK OFFICE
CERTIFICATE OF CORRECTION

PATENT NO. : 5,700,817
DATED : December 23, 1997
INVENTOR(S) : Soon Hyung Woo et al.

It is certified that error appears in the above-identified patent and that said Letters Patent is hereby corrected as shown below:

Title Page, under [30] Foreign Application Priority Data, insert --Jun. 30, 1992 [KR] Rep. of Korea....92-11554--.

Title Page, under [56] References Cited, OTHER PUBLICATIONS, first reference, "platelet-activatingfactor" should read --platelet-activating factor--.

Title Page, under [56] References Cited, OTHER PUBLICATIONS, second reference, "antagonistswith" should read --antagonists with--.

Title Page, under [56] References Cited, OTHER PUBLICATIONS, second reference, "nitrogendistance:" should read --nitrogen distance--.

Title Page, under [56] References Cited, OTHER PUBLICATIONS, second reference, "characterizationand" should read --characterization and--.

Title Page, under [56] References Cited, OTHER PUBLICATIONS second reference, "activityrelationships" should read --activity relationships--.

Title Page, under [56] References Cited, OTHER PUBLICATIONS, third reference, "phospholipidstructure." should read --phospholipid structure.--.

Title Page, under [56] References Cited, OTHER PUBLICATIONS, third reference, "characterizationand" should read --characterization and--.

Title Page, under [56] References Cited, OTHER PUBLICATIONS, third reference, "determiningstructural" should read --determining structural--.

UNITED STATES PATENT AND TRADEMARK OFFICE
CERTIFICATE OF CORRECTION

PATENT NO. : 5,700,817
DATED : December 23, 1997
INVENTOR(S) : Soon Hyung Woo et al.

It is certified that error appears in the above-identified patent and that said Letters Patent is hereby corrected as shown below:

Title Page, under [56] References Cited, OTHER PUBLICATIONS, fourth reference, "activatingfactor" should read --activating factor--.

Column 1 Line 43 after "patents" delete period --.--.

Column 1 Line 43 before "Japanese" insert --Japanese Laid-Open Patent No. Sho 57-67589,--.

Column 1 Line 47 "arc satisfactory" should read --are satisfactory--.

Column 2 Line 11 after "refers" insert --to--.

Column 2 Line 12 after "$PO_3^-$" delete semicolon and insert comma --,--.

Column 2 Line 16 before "$NR^5R^6R^7$" insert superscript plus sign --$^+$--.

Column 2 Line 19 "ii)" should read --(ii)--.

Column 3 Line 8 "arylakyl" should read --arylalkyl--.

Column 3 Line 40 "alkoxy-1-halogen" should read --alkoxy, halogen--.

Column 4 Line 8 "heptadeyl" should read --heptadecyl--.

Column 4 Line 13 "heptadeyl" should read --heptadecyl--.

Column 4 Line 29 "includes" should read --include--.

UNITED STATES PATENT AND TRADEMARK OFFICE
CERTIFICATE OF CORRECTION

PATENT NO. : 5,700,817
DATED : December 23, 1997
INVENTOR(S) : Soon Hyung Woo et al.

Page 3 of 9

It is certified that error appears in the above-identified patent and that said Letters Patent is hereby corrected as shown below:

Column 4 Line 65 "In step 2, A compound" should read --In step 2, a compound--.

Column 5, Scheme 1, beside down arrow under VIII, "Quarternization" should read --Quaternization--.

Column 7 Lines 19-20 "+" at end of line 19 should appear at beginning of line 20.

Column 7 Line 27 "$(CH_2)_n)$]" should read --$(CH_2)_nX)$]--.

Column 7 Line 29 "quarternization" should read --quaternization--.

Column 7 Line 31 "$NR^5R^6N^7$" should read --$NR^5R^6R^7$--.

Column 8 Line 35 before "This" delete comma and insert period --.--.

Column 8 Line 51 "$NR^5R^6N^7$" should read --$NR^5R^6R^7$--.

Column 8 Line 52 "quarternary" should read --quaternary--.

Column 8 Line 65 "(IVI)" should read --(XVI)--.

Column 9 Line 63 "quarternization" should read --quaternization--.

Column 10 Line 1 "Scheme" should read --Schemes--.

Column 10 Line 37 "Compound" should read --compound--.

Column 10 Line 48 "n-tributylin" should read --tributyltin--.

UNITED STATES PATENT AND TRADEMARK OFFICE
CERTIFICATE OF CORRECTION

PATENT NO. : 5,700,817
DATED : December 23, 1997
INVENTOR(S) : Soon Hyung Woo et al.

It is certified that error appears in the above-indentified patent and that said Letters Patent is hereby corrected as shown below:

Column 10 Line 57 after "compound" insert --(IIIa).--.

Column 11 Line 32 "diastereometric" should read --diastereomeric--.

Column 12 Line 51 "(XXIII)" should read --(XXIII')--.

Column 12 Line 65 "(IIc")" should read --(IIIc")--.

Column 15 Line 28 after "(XXVc')" insert period --.--.

Column 15 Line 36 "did compound" should read --diol compound--.

Column 15 Line 42 "Scheme" should read --Schemes--.

Column 15 Line 60 "mount" should read --amount--.

Column 16 Line 8 "[$^{14}$]" should read --[$^{14}$C]--.

Column 16 Line 44 "TEST EXAMPLE" should read --TEST EXAMPLE II--.

Column 17 Line 8 between "sonification" and "Platelet" delete semicolon and insert period --.--.

Column 17 Lines 9-10 "preparation were" should read --preparations were--.

Column 17 Line 17 "120-1800" should read --120-180--.

Column 17 Line 36 "in duplicated" should read --in duplicate--.

Column 17 Table 2, under column "IC$_{50}$", row "33": "0.019" should read --0.119--.

UNITED STATES PATENT AND TRADEMARK OFFICE
CERTIFICATE OF CORRECTION

PATENT NO. : 5,700,817  
DATED : December 23, 1997  
INVENTOR(S) : Soon Hyung Woo et al.

Page 5 of 9

It is certified that error appears in the above-identified patent and that said Letters Patent is hereby corrected as shown below:

Column 18 Line 56 after "addition" insert --of--.

Column 19 Line 18 "1.20-190" should read --1.20-1.90--.

Column 20 Line 7 "2.30-260" should read --2.30-2.60--.

Column 21 Line 35 "285" should read --2851--.

Column 24 Line 13 "919." should read --919,--.

Column 24 Line 13 "864 cm$^1$" should read --864 cm$^{-1}$--.

Column 24 Line 15 "octadecylcarbonyl" should read --octadecylcarbamoyl--.

Column 24 Line 16 "oxetanyol" should read --oxetanyl--.

Column 24 Line 67 "CI" should read --Cl--.

Column 26 Line 11 "IR(Kbr)" should read --IR(KBr)--.

Column 26 Line 15 "2-[[-Acetyl" should read --2-[[N-Acetyl--.

Column 27 Line 51 "3-oxetanyl]]" should read --3-oxetanyl]--.

Column 28 Line 60, diagram under Example 8, "OCNHC$_{15}$" should read --OCNHC$_{16}$--.

Column 30 Line 20 "718 (M$^+$1)" should read --718 (M$^+$+1)--.

Column 30 Line 48 "evoution" should read --evolution--.

UNITED STATES PATENT AND TRADEMARK OFFICE
CERTIFICATE OF CORRECTION

PATENT NO. : 5,700,817
DATED : December 23, 1997
INVENTOR(S) : Soon Hyung Woo et al.

It is certified that error appears in the above-indentified patent and that said Letters Patent is hereby corrected as shown below:

Column 31 Line 61 diagram under Example 10, the plus sign should be under "N" and not under the line.

Column 32 Line 20 "2.37(2H" should read --2.37(t, 2H--.

Column 32 Line 39 "$cm^{-18}$" should read --$cm^{-1}$--.

Column 32 Line 50 diagram under Example 11, the plus sign should be under "N" and not under the line.

Column 33 Line 13 diagram under Example 12, the plus sign should be under "N" and not under the line.

Column 34 Line 6 diagram under Example 13, the plus sign should be under "N" and not under the line.

Column 34 Line 38 "mp: 48.3-521°C" should read --mp: 48.3-5.21°C--.

Column 34 Line 40 "d 0.87" should read --δ 0.87--.

Column 35 Line 17 "at a" should read --as a--.

Column 36 Line 20 "Example 15-18" should read --Examples 15-18--.

Column 36 Line 23 "bis-hydroxymethyl)" should read --bis-(hydroxymethyl)--.

Column 36 Line 25 "cycloprane" should read --cycloproane--.

Column 40 Line 53 "1.70-200" should read --1.71-2.00--.

Column 41 Line 63 "2.15-222" should read --2.15-2.22--.

UNITED STATES PATENT AND TRADEMARK OFFICE
CERTIFICATE OF CORRECTION

PATENT NO. : 5,700,817
DATED : December 23, 1997
INVENTOR(S) : Soon Hyung Woo et al.

It is certified that error appears in the above-identified patent and that said Letters Patent is hereby corrected as shown below:

Column 44 Line 1 "COOCH$_2$" should read --COOCH$_3$--.

Column 44 Line 20 "cis ismer" should read --cis isomer--.

Column 44 Line 42 "2:13" should read --2.13--.

Column 45 Line 62 "5,10" should read --5.10--.

Column 45 Line 67 "(M$^+$-CI)" should read --(M$^+$-Cl)--.

Column 47 Line 40 "pyrindinium" should read --pyridinium--.

Column 48 Line 5 "IR(KRr)" should read --IR(KBr)--.

Column 48 Line 29 "696" should read --1696--.

Column 49 Line 46 "(M$^+$Cl)" should read --(M$^+$-Cl)--.

Column 52 Line 43 "(t, 1H, J=7.8 Hz)" should read --(t, 1H, J=7.5 Hz)--.

Column 52 Line 52 before "0.88" insert --δ--.

Column 53 Line 51 "2.17-1.25" should read --2.17-2.25--.

Column 54 Line 29 before "mixture" insert --reaction--.

Column 54 Line 50 "H-NMR" should read --$^1$H-NMR--.

Column 56 Line 61 "$^1$HNMR" should read ---$^1$H-NMR--.

Column 57 Line 37 "102 ml" should read --102 mg--.

UNITED STATES PATENT AND TRADEMARK OFFICE
CERTIFICATE OF CORRECTION

PATENT NO. : 5,700,817
DATED : December 23, 1997
INVENTOR(S) : Soon Hyung Woo et al.

It is certified that error appears in the above-identified patent and that said Letters Patent is hereby corrected as shown below:

Column 58 Line 25 "example with 3e" should read --example 3e with--.

Column 59 Line 47 "(M⁺1)" should read --(M⁺+1)--.

Column 59 Line 56 "426" should read --4.26--.

Column 60 Line 53 "¹HNMR" should read ---¹H-NMR--.

Column 60 Line 57 "8.14 (t, 2H, J=7.8 Hz)" should read --8.14 (t, 2H, J=7.5 Hz)--.

Column 61 Line 31 "quinoline" should read --quinolinium--.

Column 61 Line 66 "Hexadecyoxy" should read --Hexadecyloxy--.

Column 62 Line 66 between "1112" and "776" insert comma --,--.

Column 64 Line 11 "(3 ml)" should read --(30 ml)--.

Column 64 Line 49 "(phenoxycaxbony)" should read --(phenoxycarbonyl)--.

Column 65 Line 45 "126" should read --1262--.

Column 66 Line 43 "field" should read --yield--.

Column 66 Line 47 "carbony" should read --carbonyl--.

Column 67 Line 13 after "44c" delete semicolon --;--.

Column 67 Line 55 "3.06-3.06" should read --3.06-3.08--.

UNITED STATES PATENT AND TRADEMARK OFFICE
CERTIFICATE OF CORRECTION

PATENT NO. : 5,700,817
DATED : December 23, 1997
INVENTOR(S) : Soon Hyung Woo et al.

It is certified that error appears in the above-identified patent and that said Letters Patent is hereby corrected as shown below:

Column 68 Line 27 "(b) tans" should read --(b) trans--.

Column 68 Line 27 "carbony" should read --carbonyl--.

Column 68 Line 60 "field" should read --yield--.

Column 69 Line 66 "2yl]" should read --2-yl]--.

Column 71 Line 26 "3.93", first occurrence, should read --3.44--.

Column 71 Line 37 after "example" insert --47b--.

Column 71 Line 52 "carbony" should read --carbonyl--.

Column 72 Line 6 "overal" should read --overall--.

Claim 1 Column 73 Line 23 "C(O))" should read --C(O)--.

Signed and Sealed this

Eighteenth Day of August, 1998

Attest:

BRUCE LEHMAN

Attesting Officer

Commissioner of Patents and Trademarks